US009777285B2

(12) United States Patent
Schneeberger et al.

(10) Patent No.: US 9,777,285 B2
(45) Date of Patent: Oct. 3, 2017

(54) PROMOTER, PROMOTER CONTROL ELEMENTS, AND COMBINATIONS, AND USES THEREOF

(71) Applicant: CERES, INC., Thousand Oaks, CA (US)

(72) Inventors: Richard Schneeberger, Carlsbad, CA (US); Emilio Margolles-Clark, Miami, FL (US); Tatiana Tatarinova, Los Angeles, CA (US); Yiwen Fang, Redondo Beach, CA (US); Nickolai Alexandrov, Thousand Oaks, CA (US); Leonard Medrano, Azusa, CA (US); Roger Pennell, Malibu, CA (US); Noah Theiss, Tucson, AZ (US); Danielle Grizard, Moorpark, CA (US); Shauna J. Davis, College Station, TX (US); Dennis Robles, Chatsworth, CA (US); Michael Portereiko, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 131 days.

(21) Appl. No.: 14/476,566

(22) Filed: Sep. 3, 2014

(65) Prior Publication Data
US 2015/0007365 A1 Jan. 1, 2015

Related U.S. Application Data

(62) Division of application No. 12/865,719, filed as application No. PCT/US2009/032485 on Jan. 29, 2009, now abandoned.

(60) Provisional application No. 61/025,697, filed on Feb. 1, 2008.

(51) Int. Cl.
 *C12N 15/82* (2006.01)

(52) U.S. Cl.
 CPC ..... *C12N 15/8216* (2013.01); *C12N 15/8222* (2013.01); *C12N 15/8237* (2013.01)

(58) Field of Classification Search
 None
 See application file for complete search history.

(56) References Cited

U.S. PATENT DOCUMENTS

| 6,177,611 | B1 * | 1/2001 | Rice ..................... | C07K 14/415 435/320.1 |
| 2007/0020621 | A1 * | 1/2007 | Boukharov ........... | C07K 14/415 435/6.12 |
| 2007/0130645 | A1 | 6/2007 | Wu et al. | |
| 2008/0120750 | A1 * | 5/2008 | Budworth ............. | C07K 14/415 800/300.1 |
| 2011/0191912 | A1 | 8/2011 | Alexandrov et al. | |
| 2012/0084885 | A1 | 4/2012 | Alexandrov et al. | |

FOREIGN PATENT DOCUMENTS

DE 10114063 A1 * 10/2002
WO WO 2006/034479 A2 3/2006

OTHER PUBLICATIONS

Curie et al., Nucl Acids Res 19(6):1305-10 (1991).*
Liboz et al., Plant Mol Biol 14:107-10 (1989).*
Shinn et al., AC026875 (2000).*
Gordon & Waterhouse, Nat Biotech 25(11):1231-32 (2007).*
Suhandono & Pancoro, Rep. Granted Res., Asahi Glass Foundation 75:1-7 (2007).*
AC011914 (*Arabidopsis thaliana* chromosome 1 BAC F14K14 genomic sequence), NCBI database, Jan. 19, 2001.
AC026875/c 2000.
Chung et al, "Effect of 5'-UTR introns on gene expression in *Arabidopsis thaliana*", BMC Genomics, 7, pp. 120 (1-13), May 2006 (May 2006).
Chung et al., BMC Genomics 7:120 (2006).
Curie et al., "Cis and trans-acting elements involved in the activation of *Arabidopsis thaliana* A1 gene encoding the translation elongation factor EF-1α", Nucleci Acids Res, 19(6), pp. 1305-1310, 1991.
Curie et al., Nucl. Acids Res. 19(6):1305-1 0 (1991).
CW843312.
GenBank X16431—1991.
Gordon & Waterhouse, Nat Biotech 25(11 ):1231-32 (2007).
Kim, Mi Jung, et al., "Seed-speciWc expression of sesame microsomal oleic acid desaturase is controlled by combinatorial properties between negative is-regulatory elements in the SeFAD2 promoter and enhancers in the 5-UTR intron", 2006, Molegular Gen Genomics, vol. 276, pp. 351-368.
Komarnytsky, Genetic Engin 25:113 (2003).
Liboz et al., Plant Mol Bioi 14-1 Jul. 1989.
Mello & Conte, Nature 431 :338-42 (2004).
Noll, Gundula A. et al., "Spatial and temportal regulation of the forisome gene fort in the phloem during plant development", 2007, Plant Molecular Biology, vol. 65, pp. 285-294.
Office Action issued in corresponding Canadian Application No. 2,713,138 on Jun. 4, 2012.
Sato et al., "*Arabidopsis thaliana* genomic DNA, chromosome 5, P1 clone: MBK5," NCBI nucleotide database, AB005234, Feb. 14, 2004 (Feb. 14, 2004).
Shinn et al, "Genomic sequence for *Arabidopsis thaliana* BAC T6D22 from chromosome 1, complete sequence", GenBank nucleotide database entry, AC026875, Jun. 28, 2000 (Jun. 28, 2000), http://www.ncbi.nlm.nih.gov/nuccore/AC026875.

(Continued)

*Primary Examiner* — Amjad Abraham
*Assistant Examiner* — Russell Boggs
(74) *Attorney, Agent, or Firm* — Dentons US LLP

(57) ABSTRACT

The present invention is directed to promoter sequences and promoter control elements, polynucleotide constructs comprising the promoters and control elements, and methods of identifying the promoters, control elements, or fragments thereof. The invention further relates to the use of the present promoters or promoter control elements to modulate transcript levels in plants, and plants containing such promoters or promoter control elements.

25 Claims, 1 Drawing Sheet

(56) References Cited

OTHER PUBLICATIONS

Takada, Shinobu and Gerd Jugens, "Transcriptional regulation of epidermal cell fate in the Arabidopsis embryo", 2007, Development, vol. 134, pp. 1141-1150.

* cited by examiner

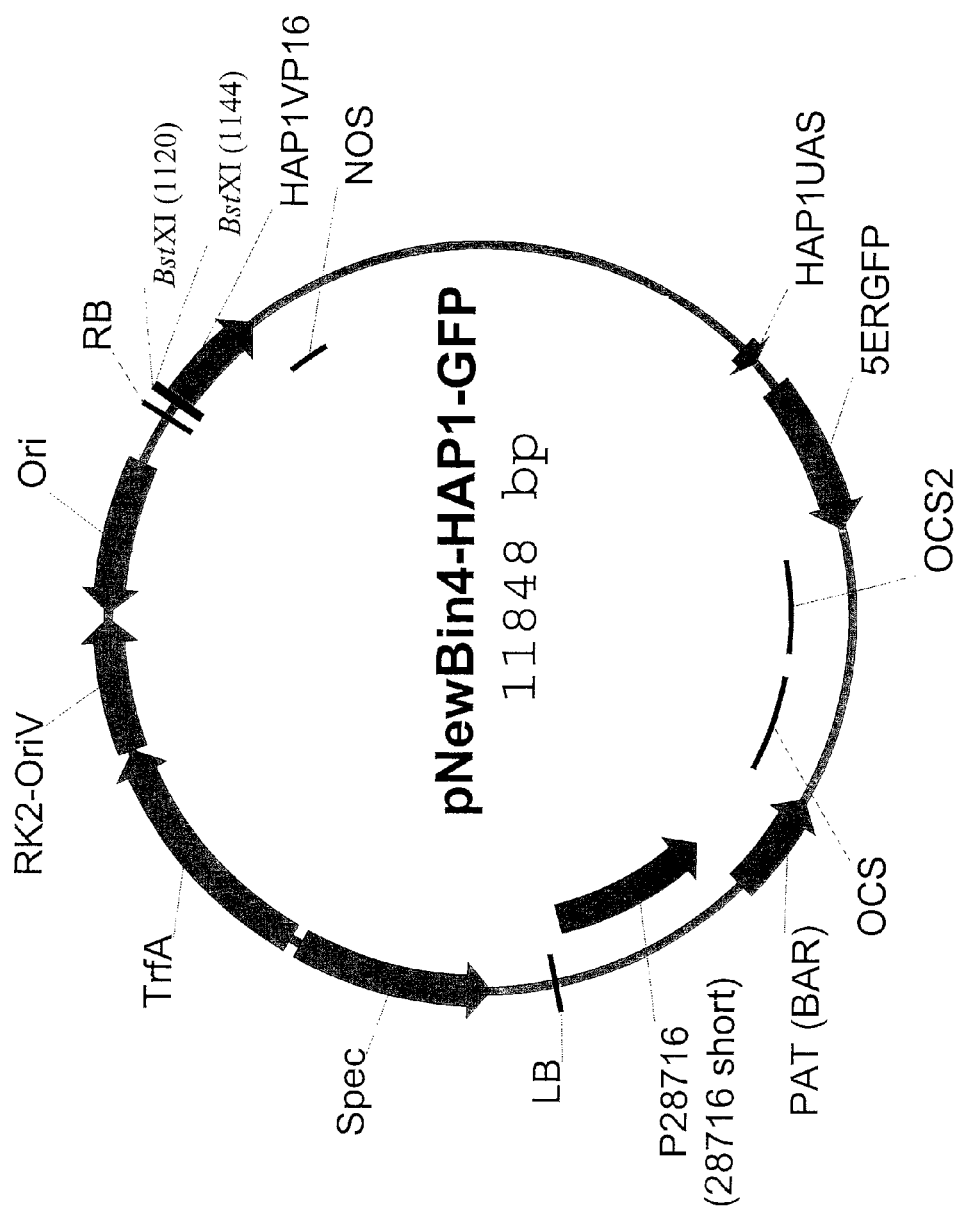

SEQUENCE LISTING

```
<160> NUMBER OF SEQ ID NOS: 87

<210> SEQ ID NO 1
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0960
<220> FEATURE:
<221> NAME/KEY: misc_feature
<222> LOCATION: (781)..(789)
<223> OTHER INFORMATION: Motif name:GLMHVCHORD
<220> FEATURE:
<221> NAME/KEY: misc_feature
<222> LOCATION: (909)..(916)
<223> OTHER INFORMATION: Consensus TATABOX
<220> FEATURE:
<221> NAME/KEY: misc_feature
<222> LOCATION: (956)..(1000)
<223> OTHER INFORMATION: 5' untranslated region

<400> SEQUENCE: 1
ttataatatg aacagactcg tttgcaattt gatgcgtctc gcactctcga gttttttcaaa      60 cattcatcta tatatgtttg ataccatcac gccactaaga tgattggctt taagtggatc     120
taggaaactt ctttactagc agaaaacatc aatattctaa tccttacttt agataaaata     180
ttatttataa ctgctactaa aaattaccgc ctaataaagc aaatttaacc aatctgatac     240
cccaacccca agtgacattc actctaaatg gtgaaggtaa ataccaatat atttagagta     300
tttatccaaa aaaaaaattg ccaatatatt tcatcccagc tataagatat tattttcatt     360
cactagactt tatttgactt ggtaaaaaca tgttacctaa tgcaaaattt ctaaaagcac     420
attttagcta tccgaccaca actctcgcaa ttaggcttca ggaactatag tagttttttgg     480 taaaatttct tcattgtcaa ctctttaaca ctataaatta tgtacaagga ctaaagtcac     540
tttatgctac atcattaccc acaaatttca taaaccattg gattatcgaa taattacgta     600
tataaaaaaa ataaagtacg ctcttaaaaa aattagatat ggttgctcga aaagaaacat     660
ggtgcgtcga cgagtcgcta cctctcacgc tttctttgaa taatttataa tatagtcttt     720
gattttctcc gcaatggtcc ccttcatgcc atctacttac tttcaccttt caagtgcttc     780
atgactcatc aatctcacga ttagaacttc tcttttcttt ctccttctat tttattaaaa     840
tttacgtatg cttcagccac ttggattagt tattagtgta aggtaacact actttcgatt     900
tattcatcta taaaaaccaa aattagagtg catttcattg atctataacca tcatacttgt     960 caacaaaaat tttcttaaag aacgcataac tgtttttttc                          1000

<210> SEQ ID NO 2
<211> LENGTH: 400
<212> TYPE: DNA
<213> ORGANISM: Arabidopsis thaliana
<220> FEATURE:
<221> NAME/KEY: misc_feature
<222> LOCATION: (1)..(400)
<223> OTHER INFORMATION: Ceres Promoter YP2585
<220> FEATURE:
<221> NAME/KEY: misc_feature
<222> LOCATION: (54)..(61)
```

```
<223> OTHER INFORMATION: Motif name:PROXBBNNAPA
<220> FEATURE:
<221> NAME/KEY: misc_feature
<222> LOCATION: (131)..(137)
<223> OTHER INFORMATION: Motif name:ANAERO1CONSENSUS
<220> FEATURE:
<221> NAME/KEY: misc_feature
<222> LOCATION: (198)..(202)
<223> OTHER INFORMATION: Motif name:ROOTMOTIFTAPOX1
<220> FEATURE:
<221> NAME/KEY: misc_feature
<222> LOCATION: (233)..(239)
<223> OTHER INFORMATION: Motif name:TATABOX4
<220> FEATURE:
<221> NAME/KEY: misc_feature
<222> LOCATION: (263)..(400)
<223> OTHER INFORMATION: 5' untranslated region
<220> FEATURE:
<221> NAME/KEY: misc_feature
<222> LOCATION: (151)..(400)
<223> OTHER INFORMATION: Ceres Promoter YP2581

<400> SEQUENCE: 2
tcctaaataa cttttctag cggagagtgt ctttccaata atttaataaa aatggtgttt      60
gtatatcaaa aaaaaagaa aaagaaact gatcgagata gaacgtttgc agttttataa     120
acaatttaaa aaacaaaaaa aattaaactc aatgtatttt ttattaattc acaaacaata    180
ataaatcata ggatcgaata tttacacggt atcaaaacct actcgccgct actatataaa   240
aattgaagtc aaatatcaac cgcaattatt aaaccagcca gaccaataat tcataaactt   300
aatataaaca taaataaatt aatgttacac aacgatatat ggtagggtta ttactatctt   360
cttcctctca aaacacatct cctaaccta agctttagac                          400

<210> SEQ ID NO 3
<211> LENGTH: 1251
<212> TYPE: DNA
<213> ORGANISM: Arabidopsis thaliana
<220> FEATURE:
<221> NAME/KEY: misc_feature
<222> LOCATION: (1)..(1251)
<223> OTHER INFORMATION: Ceres Promoter PT0998
<220> FEATURE:
<221> NAME/KEY: misc_feature
<222> LOCATION: (178)..(184)
<223> OTHER INFORMATION: Motif name:ANAERO1CONSENSUS
<220> FEATURE:
<221> NAME/KEY: misc_feature
<222> LOCATION: (185)..(191)
<223> OTHER INFORMATION: Motif name:ANAERO1CONSENSUS
<220> FEATURE:
<221> NAME/KEY: misc_feature
<222> LOCATION: (199)..(209)
<223> OTHER INFORMATION: Motif name:ARE1
<220> FEATURE:
<221> NAME/KEY: misc_feature
<222> LOCATION: (277)..(283)
<223> OTHER INFORMATION: Motif name:ANAERO1CONSENSUS
<220> FEATURE:
<221> NAME/KEY: misc_feature
<222> LOCATION: (313)..(319)
<223> OTHER INFORMATION: Motif name:ANAERO1CONSENSUS
<220> FEATURE:
<221> NAME/KEY: misc_feature
<222> LOCATION: (992)..(999)
<223> OTHER INFORMATION: Motif name:NRRBNEXTA
<220> FEATURE:
<221> NAME/KEY: misc_feature
<222> LOCATION: (1077)..(1082)
<223> OTHER INFORMATION: Motif name:TATABOX5
<220> FEATURE:
<221> NAME/KEY: misc_feature
<222> LOCATION: (1168)..(1250)
<223> OTHER INFORMATION: 5' untranslated region
```

```
<220> FEATURE:
<221> NAME/KEY: misc_feature
<222> LOCATION: (1014)..(1170)
<223> OTHER INFORMATION: Ceres Promoter PD3457

<400> SEQUENCE: 3
agaatatttc tactcataaa caataagaat aattcacaat atcacatgct agttatttag      60
tttaagtttt accaagacaa agagctggtg gattactgtg aaaatgtcca cttatgcata     120
ttaaaaattt ggtagactaa tcgactagtt gctaattgtt ccataatttc acaaaaaaaa     180
caaaaaacaa ataacctagc ccagtcacca ctatatcatt gtggcagatt tattaaagtt     240
agccttagcc cccaacataa tttgaaaagg caagcaaaac aaagacaaac ttgcaaaagt     300
ctaatctttc tgaaacaaaa catataaatt aaaatattaa tttgtttatt taaatgcaat     360
gtcgtattga aattaaaaat ctcaatgttc ttgttgtttt gtgctaagtt ctgaaaagtt     420
ttgaataaca acacatacaa agtactctgt tacttatact gtaacttgta acttccatta     480
cagagagaga gactacactg gctctataat gtacatgaag atgtgtaatt gtgtaatttc     540
tcttgtatta atattaactt cacctgttct tgtaagagat aaactataaa gcattaaagg     600
aacttgcttt aggtgcaact aaactggttt tggacaagtg tagcaacatg aaacatgaaa     660
attcaaaggg taaggctcca cctaaaattt ataaagatgt gatgcaatgt tccaaattat     720
atctacaaaa tatttgtttc gtgtggaaca agccctcttt catatgaata gttctacaca     780
agcatgaatt agatattact aattaaacta ttaaagaact cgacctacaa aactgtctat     840
atatttccct ctttcgaatt acgtatctgt gtcaaagatt gtcatcacca atctacatat     900
ttttattcat cagtaccata cacgtatata taatatatct atttcaaata taaaaaaaaa     960
actttggaaa aataaaacat tgtctggttt tatagtggat taggtaaaac caaaaaaaga    1020
aaagcttact tgatccaaca tacatactaa ctctcaacag atacaaacac aagtttatta    1080
tttaccaact cttatctcaa aagattcttc tcaataattt atcctccttt gaccccatata   1140 tagacacaca tttgacacca tatgtcatgc acaaaacatc atcatctctt gatctatctt    1200
tcagttctct tgtcaatttt cccccaaaaa gaaaaaggat ataagaagat a              1251

<210> SEQ ID NO 4
<211> LENGTH: 730
<212> TYPE: DNA
<213> ORGANISM: Arabidopsis thaliana
<220> FEATURE:
<221> NAME/KEY: misc_feature
<222> LOCATION: (1)..(730)
<223> OTHER INFORMATION: Deletion of Ceres Promoter YP0286
<220> FEATURE:
<221> NAME/KEY: misc_feature
<222> LOCATION: (1)..(730)
<223> OTHER INFORMATION: Ceres Promoter YP2219
<220> FEATURE:
<221> NAME/KEY: misc_feature
<222> LOCATION: (505)..(509)
<223> OTHER INFORMATION: Motif name:ABRELATERD1
<220> FEATURE:
<221> NAME/KEY: misc_feature
<222> LOCATION: (627)..(635)
<223> OTHER INFORMATION: Motif name:TATABOX4
<220> FEATURE:
<221> NAME/KEY: misc_feature
<222> LOCATION: (667)..(730)
<223> OTHER INFORMATION: 5' untranslated region
<220> FEATURE:
<221> NAME/KEY: misc_feature
<222> LOCATION: (542)..(730)
<223> OTHER INFORMATION: Ceres Promoter YP2229
```

<400> SEQUENCE: 4

```
attatttatt tatttttaat aaagaagcga ttggtgtttt catagaaatc atgatagatt      60
gataggtatt tcagttccac aaatctagat ctgtgtgcta tacatgcatg tattaatttt     120
ttccccttaa atcatttcag ttgataatat tgctctttgt tccaacttta gaaaaggtat     180
gaaccaacct gacgattaac aagtaaacat taattaatct ttatatatat gagataaaac     240
cgaggatata tatgattgtg ttgctgtcta ttgatgatgt gtcgatatta tgcttgttgt     300
accaatgctc gagccgagcg tgatcgatgc cttgacaaac tatatatgtt tcccgaatta     360
attaagtttt gtatcttaat tagaataaca ttttttataca atgtaatttc tcaagcagac    420
aagatatgta tcctatatta attactatat atgaattgcc gggcacctac caggatgttt     480
caaatacgag agcccattag tttccacgta aatcacaatg acgcgacaaa atctagaatc     540
gtgtcaaaac tctatcaata caataatata tatttcaagg gcaatttcga cttctcctca     600
actcaatgat tcaacgccat gaatctctat ataaaggcta caacaccaca aaggatcatc     660
agtcatcaca accacattaa ctcttcacca ctatctctca atctctcgtt tcatttcttg     720
acgcgtgaaa                                                            730
```

<210> SEQ ID NO 5
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP0286
<220> FEATURE:
<221> NAME/KEY: misc_feature
<222> LOCATION: (142)..(146)
<223> OTHER INFORMATION: Motif name:ABRELATERD1
<220> FEATURE:
<221> NAME/KEY: misc_feature
<222> LOCATION: (148)..(157)
<223> OTHER INFORMATION: Motif name:O2F3BE2S1
<220> FEATURE:
<221> NAME/KEY: misc_feature
<222> LOCATION: (149)..(155)
<223> OTHER INFORMATION: Motif name:ACGTOSGLUB1
<220> FEATURE:
<221> NAME/KEY: misc_feature
<222> LOCATION: (151)..(155)
<223> OTHER INFORMATION: Motif name:ABRELATERD1
<220> FEATURE:
<221> NAME/KEY: misc_feature
<222> LOCATION: (372)..(379)
<223> OTHER INFORMATION: Motif name:RYREPEATVFLEB4
<220> FEATURE:
<221> NAME/KEY: misc_feature
<222> LOCATION: (774)..(778)
<223> OTHER INFORMATION: Motif name:ABRELATERD1
<220> FEATURE:
<221> NAME/KEY: misc_feature
<222> LOCATION: (926)..(930)
<223> OTHER INFORMATION: Putative TSS element
<220> FEATURE:
<221> NAME/KEY: misc_feature
<222> LOCATION: (897)..(904)
<223> OTHER INFORMATION: Motif name:TATABOX4

<400> SEQUENCE: 5

```
gaaaacaatc ataggttacg ctattatcat cgaaaggtat gtgatgcata ttcccattga      60
accagatttc catatatttt atttgtaaag tgataatgaa tcacaagatg attcaatatt     120
aaaaatgggt aactcacttt gacgtgtagt acgtggaaga atagttagct atcacgcata     180
tatatatcta tgattaagtg tgtatgacat aagaaactaa aatatttacc taaagtccag     240
```

```
ttactcatac tgattttatg catatatgta ttatttattt attttaata aagaagcgat    300 tggtgttttc atagaaatca tgatagattg ataggtattt cagttccaca aatctagatc    360
tgtgtgctat acatgcatgt attaatttt tccccttaaa tcatttcagt tgataatatt    420
gctctttgtt ccaactttag aaaaggtatg aaccaacctg acgattaaca agtaaacatt    480
aattaatctt tatatatg agataaaacc gaggatatat atgattgtgt tgctgtctat    540
tgatgatgtg tcgatattat gcttgttgta ccaatgctcg agccgagcgt gatcgatgcc    600
ttgacaaact atatatgttt cccgaattaa ttaagttttg tatcttaatt agaataacat    660
ttttatacaa tgtaatttct caagcagaca agatatgtat cctatattaa ttactatata    720
tgaattgccg ggcacctacc aggatgtttc aaatacgaga gcccattagt ttccacgtaa    780
atcacaatga cgcgacaaaa tctagaatcg tgtcaaaact ctatcaatac aataatatat    840
atttcaaggg caatttcgac ttctcctcaa ctcaatgatt caacgccatg aatctctata    900
taaaggctac aacaccacaa aggatcatca gtcatcacaa ccacattaac tcttcaccac    960
tatctctcaa tctctcgttt catttcttga cgcgtgaaaa                            1000
```

```
<210> SEQ ID NO 6
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP1692
<220> FEATURE:
<221> NAME/KEY: misc_feature
<222> LOCATION: (737)..(741)
<223> OTHER INFORMATION: Motif name:ABRELATERD1
<220> FEATURE:
<221> NAME/KEY: misc_feature
<222> LOCATION: (62)..(67)
<223> OTHER INFORMATION: Motif name:ACGTTBOX
<220> FEATURE:
<221> NAME/KEY: misc_feature
<222> LOCATION: (523)..(528)
<223> OTHER INFORMATION: Motif name:ACGTCBOX
<220> FEATURE:
<221> NAME/KEY: misc_feature
<222> LOCATION: (553)..(559)
<223> OTHER INFORMATION: Motif name:ABRERATCAL
<220> FEATURE:
<221> NAME/KEY: misc_feature
<222> LOCATION: (568)..(574)
<223> OTHER INFORMATION: Motif name:ABRERATCAL
<220> FEATURE:
<221> NAME/KEY: misc_feature
<222> LOCATION: (810)..(817)
<223> OTHER INFORMATION: Motif name:INRNTPSADB
<220> FEATURE:
<221> NAME/KEY: misc_feature
<222> LOCATION: (867)..(872)
<223> OTHER INFORMATION: Motif name:TATABOX5
<220> FEATURE:
<221> NAME/KEY: misc_feature
<222> LOCATION: (901)..(905)
<223> OTHER INFORMATION: Putative TSS
<220> FEATURE:
<221> NAME/KEY: misc_feature
<222> LOCATION: (905)..(1000)
<223> OTHER INFORMATION: 5' untranslated region
<220> FEATURE:
<221> NAME/KEY: misc_feature
<222> LOCATION: (813)..(813)
<223> OTHER INFORMATION: n is a, c, t, g, unknown, or other

<400> SEQUENCE: 6
```

```
ttgagatctc aatacgaaaa tgaacccttt cgtttgattt atcaaagcct tttattttga      60
aaacgttaaa tcctcactag gatctctctt tatattaatg gttaaaaaca tatgcatgtt     120
ttgtgttttt gcatcttctt tttcatagac aaaagcaaga tgagtcttag aaggacatca     180
atgtcataga catggcttta gtatcttttg agtgtgcttt aaatgatgat gatttaccct     240
gaacctgaaa ttttacctat taattaattt aagtgtgcgt taaaccataa accatatact     300
ctgaacctga aattggttct aaagcacaac ctaaacttga gattggagaa tgctttaaaa     360
ggaaaaaaaa atcaaaggaa accattaatg agccatcaaa aaatattcac taatatgaca     420
agatgcattg tttattttc tttcagaat cctcagaaac taccactaaa ctcctcaagg       480
aacaaaacca tatcatgaat taggctggca atttaactct gagacgtctt tcttgtatag     540
agaataaaac atacgcgtgt aaagaaaac gcgtgaatcg aatgatgagt gttaacgttc       600
gatcgagatg ccaccaaatc ttttcattaa aatgaattgt ggaggacata ccacttttaa     660
cgaggtcatt tccactgggt gacatgtgga ctctactttg ggtggcatgt tcatatcttt     720
ccacatcacc atgtaaacgt gaaaacaccc accacactca cttacatctc aaacacatgt     780
cttcattatc gtacgtagct ccaaaaaaaa aantgaaaac taggtttagt gattctattt     840
cgcaatgtat aatatacaac ttgtaaaaat aaaatatttg aataagcatt ataaataaac     900
ccaaagaggt gttagattta tatacttaat tgtagctact aaatagagaa tcagagagaa     960
tagttttata tcttgcacga aactgcatgc tttttgagac                           1000
```

<210> SEQ ID NO 7
<211> LENGTH: 1500
<212> TYPE: DNA
<213> ORGANISM: Arabidopsis thaliana
<220> FEATURE:
<221> NAME/KEY: misc_feature
<222> LOCATION: (1)..(1500)
<223> OTHER INFORMATION: Ceres Promoter YP1894
<220> FEATURE:
<221> NAME/KEY: misc_feature
<222> LOCATION: (156)..(163)
<223> OTHER INFORMATION: Motif name:P1BS
<220> FEATURE:
<221> NAME/KEY: misc_feature
<222> LOCATION: (512)..(519)
<223> OTHER INFORMATION: Motif name:P1BS
<220> FEATURE:
<221> NAME/KEY: misc_feature
<222> LOCATION: (836)..(844)
<223> OTHER INFORMATION: Motif name:SURE2STPAT21
<220> FEATURE:
<221> NAME/KEY: misc_feature
<222> LOCATION: (1245)..(1268)
<223> OTHER INFORMATION: Motif name:PRECONSCRHSP70A
<220> FEATURE:
<221> NAME/KEY: misc_feature
<222> LOCATION: (1389)..(1396)
<223> OTHER INFORMATION: Motif name:P1BS
<220> FEATURE:
<221> NAME/KEY: misc_feature
<222> LOCATION: (1452)..(1456)
<223> OTHER INFORMATION: Putative TSS
<220> FEATURE:
<221> NAME/KEY: misc_feature
<222> LOCATION: (1425)..(1433)
<223> OTHER INFORMATION: Motif name:CONSENSUS TATA BOX
<220> FEATURE:
<221> NAME/KEY: misc_feature
<222> LOCATION: (1455)..(1500)
<223> OTHER INFORMATION: 5' untranslated region

<400> SEQUENCE: 7

```
tttttatgat cgcaagaaac aattgttatg ttattggtgt aatgttttgt attcttcatt      60
```

-continued

```
ttatatattc atattattaa acattattct ctatgaattt tttatatata tagaaaagtt    120
acatagtgta aattatatat tagaccgttg ttctagtata ttctaatctg gttaataatg    180
aacgtttgcg tggcctaatg gataaggcgc tcgcctccga agcgggagat tgtgggttcg    240
aatcccatcg cgaacgtagt ttttttgttt cagcaatttg cttatttcgt tgaaacttgg    300
ataacaacat tcatatgtgg ctcttagtcg acgaatatgt atgcgtcggc taatttggaa    360
aatctgatag cggcatccca ataactatac tcgtaattta gcaagatgat tacatgcata    420
accactctga cttataagag cgagacatgt atatagtgta gagtgtacat acgtaagcaa    480
acatcaatca attttgtctt gattggtgat ggtatattca tttttatgt agcatctcta     540
gatgctttcg ataaaggtg atatgaatat gtttacaaga aagagaaaga aaatgatata     600
tttctgaata atgttttttt ggataaatcc tcaataatgt tgtttcgaat ctatgatctc    660
tacaatatta ttaaacatat atacctacaa atttagcatc tatacgggta agacgaccat    720
tcatatatat aagggatcat gaagacaaca caaataagac atccacaaat aaattaataa    780
gccaacttgg tcttaaaaat caggcatctt attcttaaca aactttagct gatcgattag    840
tatttgcact aaccaaagaa ataataattt agtttactaa cataattgca tatatatata    900
tattatacaa ttagtagagt ggctataaag catgccacat gcacattctt taatggacag    960
acatttgaat attgaagagt ttatcgtaaa ctaaatgtca tttgaaaact gctaaaggtc    1020
ttttatttta tatactcaca taatcacatc aagaatatga cttattatat tcatcgtttt    1080
tggtcgataa taatgattct ttacaataag gacatgttga gcatgtttat aacttattta    1140
atttgactcg ttgaattgtt attattttgt taatatgctt agattccaca tctaaaataa    1200
tatctaatgc agatcatatg taatgcacat taaaggtttt acctccgata atttaatatt    1260
ccaattaatt aatatgcaat ggcagtgtaa ctaacggcag ccgttagtta atggagtcgg    1320
ttgcttgctt agttttgtt ctcgaagctt gacttttgaa acagaatgct gtttaacctc     1380
cttaaacgga atattctctt ttttagtact ttgattctat tcctctatat aaacctctct    1440
ctctctcacg aatcagagat acgaagaaac taacaacaac aagaaaaaag gaatattccg    1500
```

<210> SEQ ID NO 8
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter YP1976
<220> FEATURE:
<221> NAME/KEY: misc_feature
<222> LOCATION: (90)..(99)
<223> OTHER INFORMATION: Motif name:CARGATCONSENSUS
<220> FEATURE:
<221> NAME/KEY: misc_feature
<222> LOCATION: (202)..(210)
<223> OTHER INFORMATION: Motif name:HDZIP2ATATHB2
<220> FEATURE:
<221> NAME/KEY: misc_feature
<222> LOCATION: (454)..(463)
<223> OTHER INFORMATION: Motif name:CARGCW8GAT
<220> FEATURE:
<221> NAME/KEY: misc_feature
<222> LOCATION: (479)..(486)
<223> OTHER INFORMATION: Motif name:P1BS
<220> FEATURE:
<221> NAME/KEY: misc_feature
<222> LOCATION: (491)..(500)
<223> OTHER INFORMATION: Motif name:CARGCW8GAT
<220> FEATURE:

<221> NAME/KEY: misc_feature
<222> LOCATION: (742)..(751)
<223> OTHER INFORMATION: Motif name:CARGCW8GAT
<220> FEATURE:
<221> NAME/KEY: misc_feature
<222> LOCATION: (945)..(951)
<223> OTHER INFORMATION: Motif name:TATABOX4
<220> FEATURE:
<221> NAME/KEY: misc_feature
<222> LOCATION: (972)..(999)
<223> OTHER INFORMATION: 5' untranslated region

<400> SEQUENCE: 8

```
agttcgacta tagaatacaa tacaaaggac acaaaatctt catgtacaat caaaaattat     60
caaccccata tcttatagtt ggaaacgatc caaaataggt tatataaata aaatatataa    120
aatatgtcaa gtataacaac tcacatcacc cttttggctt ttggggaaat atcggattta    180
tagaaaaaaa aaaataataa taataattaa racaataaaa tatttggtct gaatcttttt    240
tgagatactg ttgtatcata acaatatctt ttagagtcat tcaacatcaa tccacatgta    300
ttgcactgga acatgcattt taataaggtt ctatgtttgt taaattatgc agtcatgtaa    360
taatcaaatt ttatgataat gtctttgtaa acgctataaa ctaaaaattt ataatagtta    420
catgtgtaaa aaatgttgtc gcttaaccat gtcatatata tgttggttgg tatacgtgga    480
tatacgatac atataattgg tgtagttagc tctcattttt tttttgttt tgtacattat    540
cgtcgtacgt cgactttgta tactacttta tactccgtca aactaaaata acttaaaata    600
taataaaatt gtattcatta tattcacaga aaaataaaaa tgttattctt gtaacaagtc    660
aaactaaaaa aaagggaaaa taagaatgac taaatgttta tgaagacgaa agagagaaaa    720
cattttgta ttttattga cattttttag cagtcaagat gttagggtga ggaaatgaaa    780
agttaataga aacatgtata gtaaaagaga cattttttt tgattgtaga tagtgaatgt    840
acgagtatac tatccccctt agatttaaaa aaaaaaaaca ttttgcagaa ttattcataa    900
actaaaattt agaaaataat gtaggagtta ggtgaaccgc ttatatataa taaagaccca    960
attagtaagt agatcaaaca caaatcaaat cagccatac                           999
```

<210> SEQ ID NO 9
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP2016
<220> FEATURE:
<221> NAME/KEY: misc_feature
<222> LOCATION: (349)..(978)
<223> OTHER INFORMATION: Intron
<220> FEATURE:
<221> NAME/KEY: misc_feature
<222> LOCATION: (207)..(214)
<223> OTHER INFORMATION: Motif name:P1BS
<220> FEATURE:
<221> NAME/KEY: misc_feature
<222> LOCATION: (260)..(268)
<223> OTHER INFORMATION: Motif name:TELOBOXATEEF1AA1
<220> FEATURE:
<221> NAME/KEY: misc_feature
<222> LOCATION: (978)..(1000)
<223> OTHER INFORMATION: Motif name:5'UTR
<220> FEATURE:
<221> NAME/KEY: misc_feature
<222> LOCATION: (294)..(300)
<223> OTHER INFORMATION: Motif name:TATABOX2
<220> FEATURE:
<221> NAME/KEY: misc_feature

```
<222> LOCATION: (327)..(348)
<223> OTHER INFORMATION: 5' untranslated region

<400> SEQUENCE: 9
attacattct cttaacctgc aaagtgtata tcgtccaagt aaaaccttct tgatttaatt      60
cgcgttgaac caaatttaat tatattccac ttttggattg aaactatcaa attcaaatta     120
gcttgactta tgaaacaaga gcgacccctc gaggttagtg gacttttatg aaacgcgacc     180
gactcttcaa ggcccaaaga aaagagaat attcggcggg ataggggtac gtttgtaatt      240
tggcaaacga tgttatgtta aaccctaact tattatttct ttcgattcac cactataaat     300
aaactcgaat cccaaacata gctttattcc ttgcttcatt tttcgtcacc ctagccgctt     360
tactctcttg cgatatctct gaggtaagct ttttcgtcac catcttcgat ctgcttcttt     420
ctcttctgtt gatctgtgtt gaatctgttt cgatccttct cgtttgtttg ttgtaatctc     480
ttggattcga ttctctttgt ttatagatcg tttggaattt ctgatctgtg gtgtaaagtt     540
ttatcgattt aggagaacaa agttttacag tgccatcgta ttgttttttt tcttcatgcc     600
agctgatgat aaactatatg atcgatctgg ttctgaaatt tttgtattgt tcaatggatt     660
gttgattgga tcttttgatg tatgtgatat taattgtcga tttgaattgt gattaggtaa     720
ttctggagca gcataaacaa tcaattgatt cattcttctt gataccaagt tgtggaaact     780
ctaggattgt ttgctgtata tctccagaat tgctgttttg attgaattta ggtcgcttag     840
ctcagttgat agagcaccac attttttgtg gtagaaatcg gtttgaatcc gatagcggct     900
tttaacaatg attgtttttt gtgttcataa gtctactgtt tttcttgatt caatatttga     960
ttgttctttt tattgcagat ttgtttgaca gtctctaacc                          1000

<210> SEQ ID NO 10
<211> LENGTH: 397
<212> TYPE: DNA
<213> ORGANISM: Arabidopsis thaliana
<220> FEATURE:
<221> NAME/KEY: misc_feature
<222> LOCATION: (1)..(397)
<223> OTHER INFORMATION: Ceres Promoter YP2097
<220> FEATURE:
<221> NAME/KEY: misc_feature
<222> LOCATION: (36)..(41)
<223> OTHER INFORMATION: Motif name:DRE2COREZMRAB17
<220> FEATURE:
<221> NAME/KEY: misc_feature
<222> LOCATION: (161)..(167)
<223> OTHER INFORMATION: Motif name:ABRERATCAL
<220> FEATURE:
<221> NAME/KEY: misc_feature
<222> LOCATION: (237)..(246)
<223> OTHER INFORMATION: Motif name:ABREATRD22
<220> FEATURE:
<221> NAME/KEY: misc_feature
<222> LOCATION: (240)..(246)
<223> OTHER INFORMATION: Motif name:ABRERATCAL
<220> FEATURE:
<221> NAME/KEY: misc_feature
<222> LOCATION: (283)..(289)
<223> OTHER INFORMATION: Motif name:TATABOX3
<220> FEATURE:
<221> NAME/KEY: misc_feature
<222> LOCATION: (317)..(397)
<223> OTHER INFORMATION: 5' untranslated region

<400> SEQUENCE: 10
ccaaattaaa tgagcctatt gggcttcttg tcttagtcgg tgtagagccc aattgttgtt      60 ttattttta ataatgcaaa agtattaagc gataaataaa taagcatcgc aatcgtccca     120
```

```
aaactgtgtg tatgcatcag acatgagcat atagagtaag cacgtgtcca cactttttca      180
caaagttatc taaaaacaaa aaacaattaa ttagcattcg acgtgtacat atcactcgcc      240
acgtgtacaa gagccttggc cttttgtctt cttcttcttg tctattaata tcatctcctg      300
attatactct cttttgacca agctgcttct tctccatcta tccaacatct caaatctcag      360
taatcttgtc ccttcgattc tgttttggac gtttgta                              397
```

```
<210> SEQ ID NO 11
<211> LENGTH: 718
<212> TYPE: DNA
<213> ORGANISM: Arabidopsis thaliana
<220> FEATURE:
<221> NAME/KEY: misc_feature
<222> LOCATION: (1)..(718)
<223> OTHER INFORMATION: Ceres Promoter YP2538
<220> FEATURE:
<221> NAME/KEY: misc_feature
<222> LOCATION: (166)..(170)
<223> OTHER INFORMATION: Motif name:ABRELATERD1
<220> FEATURE:
<221> NAME/KEY: misc_feature
<222> LOCATION: (530)..(534)
<223> OTHER INFORMATION: Motif name:ABRELATERD1
<220> FEATURE:
<221> NAME/KEY: misc_feature
<222> LOCATION: (298)..(307)
<223> OTHER INFORMATION: Motif name:CARGCW8GAT
<220> FEATURE:
<221> NAME/KEY: misc_feature
<222> LOCATION: (650)..(658)
<223> OTHER INFORMATION: Motif name:TELOBOXATEEF1AA1
<220> FEATURE:
<221> NAME/KEY: misc_feature
<222> LOCATION: (671)..(679)
<223> OTHER INFORMATION: Motif name:TATABOX4

<400> SEQUENCE: 11
atgttgaaca tctgaatatt gttttttttgt tcttttttatt ctcattctct tatgtataca      60
ttcattactc aatttttttaa tgtactatac tatatctttta ctcatcaaat tattaacttt     120
gagactcact aatcaaaaaa ttctcactac tcttttaaac acaaacacgt tagatgttaa      180
aattggttgt attcgccctc ataaccaatt ggaaagtggc ctaaataaga gaatgatgcg      240
acactaaaaa gccgaagaaa attctagcca tttgagagat gatacaatga gattcagctt      300
taaaatgtat gacctattta ttactgacaa caaacgaatt acatttgttt acgatctttg      360
agttcacaat ggttttgcata aatgtctaac aaatgtcttg agaatttgtt tcacaagaca     420
agcaaaccaa ttgcactcaa tttgcataaa gtctctaaat agtaaaacaa tacgcacata     480
gttcttaaga tcacaagata agcaaagcaa ttccactcaa tttgcatatc acgtactata     540
ttgggtgtta ttgaataagt tatgttattg ggccgggctt cttggttttgt atctcaacaa    600 aacaattata tcaacattcg gcccacaagc ccataattca gactttcgaa aaccctaatc    660
ttatgctcac ctatataaac taaaacttgt gaatccgcta gggtttactt catcgaaa      718
```

```
<210> SEQ ID NO 12
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP2552
<220> FEATURE:
<221> NAME/KEY: misc_feature
<222> LOCATION: (35)..(42)
<223> OTHER INFORMATION: Motif name:P1BS
```

```
<220> FEATURE:
<221> NAME/KEY: misc_feature
<222> LOCATION: (216)..(223)
<223> OTHER INFORMATION: Motif name:SV40COREENHAN
<220> FEATURE:
<221> NAME/KEY: misc_feature
<222> LOCATION: (647)..(653)
<223> OTHER INFORMATION: Motif name:BOXLCOREDCPAL
<220> FEATURE:
<221> NAME/KEY: misc_feature
<222> LOCATION: (710)..(718)
<223> OTHER INFORMATION: Motif name:SEF1MOTIF
<220> FEATURE:
<221> NAME/KEY: misc_feature
<222> LOCATION: (835)..(872)
<223> OTHER INFORMATION: Motif name:TATABOX

<400> SEQUENCE: 12
acattatgaa caaattcgga gatcctgaga atttgcatat cccacgtaca cgacctcaaa      60
accaatcaaa ttcaaatttc gttctttgaa agatatactt gcaattcata tacgttaaat     120
cttcagtttt tttttacacg agaatcagta ctcattagca cagcctcatt ttatgctttc     180
aatgttttta acacgagaat aagaattagg atcaagtggt ttgtgcttga aaaaagtact     240
gactagaact tttttttata taaagagttt tccacaaccc tcggagacat aattgagaga     300
agatcatcct tttaaataaa tagtcttcac tatagtaaat tcgatttcat tatatctgtc     360
ttactgtcta tattataaga gtatgcacac ttggaaacat agggatgctg tgatctccgt     420
ttgtaaaata atctatgcac gtacaaaaaa aacattaaac acatttacat atttagatgc     480
atacatgata cagtcatca atgtatgtat acacacatat actgacacta acacatgctt     540
agtgtgcgca ataattttgt ctttactcag taatttatgt ataaataatt tggtttagcg     600
cattatatac aactggtcca tttgcgccta gcgagtaatg gttaatggtt ggtatgttaa     660
caatttatcc caccagaaaa ccatatcttt tatcaaatcg cgacttcaaa tatttaatat     720
cagtcccacg acatcgacgc cgtttaatat tgttttattt gttccttttt ctcaaattaa     780
catattctag taccggcaaa acatttttta atatattatg cgtctttcta caaatatata     840
tatatatata tatatatata tatatatata tactcttcta agtatatgat gcaatggagt     900
ctctctgcat gaaagaataa aaaaaaaaca tcacaatctc tttccatttc tgagagctaa     960
aaaacctctc tctctttctc tttgattcaa gtttccaaaa                          1000

<210> SEQ ID NO 13
<211> LENGTH: 1500
<212> TYPE: DNA
<213> ORGANISM: Arabidopsis thaliana
<220> FEATURE:
<221> NAME/KEY: misc_feature
<222> LOCATION: (1)..(1500)
<223> OTHER INFORMATION: Ceres Promoter YP2563
<220> FEATURE:
<221> NAME/KEY: misc_feature
<222> LOCATION: (689)..(695)
<223> OTHER INFORMATION: Motif name:ABRERATCAL
<220> FEATURE:
<221> NAME/KEY: misc_feature
<222> LOCATION: (112)..(118)
<223> OTHER INFORMATION: Motif name:DPBFCOREDCDC3
<220> FEATURE:
<221> NAME/KEY: misc_feature
<222> LOCATION: (653)..(659)
<223> OTHER INFORMATION: Motif name:ABRERATCAL
<220> FEATURE:
<221> NAME/KEY: misc_feature
<222> LOCATION: (689)..(695)
<223> OTHER INFORMATION: Motif name:DPBFCOREDCDC3
<220> FEATURE:
```

<221> NAME/KEY: misc_feature
<222> LOCATION: (799)..(807)
<223> OTHER INFORMATION: Motif name:EVENINGAT
<220> FEATURE:
<221> NAME/KEY: misc_feature
<222> LOCATION: (1351)..(1500)
<223> OTHER INFORMATION: 5' untranslated region

<400> SEQUENCE: 13

```
gagatcttgt tcgtaattct gtgataatgt ttgataactt ctctgcccag tttgtttgaa    60
attcagtact tgaggttctc tattggacag aagatgaaca tatggactac aacacttgga   120
caatccgtaa tggacaacca cacattttgg ttgcagcgta tgtgtcgtta caaaattgaa   180
aatcaatgtc cacgaccata catgactgca cagcttggtg tttgataatt caaggaaaaa   240
gccacataaa ggttctattt cttaatctta cattttggaa gaaatcaaat cattgattta   300
agaaataata tgtaagcttg gatgctagag ctttaggtga tcctgtggcc agattaggat   360
attgatttaa cttttcttac tgctactcaa cattgattgt ctggtattaa gttgtaaaag   420
agtagtttga cttatccatt tgtgttgata taattggtta ttataatgtg attagtcaat   480
agaaaacctt agagtacata atatcaaact tttaactttg ttaattttt taggcgagtg    540
ggtgaataca tcagttagac ttgcttttgc acatcatgtg atcatcgttt aattgttata   600
tgatcggacg gtcattattt ctcattaact tctatttaaa ctgcaaatct taccacgttc   660
atttgatccg aattaaccca ttattctaca cgtgtttggt acacacaatt acaaaccaaa   720
accaatgacc ggttattctt ttttcgtgat tcagtttatt tggggtataa tggtctattt   780
tcactccaaa aacaaagaaa aatatctcaa ccttggaaaa tacctgtttt gtctaaactt   840
tttcccaaag tgccttatta cggaacattc cctacaaaaa aaccatcgtc atgtactgga   900
caaaatattc ttcaagtttg ttttcatgtt gtgttgggcc gtttaattcg catgtatccc   960
atatcggacc ttataaactt ataagttata acattaaaa tataatccat tgtcaatcc    1020
tttttttccac tttttttaat taagataaat cttaagtatt accaaatcat tattaaattt  1080
ttatatttat tattctagct ttaccattta cacatacttt accccattg tattttcatt   1140
gccgaaatgt ttcaaaaaag gatgatttaa ggggcaataa taatatttaa aaaaactgtg  1200
tttagtgatg aaacaaaacc cgccgttgga aattaaacca gcccatagag agaaaaacct  1260
ctcttaacga agaaaaacaa caacatggcc cctggtttct cttctctttc gaatctatct  1320
tcttctttta tccaatcctt tcctattttt attctcacct tctcctcgtt tttcccgaaa  1380
ctgttcttt gccctcttct ctcaattta atccaccaaa caaatcgaac agtgttcgat    1440
aactttaga ttgcaagtcc tgtttttgat ttggtcggga gaaagaaaac tagggttttg  1500
```

<210> SEQ ID NO 14
<211> LENGTH: 2001
<212> TYPE: DNA
<213> ORGANISM: Arabidopsis thaliana
<220> FEATURE:
<221> NAME/KEY: misc_feature
<222> LOCATION: (1)..(2001)
<223> OTHER INFORMATION: Ceres Promoter YP2571
<220> FEATURE:
<221> NAME/KEY: misc_feature
<222> LOCATION: (397)..(404)
<223> OTHER INFORMATION: Motif name:ABREMOTIFAOSOSEM
<220> FEATURE:
<221> NAME/KEY: misc_feature
<222> LOCATION: (1231)..(1238)
<223> OTHER INFORMATION: Motif name:ABREMOTIFAOSOSEM
<220> FEATURE:
<221> NAME/KEY: misc_feature

```
<222> LOCATION: (1558)..(1565)
<223> OTHER INFORMATION: Motif name:ABREATCONSENSUS
<220> FEATURE:
<221> NAME/KEY: misc_feature
<222> LOCATION: (1794)..(1800)
<223> OTHER INFORMATION: Motif name:TATABOX4
<220> FEATURE:
<221> NAME/KEY: misc_feature
<222> LOCATION: (1829)..(2000)
<223> OTHER INFORMATION: 5' untranslated region

<400> SEQUENCE: 14
aagcgaaacg ttatcttatg caatgtttac atttgcaaca ccaattagct tcttttttt      60 acagttgaga cttgagagac acattaaagc ttgtcatcgt tcactggaga gagtagagtg    120
tgtgagagac caagtgacct aacttcactg caacagtagt cggtaaatat ccaaacataa    180
gagctacgat ggtaacacgt gtacggtgga ggaaaagaga gccctcagat tccgttataa    240
aggaggtgag acccactcgc cggaatggaa acaaaggaga aacgtagagg taaatggttg    300
ggccactgct tcaccaaaaa gccttttcta tcttcttttt attttttgttt tgtggcttt    360 aacggttaac aatataactc ctcattccaa gacaattacg tgtcctctgt acggcttttt    420 cattttcac tttctacttc atagtgactt tagggaggcc tcaattttta attactcgag     480
gattatttag gtaatcatga atgtaactac agctttacag gtaattaaac agatgagatt    540
tagttgcgtg aaatctagct gatctggtgc ttatatcaaa tccaattgat ggagacagat    600
ttggacttaa attcatgatt gtatttgtaa tcttatatac gttatagtta aatttctttc    660
tctccgtacg tactctaact ataattatta ttaaatgctg aacgcaatgc ttttgagtgc    720
tgagaatctt tttggtctga ttcaaaaatg atgtattagt actctgaatt caatcttaac    780
ttctgcaacg aatcaatgta ttaatttata ggagatccgg ataaaattat ggatatatgc    840
acgctacttc tttcatttt aattaggtaa atggttataa ctttattta tatatcaatt      900 aaatgatttt ggtatgagat tactagtaca ctttctttgc aaatgtttta aacacgacaa    960
gacaaaaata ttacaagcat attttggtaa aaaatatcat aagctttcat atcaaaatca   1020
ttagttatga tgttagattt tttttttttt tttttaacac tacaaaaagc tctggtctta   1080
atatgttaga aattttagtc caaaccagcc tacagaggat ttagctaaac aattcccaag   1140
caccttttaa gtgttaaccg aaataacgta atatgatgtt aaaggttaca taaaaacaaa   1200
actaaagaat tttcatatga aaagttaacg tacgtgtctt agtgtaacct aatttagtt    1260 cacagtatat aaattcttta atgagatgat cgcaaaatcg ctgtatacaa tttcgtactt   1320
aattcgttag tcttgaaaag ttgacctaat ttagatcaaa ttaaggttaa ctacaataaa   1380
aatttaacta acgtaatggg attctttaaa attaaaaaat cgttgattag atagatattt   1440
tatctttaag ggagacacag agacaatttg gacaaaaaag gtcttcctga gaaagaagtg   1500
gaccacaatc gtggcgcgaa aggaacttcc tcctcccctc tgttgccttg tcattgggcc   1560
acgtatatct ccacctgatc gtgatgctta cgtggtccat ttctagatac tatagtgacc   1620
agatcaacgg tcaagattga ttctaattta gacgaaagac caacccgtca cgtcgctaga   1680
gtaaaagatt ttttgaaggc ggagggagaa aaatcaaaag ttaaaagtaa tttgaaaacg   1740
aggaagagaa aaaggaattt taaatgtttt aatgaagcgg taggccgcat gggtatataa   1800
atgggcccgc tttgtaacgt gtaacgatga tatttattca actgcgtggt ataaccaaaa   1860
aaaaaaagaa acactattcg actcttttt tgttttgta ataaacataa aataaatttt     1920
ggagagagat atttcgtcgg aaattaattg acgttcaaaa gattcgttac cggaatattt   1980
```
agtagaggcg gcgatcgagt t                                              2001

<210> SEQ ID NO 15
<211> LENGTH: 514
<212> TYPE: DNA
<213> ORGANISM: Arabidopsis thaliana
<220> FEATURE:
<221> NAME/KEY: misc_feature
<222> LOCATION: (1)..(514)
<223> OTHER INFORMATION: Ceres Promoter YP2590
<220> FEATURE:
<221> NAME/KEY: misc_feature
<222> LOCATION: (77)..(86)
<223> OTHER INFORMATION: Motif name:CARGCW8GAT
<220> FEATURE:
<221> NAME/KEY: misc_feature
<222> LOCATION: (255)..(262)
<223> OTHER INFORMATION: Motif name:MYBPLANT
<220> FEATURE:
<221> NAME/KEY: misc_feature
<222> LOCATION: (279)..(287)
<223> OTHER INFORMATION: Motif name:ATHB6COREAT
<220> FEATURE:
<221> NAME/KEY: misc_feature
<222> LOCATION: (283)..(288)
<223> OTHER INFORMATION: Motif name:TATA BOX
<220> FEATURE:
<221> NAME/KEY: misc_feature
<222> LOCATION: (314)..(514)
<223> OTHER INFORMATION: 5' untranslated region

<400> SEQUENCE: 15
agaagggctt gctgtccgtt gctcatctca tatagtaagg cccaaaaggc ccaaaggctt     60 cttttttccaa ttaaaactaa tttttgtata gcgaaattat gatgaagaaa atcgtttcat   120
ggcacgtcaa aaaactttcg cacaacaatt ttttttttaca aaagggtcac ttttatcaga   180
acctaatcta tcatagagtt cccatcaaca aaaaacctat catagagtct agtcctgtgt   240
taacgtaggt gatgggttgg tttcatggtt tacatggaca attattatgg tgtaagaaaa   300
agatgatggg tacacatatt ccatttaacc aatgtgaaag attcacatca ccttttttcga   360 tttttaatag attcggtttt accttctcgt aacgtaattc taagaaaaga aaacgtcaat   420
catatttact aggaaagata attataattt attgcttttt ctctcactct ctgacctgaa   480
atctcctact gagattttg aagtgtattc aaca                                 514

<210> SEQ ID NO 16
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter YP2606
<220> FEATURE:
<221> NAME/KEY: misc_feature
<222> LOCATION: (44)..(51)
<223> OTHER INFORMATION: Motif name:XYLAT
<220> FEATURE:
<221> NAME/KEY: misc_feature
<222> LOCATION: (339)..(348)
<223> OTHER INFORMATION: Motif name:CARGCW8GAT
<220> FEATURE:
<221> NAME/KEY: misc_feature
<222> LOCATION: (593)..(600)
<223> OTHER INFORMATION: Motif name:UP2ATMSD
<220> FEATURE:
<221> NAME/KEY: misc_feature
<222> LOCATION: (636)..(645)
<223> OTHER INFORMATION: Motif name:CARGCW8GAT
<220> FEATURE:
<221> NAME/KEY: misc_feature

```
<222> LOCATION: (655)..(664)
<223> OTHER INFORMATION: Motif name:CARGCW8GAT
<220> FEATURE:
<221> NAME/KEY: misc_feature
<222> LOCATION: (807)..(812)
<223> OTHER INFORMATION: Motif name:WBBOXPCWRKY1
<220> FEATURE:
<221> NAME/KEY: misc_feature
<222> LOCATION: (829)..(834)
<223> OTHER INFORMATION: Motif name:WBBOXPCWRKY1
<220> FEATURE:
<221> NAME/KEY: misc_feature
<222> LOCATION: (840)..(849)
<223> OTHER INFORMATION: Motif name:CARGCW8GAT
<220> FEATURE:
<221> NAME/KEY: misc_feature
<222> LOCATION: (862)..(868)
<223> OTHER INFORMATION: Motif name:TATA BOX
<220> FEATURE:
<221> NAME/KEY: misc_feature
<222> LOCATION: (916)..(1002)
<223> OTHER INFORMATION: 5' untranslated region
<220> FEATURE:
<221> NAME/KEY: misc_feature
<222> LOCATION: (666)..(1000)
<223> OTHER INFORMATION: Ceres Promoter PD3464

<400> SEQUENCE: 16
cacaacaaaa gagagctaat gttttgtaag ttagagatga tatttctttg tttatttgtt      60
ctgtaatgct tgtatatata tatatatatt gatcttttct ttattattca catgataaaa     120
acatctaaac agaaataaaa ataaaggaaa gtgaatgaat gttgaaaaat gtaagattga     180
ctacattgat ttctatatgc accttctcaa catgttaaaa ataatagcaa ttaacttaat     240
tcatagaaat aattattata tttccatgtg gtcatgtgta atacatagat acaaataatt     300
attaacgtta tcccatggtt ttctatccat ttttatact ttaaaaagtg aattcaaagt      360
tcaaataaat aattatgaga ttaacattat cccatgcgtt gattctctat ccataaactc     420
tttttttttt tttgtcaaac gatctttcca tatacatact ttaaaagttg tattcaaagg     480
ccaacaaaaa attattccct taaacttgtc ccaggaacta aaaattagaa aatatatatc     540
cctttcccca aaaatttaaa aaaccttttt tcgtcgcaat attttttttt tatagggttt     600
atacgggatt tgtatcccaa ccaggattat ataatcaatt ttttgcccca aaaacaaaat     660
aatgaaaaaa aatgaagggt ttttttgccc aaaagggaaa aagttttttt tttttttttt     720 ttttacctt actttaaata aaatatatat aagcatacaa actaataata tatgatgctt      780
attgtttttt atttaaaatg tagaactttg actatatcaa ttattttggt caaagtcttc     840 ataatttgt atatatgttt cctataaaga tttattatag atcatgtacc atttttcaca     900
gtctataaaa aggttatttc tctctaccat tttcaatatc aaaaagtttc ttcaaacaaa     960
caagtattag attaacatta tcctcttcat tttcagcaat cc                       1002

<210> SEQ ID NO 17
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP2608
<220> FEATURE:
<221> NAME/KEY: misc_feature
<222> LOCATION: (490)..(901)
<223> OTHER INFORMATION: Intron
<220> FEATURE:
<221> NAME/KEY: misc_feature
<222> LOCATION: (28)..(35)
```

<223> OTHER INFORMATION: Motif name:P1BS
<220> FEATURE:
<221> NAME/KEY: misc_feature
<222> LOCATION: (67)..(74)
<223> OTHER INFORMATION: Motif name:INRNTPSADB
<220> FEATURE:
<221> NAME/KEY: misc_feature
<222> LOCATION: (155)..(162)
<223> OTHER INFORMATION: Motif name:PYRIMIDINEBOXHVEPB1
<220> FEATURE:
<221> NAME/KEY: misc_feature
<222> LOCATION: (156)..(161)
<223> OTHER INFORMATION: Motif name:GT1GMSCAM4
<220> FEATURE:
<221> NAME/KEY: misc_feature
<222> LOCATION: (209)..(214)
<223> OTHER INFORMATION: Motif name:GT1GMSCAM4
<220> FEATURE:
<221> NAME/KEY: misc_feature
<222> LOCATION: (216)..(228)
<223> OTHER INFORMATION: Motif name:TATABOX
<220> FEATURE:
<221> NAME/KEY: misc_feature
<222> LOCATION: (279)..(489)
<223> OTHER INFORMATION: 5' untranslated region
<220> FEATURE:
<221> NAME/KEY: misc_feature
<222> LOCATION: (401)..(1000)
<223> OTHER INFORMATION: Ceres Promoter PD3739

<400> SEQUENCE: 17

```
tgaaataagt tgtacaccaa aaagtttgaa tatccggtta caaaaattag gtaggctgag    60
gtttgaaaat tgagttccag ttgttatgat atttggggac atccattaaa aagtatagta   120
tgaaattta acaaggtcta attaattttt tgaaggaaaa aatatataac taagcataaa   180
taaaaatctt atagaaacat aaatataaga aaaagattaa tatatgatgc ttataatgat   240
gagctgtcgt ctcatattct cgtttgattc aaaacgatag aaatcgacaa agaaggtgtg   300
aagaagttgg gaaaacaaaa ttaacgcttg aagaatctaa aggtttagct ttttctcaa    360
tccgatcatt caccgagaaa tattctattt tatatattta tgtgaagctc ttcaattgaa   420
gaaagaagaa gaaaagacaa tcgtcaaatg cttgactttg gtttcagttc ttcttcacga   480
cagctcaagg tgatgatcat ttttatttta ctcttctacc taatcatatc actgcgaatc   540
ttttccaaag tttcgctctt tattctctca atgtgctttt tttctgagtt gttgttgaac   600
tagggttctt ctgggtacta gtaactgttt tgctgatttt ctgagctgct tttggctata   660
gaatttcagt tttcaaacca aaccttgtcg atttcaaatc aattctagtc ggcagtagat   720
ctgatctgtc tctattgggc taggttttac agtgtatcaa ttcaccacta gttcaaagtt   780
catcagtgct tacacaagtt tacttttttt tgtatgtgtt catgatttag ctaatgatca   840
agatacttga gatataataa cacaccttat ttaatgcaaa tgggcctaca aattctacta   900
ggaagatcgg ctctttgatg ggatgggaca ccaagaaatc accatgggtt tatgatgcta   960
tcaattacta gtagtacgtg ttatcttctg aatatatatc                         1000
```

<210> SEQ ID NO 18
<211> LENGTH: 995
<212> TYPE: DNA
<213> ORGANISM: Arabidopsis thaliana
<220> FEATURE:
<221> NAME/KEY: misc_feature
<222> LOCATION: (1)..(995)
<223> OTHER INFORMATION: Ceres Promoter YP2683
<220> FEATURE:
<221> NAME/KEY: misc_feature
<222> LOCATION: (162)..(168)
<223> OTHER INFORMATION: Motif name:AMYBOX2

<220> FEATURE:
<221> NAME/KEY: misc_feature
<222> LOCATION: (271)..(278)
<223> OTHER INFORMATION: Motif name:P1BS
<220> FEATURE:
<221> NAME/KEY: misc_feature
<222> LOCATION: (395)..(399)
<223> OTHER INFORMATION: Motif name:ABRELATED1
<220> FEATURE:
<221> NAME/KEY: misc_feature
<222> LOCATION: (601)..(608)
<223> OTHER INFORMATION: Motif name:CACGCAATGMGH3
<220> FEATURE:
<221> NAME/KEY: misc_feature
<222> LOCATION: (797)..(801)
<223> OTHER INFORMATION: Motif name:ABRELATED1
<220> FEATURE:
<221> NAME/KEY: misc_feature
<222> LOCATION: (891)..(896)
<223> OTHER INFORMATION: Motif name:GT1Consensus
<220> FEATURE:
<221> NAME/KEY: misc_feature
<222> LOCATION: (917)..(923)
<223> OTHER INFORMATION: Motif name:TATABOX4
<220> FEATURE:
<221> NAME/KEY: misc_feature
<222> LOCATION: (956)..(995)
<223> OTHER INFORMATION: 5' untranslated region

<400> SEQUENCE: 18

```
caatcggtcg cgaaagactt gatctaggta gagatatact taattaaaat cgatgaatga    60
ccaagtcaat aaatcaagat tcaatgttct ttcgacgaat tctgttcatt ttgcggttgg   120
gatcatgcat tcatttaaaa taaaccatta ttgaatacgt tatggataat gatagtgatt   180
aattatccaa tgaggaagag atttggttgg attgttttgg agagtaataa taaaaaataa   240
aggcatgcaa tagaaggggc agaccaagtg gaatattctg tctaccacaa cgaagtttca   300
atcaaagata tcagaggtta atgtcttcca ataagcgacc aaaaatcttg attaataatt   360
aattatatcg cccaaagtca ctatgaactt gtgaacgtgt tattttggag acttttctca   420
cctaaataca tcgagatcgc cttgttagtt ggtacttggt aaacattatg ctctaatggc   480
tttggttgtt attgacgaac atacaatgta atgaatattt tctcaattga gttgtttcat   540
ttctaacaaa actagaaact aaaacaagga aggcgatgtt tctcacatga aatttacata   600
cacgcaatga aaccaaacc gactaaattt tgtgtttttt tcagggtgat ttttaagaac   660
attccttaat caatgggatc taaaaaagtc acttgcctaa gaaagtcacc gaaacttcac   720
attcaaagta actttatcct cttctcagct tttcacatta tgaacctccc gtgggaacaa   780
agacatttat accctacgt gagcttccaa gaagaaacca acaattttta agattttccc   840
ccattacatg tagattagtt ggcttcaagt ttctatggat gttccttctc ggaaatccat   900
aattctcttc ctttatatat aaaacttact cacaacacaa aacccatctc tcaaaacaat   960
caatttctct caaactgttt tactttctct ttgta                             995
```

<210> SEQ ID NO 19
<211> LENGTH: 959
<212> TYPE: DNA
<213> ORGANISM: Arabidopsis thaliana
<220> FEATURE:
<221> NAME/KEY: misc_feature
<222> LOCATION: (1)..(959)
<223> OTHER INFORMATION: Ceres Promoter YP2816
<220> FEATURE:
<221> NAME/KEY: misc_feature
<222> LOCATION: (180)..(190)
<223> OTHER INFORMATION: Motif name:TL1ATSAR
<220> FEATURE:

```
<221> NAME/KEY: misc_feature
<222> LOCATION: (538)..(544)
<223> OTHER INFORMATION: Motif name:ANAERO1CONSENSUS
<220> FEATURE:
<221> NAME/KEY: misc_feature
<222> LOCATION: (672)..(679)
<223> OTHER INFORMATION: Motif name:XYLAT
<220> FEATURE:
<221> NAME/KEY: misc_feature
<222> LOCATION: (761)..(767)
<223> OTHER INFORMATION: Motif name:TATABOXOSPAL
<220> FEATURE:
<221> NAME/KEY: misc_feature
<222> LOCATION: (798)..(959)
<223> OTHER INFORMATION: 5' untranslated region
<220> FEATURE:
<221> NAME/KEY: misc_feature
<222> LOCATION: (649)..(959)
<223> OTHER INFORMATION: Ceres Promoter PD3229
<220> FEATURE:
<221> NAME/KEY: misc_feature
<222> LOCATION: (130)..(797)
<223> OTHER INFORMATION: Ceres Promoter PD3243
<220> FEATURE:
<221> NAME/KEY: misc_feature
<222> LOCATION: (448)..(959)
<223> OTHER INFORMATION: Ceres Promoter PD3238

<400> SEQUENCE: 19
cagtcgtgtt tttgccgttt atggttttat aattttataa aatgatttat acttgttggt      60
ttttatttgt aattttttcct gtaagggga aatttatttt ttatacagct aataaatgat     120
aaaaactcga aaattgtgac tacagtggaa gagtttggtg gcagacattt acttgttgtc     180
tgaagaagaa attcaatgca atgactaatc tgaaattaca ctagaatcaa ataaagcttt     240
acctaatgta attaaatttc tacagagttg gtggcttatg aaagataatc taaggagatt     300
ttgatgctct gtattttcaa attttagatg ttggccataa agtaaaattt atttatactt     360
ccacactcaa tccccatttt cagtattact tcaagtcttc gacatacttt attctgtaag     420 ttttttttt ggcatcaaaa agtgtgaaaa taaaagtatc attttcttat tgaatgatga     480
atacttatga aaagaaaag caaactttat gacgaataaa gcctgaaact gtgttgtaaa     540
caaagtctaa aacgaatgat ttttatttc tcgtcaagta atcatttat ttttattgat      600 gatttttgat acttcacata atactttga tattaggcca gttaggaata aattttcaaa     660
tactttgatc tttcttgtt gaacttgagc ggttcgtacg aacatgcttt gatctttttg     720
catttactta tgaataaagc aaaaacttct aaactgtttc tatttaatag attggaactc     780
gagtcggtgt acattgaaaa aataaaccaa aatttaataa cagagattat ttgccttta     840 atacatatac acacacgcac atatctacct gcatcttctt cataatcatt cctaagaaat     900
tctctctctc acacactcaa gaacaagaca agagtcaaga aaaatcagcc atgcactga     959

<210> SEQ ID NO 20
<211> LENGTH: 993
<212> TYPE: DNA
<213> ORGANISM: Arabidopsis thaliana
<220> FEATURE:
<221> NAME/KEY: misc_feature
<222> LOCATION: (1)..(993)
<223> OTHER INFORMATION: Ceres Promoter YP2832
<220> FEATURE:
<221> NAME/KEY: misc_feature
<222> LOCATION: (175)..(181)
<223> OTHER INFORMATION: Motif name:MYBGAHV
<220> FEATURE:
<221> NAME/KEY: misc_feature
<222> LOCATION: (438)..(446)
<223> OTHER INFORMATION: Motif name:SURE2STPAT21
```

-continued

```
<220> FEATURE:
<221> NAME/KEY: misc_feature
<222> LOCATION: (480)..(489)
<223> OTHER INFORMATION: Motif name:CARGCW8GAT
<220> FEATURE:
<221> NAME/KEY: misc_feature
<222> LOCATION: (525)..(533)
<223> OTHER INFORMATION: Motif name:SURE2STPAT21
<220> FEATURE:
<221> NAME/KEY: misc_feature
<222> LOCATION: (529)..(538)
<223> OTHER INFORMATION: Motif name:CARGCW8GAT
<220> FEATURE:
<221> NAME/KEY: misc_feature
<222> LOCATION: (763)..(770)
<223> OTHER INFORMATION: Motif name:XYLAT
<220> FEATURE:
<221> NAME/KEY: misc_feature
<222> LOCATION: (816)..(822)
<223> OTHER INFORMATION: Motif name:BOXIIPCCHS
<220> FEATURE:
<221> NAME/KEY: misc_feature
<222> LOCATION: (816)..(823)
<223> OTHER INFORMATION: Motif name:LRENPCABE
<220> FEATURE:
<221> NAME/KEY: misc_feature
<222> LOCATION: (894)..(900)
<223> OTHER INFORMATION: Motif name:TATABOX2
<220> FEATURE:
<221> NAME/KEY: misc_feature
<222> LOCATION: (927)..(993)
<223> OTHER INFORMATION: 5' untranslated region
<220> FEATURE:
<221> NAME/KEY: misc_feature
<222> LOCATION: (595)..(993)
<223> OTHER INFORMATION: Ceres Promoter PD3300

<400> SEQUENCE: 20
tcaaaaaata aaaatttgag tcgttgctcg tcagattttta tgtcactaga cagcaacgaa      60
aacaagcaca taataatcaa aaccgtagca gaaaatgcca atcaaaggta aattatggtt     120
catggaggca atttgcaaac aatgattagg attgtgtcat actgtagaaa aaattaacaa     180
aacaattttt ttattattca ttgactcgaa ggttgaacaa gaaggtcgaa aaaataaaca     240
tctttacatg ggggttcata ttatttatgt acaaattgct accaaggaca aagatcacat     300
gctcatctac aacgataaga tcaatgaatt tgacagtata ttaataaatc atgcatctat     360
acataaataa aaactagtag gaactagtct agtcaaaaag tacagtatta tggacaagat     420
atgaaactag ctaggataat actaattgct gtagcttaag ccacttgaat gttgtccctc     480
attattatgt ccaaaaaatt caatgtagac aagaaaaaag aactaatact aatatatgtc     540
ttgccacgat tgttacttta atctcattt tcaaatatta tggtctcata tagccaaatc      600
tgtaattctt atattccagt acgtatggag agactcggga gagtcgaacc aagaacatgc     660
tcaggccttc tgagttgtga catagatagt acaaccaggc gaccgagaca aacaaaacca     720
tgttatttgt aatgaattat aatgatccaa tcttgaccac acacaaagaa aagtctgata     780
ataatgaaac aaatgagcat gcaaagtatg tgacgacgtg gcaaaaaatg agaaggttca     840
acgaagcaac aaaaagaagt atttcgtcgt ctttactccc atcaatatgt gactataaat     900
aaaaccatat agttaagtca cacttccatg tcaacgtgct tcaacctatg taaagctaaa     960
aaaaaaacac atcacacaaa agatctctac act                                  993

<210> SEQ ID NO 21
<211> LENGTH: 600
<212> TYPE: DNA
<213> ORGANISM: Arabidopsis thaliana
<220> FEATURE:
```

```
<221> NAME/KEY: misc_feature
<222> LOCATION: (1)..(600)
<223> OTHER INFORMATION: Ceres Promoter PD2995
<220> FEATURE:
<221> NAME/KEY: misc_feature
<222> LOCATION: (1)..(600)
<223> OTHER INFORMATION: Ceres Promoter PD2263
<220> FEATURE:
<221> NAME/KEY: misc_feature
<222> LOCATION: (365)..(574)
<223> OTHER INFORMATION: Intron
<220> FEATURE:
<221> NAME/KEY: misc_feature
<222> LOCATION: (1)..(10)
<223> OTHER INFORMATION: Motif name:CIACADIANLELHC
<220> FEATURE:
<221> NAME/KEY: misc_feature
<222> LOCATION: (3)..(11)
<223> OTHER INFORMATION: Motif name:EVENINGAT
<220> FEATURE:
<221> NAME/KEY: misc_feature
<222> LOCATION: (21)..(30)
<223> OTHER INFORMATION: Motif name:CARGCW8GAT
<220> FEATURE:
<221> NAME/KEY: misc_feature
<222> LOCATION: (103)..(109)
<223> OTHER INFORMATION: Motif name:ABRERATCAL
<220> FEATURE:
<221> NAME/KEY: misc_feature
<222> LOCATION: (125)..(131)
<223> OTHER INFORMATION: Motif name:RBCSCONSENSUS
<220> FEATURE:
<221> NAME/KEY: misc_feature
<222> LOCATION: (185)..(194)
<223> OTHER INFORMATION: Motif name:CIACADIANLELHC
<220> FEATURE:
<221> NAME/KEY: misc_feature
<222> LOCATION: (249)..(256)
<223> OTHER INFORMATION: Motif name:MYBPLANT
<220> FEATURE:
<221> NAME/KEY: misc_feature
<222> LOCATION: (298)..(301)
<223> OTHER INFORMATION: Transcription Start Site
<220> FEATURE:
<221> NAME/KEY: misc_feature
<222> LOCATION: (272)..(281)
<223> OTHER INFORMATION: Motif name:TATA Box
<220> FEATURE:
<221> NAME/KEY: misc_feature
<222> LOCATION: (304)..(364)
<223> OTHER INFORMATION: 5' untranslated region
<220> FEATURE:
<221> NAME/KEY: misc_feature
<222> LOCATION: (575)..(600)
<223> OTHER INFORMATION: 5' untranslated region
<220> FEATURE:
<221> NAME/KEY: misc_feature
<222> LOCATION: (1)..(365)
<223> OTHER INFORMATION: Ceres Promoter PD3048
<220> FEATURE:
<221> NAME/KEY: misc_feature
<222> LOCATION: (1)..(342)
<223> OTHER INFORMATION: Ceres Promoter PD3676
<220> FEATURE:
<221> NAME/KEY: misc_feature
<222> LOCATION: (1)..(306)
<223> OTHER INFORMATION: Ceres Promoter PD3182
<220> FEATURE:
<221> NAME/KEY: misc_feature
<222> LOCATION: (40)..(600)
<223> OTHER INFORMATION: Ceres Promoter PD2926
<220> FEATURE:
<221> NAME/KEY: misc_feature
<222> LOCATION: (101)..(600)
<223> OTHER INFORMATION: Ceres Promoter PD3345
<220> FEATURE:
<221> NAME/KEY: misc_feature
<222> LOCATION: (176)..(600)
<223> OTHER INFORMATION: Ceres Promoter PD3503
```

<400> SEQUENCE: 21

```
caaaaatatc taatttgcag cattaatttg agtaccgata actattatta taatcgtcgt      60
gattcgcaat cttcttcatt agatgctgtc aagttgtact cgcacgcggt ggtccagtga     120
agcaaatcca acggtttaaa accttcttac atttctagat ctaatctgaa ccgtcagata     180
tctagatctc attgtctgaa cacagttaga tgaaactggg aatgaatctg acgaaaatta     240
cgatcttaca ccaaccccct cgacgagctc gtatatataa agcttatacg ctcctccttc     300
accttcgtac tactactacc accacatttc tttagctcaa ccttcattac taatctcctt     360
ttaaggtatg ttcacttttc ttcgattcat actttctcaa gattcctgca tttctgtaga     420
atttgaacca agtgtcgatt tttgtttgag agaagtgttg atttatagat ctggttattg     480
aatctagatt ccaatttta attgattcga gtttgttatg tgtgtttata ctacttctca     540
ttgatcttgt ttgatttctc tgctctgtat taggtttctt tcgtgaatca gatcggaaaa     600
```

<210> SEQ ID NO 22
<211> LENGTH: 900
<212> TYPE: DNA
<213> ORGANISM: Arabidopsis thaliana
<220> FEATURE:
<221> NAME/KEY: misc_feature
<222> LOCATION: (1)..(900)
<223> OTHER INFORMATION: Ceres Promoter PD2999
<220> FEATURE:
<221> NAME/KEY: misc_feature
<222> LOCATION: (1)..(900)
<223> OTHER INFORMATION: Ceres Promoter PD2258
<220> FEATURE:
<221> NAME/KEY: misc_feature
<222> LOCATION: (393)..(898)
<223> OTHER INFORMATION: Intron
<220> FEATURE:
<221> NAME/KEY: misc_feature
<222> LOCATION: (106)..(113)
<223> OTHER INFORMATION: Motif name:MYBPLANT
<220> FEATURE:
<221> NAME/KEY: misc_feature
<222> LOCATION: (160)..(900)
<223> OTHER INFORMATION: Ceres Promoter PD3266
<220> FEATURE:
<221> NAME/KEY: misc_feature
<222> LOCATION: (192)..(199)
<223> OTHER INFORMATION: Motif name:XYLAT
<220> FEATURE:
<221> NAME/KEY: misc_feature
<222> LOCATION: (237)..(243)
<223> OTHER INFORMATION: Motif name:ABRERATCAL
<220> FEATURE:
<221> NAME/KEY: misc_feature
<222> LOCATION: (285)..(292)
<223> OTHER INFORMATION: Motif name:UP2ATMSD
<220> FEATURE:
<221> NAME/KEY: misc_feature
<222> LOCATION: (301)..(900)
<223> OTHER INFORMATION: Ceres Promoter PD2929
<220> FEATURE:
<221> NAME/KEY: misc_feature
<222> LOCATION: (305)..(310)
<223> OTHER INFORMATION: Motif name:TATA Box
<220> FEATURE:
<221> NAME/KEY: misc_feature
<222> LOCATION: (339)..(392)
<223> OTHER INFORMATION: 5' untranslated region
<220> FEATURE:
<221> NAME/KEY: misc_feature
<222> LOCATION: (899)..(900)
<223> OTHER INFORMATION: 5' untranslated region
<220> FEATURE:
<221> NAME/KEY: misc_feature
<222> LOCATION: (1)..(339)

<223> OTHER INFORMATION: Ceres Promoter PD3183
<220> FEATURE:
<221> NAME/KEY: misc_feature
<222> LOCATION: (281)..(900)
<223> OTHER INFORMATION: Ceres Promoter PD3240

<400> SEQUENCE: 22

```
atagatttat caaagccaac tcatgacggc tagggttttc cgtcaccttt tcgatcatca      60
agagagtttt tttataaaaa aatttataca attatacaat ttcttaacca aacaacacat     120
aattataagc tatttaacat ttcaaattga aaaaaaaaat gtatgagaat tttgtggatc     180
cattttttgta attctttgtt gggtaaattc acaaccaaaa aaatagaaag gcccaaaacg    240
cgtaagggca aattagtaaa agtagaacca caaagagaaa gcgaaaaccc tagacacctc     300
gtagctataa gtaccctcga gtcgaccagg attagggtgc gctctcatat ttctcacatt    360
ttcgtagccg caagactcct ttcagattct tacttgcagg ttagatattt tctctcttta    420
gtgtctccga tcttcatctt cttatgatta ttgtagctgt ttagggttta gattcttagt    480
tttagctcta tattgactgt gattatcgct tattctttgc tgttgttata ctgcttttga    540
ttctctagct ttagatccgt ttactcgtcg atcaatattg ttcctattga gtctgatgta    600
taatcctctg attaattgat agcgtttagt tttgatatcg tcttcgcatg ttttttatca    660
tgtcgatctg tatctgctct ggttatagtt gattctgatg tatttggttg gtgatgttcc    720
ttagatttga tacctgtt gtctcgtggt ttgatatgat agctcaactg gtgatatgtg    780
gttttgtttc agtggatctg tgtttgatta tattgttgac gttttggttg ttgtatagtt    840
gatggttgat gtattttgt tgattctgat gtttcgattt ttgttttgt tttgacagct    900
```

<210> SEQ ID NO 23
<211> LENGTH: 1300
<212> TYPE: DNA
<213> ORGANISM: Oryza sativa
<220> FEATURE:
<221> NAME/KEY: misc_feature
<222> LOCATION: (1)..(1300)
<223> OTHER INFORMATION: Ceres Promoter PD3141
<220> FEATURE:
<221> NAME/KEY: misc_feature
<222> LOCATION: (576)..(1289)
<223> OTHER INFORMATION: Intron
<220> FEATURE:
<221> NAME/KEY: misc_feature
<222> LOCATION: (24)..(31)
<223> OTHER INFORMATION: Motif name:MYBPLANT
<220> FEATURE:
<221> NAME/KEY: misc_feature
<222> LOCATION: (122)..(129)
<223> OTHER INFORMATION: Motif name:MYBPLANT
<220> FEATURE:
<221> NAME/KEY: misc_feature
<222> LOCATION: (158)..(165)
<223> OTHER INFORMATION: Motif name:MYBPLANT
<220> FEATURE:
<221> NAME/KEY: misc_feature
<222> LOCATION: (185)..(196)
<223> OTHER INFORMATION: Motif name:ACIIPVPAL2
<220> FEATURE:
<221> NAME/KEY: misc_feature
<222> LOCATION: (188)..(195)
<223> OTHER INFORMATION: Motif name:MYBPLANT
<220> FEATURE:
<221> NAME/KEY: misc_feature
<222> LOCATION: (300)..(306)
<223> OTHER INFORMATION: Motif name:ABRERATCAL
<220> FEATURE:
<221> NAME/KEY: misc_feature
<222> LOCATION: (427)..(434)
<223> OTHER INFORMATION: Motif name:TATABox
<220> FEATURE:
<221> NAME/KEY: misc_feature
<222> LOCATION: (457)..(575)
<223> OTHER INFORMATION: Motif name:5'UTR
<220> FEATURE:
<221> NAME/KEY: misc_feature
<222> LOCATION: (1289)..(1300)
<223> OTHER INFORMATION: Motif name:5'UTR
<220> FEATURE:
<221> NAME/KEY: misc_feature
<222> LOCATION: (151)..(1300)
<223> OTHER INFORMATION: Ceres Promoter PD3584

<400> SEQUENCE: 23

```
tagctcacat catcaaaagc aatggttggt gatgtggaga aaaaattttc tatagcaaga    60
gaaaaaaaaa cacactaaaa tccggaaaaa caaaatgaga aagtagtgga ggtggagaga   120
tgtttggtga ggcgggcgtg ggccccaccc aacatggggt tggtggccac tggccacggc   180
cacgggggt tggtggacgc ggggggcgtgg gccccacctc cccagcgtct gtccgtccgg   240
cgggtgagaa aagtttcggg cggggtcagc gacggttcac tggctgtgtg tgcggtcctc   300
acgtgctcac ccccgggga gaaatacttt tcgcacgcga atcctacccg cacccacggt   360
ggggtgggcc ccactccact cccccgcgcg tcgtctccta cctcccgatc cgcacccgac   420
gcgcgctata aataggaggc gcgagcgcat tccggaggcc accccgtgc agaatcacac    480
acgccggact ctccccttct ctctgtctcg ctccttcgtt cgctcgcttt atcccccccg   540
aataaaggcg agaagccgca gcggcggacg aagaaggtga gctctctcgt ctcgcctcgt   600
cttcttcttg ctcgtgagat cctcactcct ctcggggatt ttttttttctc tgttggggtt   660
tgggtttggg ggtagatctg ggttgggcgc tcttcgatct gaggagcgcg aggtttggtg   720
gattggagat ctggggacta ggggttagtg attgtttgtt tgtttcgttt ttcggtcgcg   780
gaagtgggag gggaaagcgg ttgggggggat attcttgctt ttttttgttta atctttgatt   840
gtgcgtgtat ggagttctgg attagcagaa aaaagggtcc gatctttttt ggtttatggg   900
ggagaacagg ctaggctaga tctagcgttg gtggatccaa tttttaaattg caaaattttg   960
tcagtactta gctgtcggct gcagtagatc tgaagaatgg atctctgttt tgtgattaat  1020
tttctctgtt ttttttcctt tttttgttct gtggtctact acaccaatag agaattcgaa  1080
tttgctctcc tctttctttc agcaagtagg agtaaaatca cttagtacta gtatcatttt  1140
aggtgcaaaa atcgactctt tttctcttgg atacaccagt tcgtcctcat cttggctgca  1200
acgaatgaat ggattgatca tctttagaaa ctgtctgcac aaaatcgagt atttttttttt  1260
ctgatggctt gcaaccgatg catgcagagg gcagatagaa                        1300
```

<210> SEQ ID NO 24
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter YP2680
<220> FEATURE:
<221> NAME/KEY: misc_feature
<222> LOCATION: (359)..(365)
<223> OTHER INFORMATION: Motif name:-300CORE
<220> FEATURE:
<221> NAME/KEY: misc_feature
<222> LOCATION: (466)..(472)
<223> OTHER INFORMATION: Motif name:ANAERO1CONSENSUS
<220> FEATURE:
<221> NAME/KEY: misc_feature
<222> LOCATION: (567)..(574)

```
<223> OTHER INFORMATION: Motif name:NRRBNEXTA
<220> FEATURE:
<221> NAME/KEY: misc_feature
<222> LOCATION: (709)..(716)
<223> OTHER INFORMATION: Motif name:EMHVCHORD
<220> FEATURE:
<221> NAME/KEY: misc_feature
<222> LOCATION: (709)..(715)
<223> OTHER INFORMATION: Motif name:-300CORE
<220> FEATURE:
<221> NAME/KEY: misc_feature
<222> LOCATION: (842)..(849)
<223> OTHER INFORMATION: Motif name:AUXRETGA1GMGH3
<220> FEATURE:
<221> NAME/KEY: misc_feature
<222> LOCATION: (942)..(950)
<223> OTHER INFORMATION: Motif name:TATABOX4
<220> FEATURE:
<221> NAME/KEY: misc_feature
<222> LOCATION: (975)..(1000)
<223> OTHER INFORMATION: 5' untranslated region

<400> SEQUENCE: 24
gtctaccgac ttttccaccg tccatccttc gacgatggtt ctttctaaat gaccttctca    60
gttttttcct gtcatgcgta ttattattat tagttaataa ggctccacta ctactcggaa   120
agtccgagta caaataatat gacaataatg tcaaacttat tcttagtatt ggtttaaaag   180
aaggattcaa caagagtact taatcacgtc tcataattac cactttcatc caaacatggt   240
cattactata tgacatgatc gtgttacatt aatttggaaa gtagtatatg tcttttttcct   300 aaaagtttat gtttagattt ttgatcacta agaatataat gtcatatata ttattaaccct  360 ttacacctaa atgttatatt aattacttga atgataaaac ggaaaatatc gaaagtttag   420
gctaggtctc tctagcatct ctagtgtatt tatttagcaa tcccaaaaca aaattgtgtt   480
ttctacaatt ttagtattag attaccaaaa ttgttgtata tagtctggtg attccgtttt   540
gatggtcgag atcgaaagaa gcaagcatcc actatgtggt cgtcacatgc gaatatttct   600
aagtatacaa ccatctatcg aaagtttcga acaacccaa atataatagt aataaattct    660
gagaattctc ctattttttta ttgatatgaa aaaagcagta aaatattatg taaagtagag  720
aggaaccaaa attaaaacgt gcagatttat taaaagaata aagtgggatc caaaagtca   780 gcgtgaaaca tgtgatacga taacgaca cggtcctatg actaagtcca ctccaatcca    840
gtgacgtaaa cagcaccatc acccatagct tcctgtgacg cacatcctta cgtaaccatc   900
gttgacgcta gactttcctc tctgatctct cttttcttcat gtatatataa caaaaccttc   960
ctttcctaat tggtatctat ctttaaaaac atacttgaaa                        1000

<210> SEQ ID NO 25
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PD3147
<220> FEATURE:
<221> NAME/KEY: misc_feature
<222> LOCATION: (1)..(1000)
<223> OTHER INFORMATION: Ceres Promoter YP2663
<220> FEATURE:
<221> NAME/KEY: misc_feature
<222> LOCATION: (203)..(212)
<223> OTHER INFORMATION: Motif name:MARTBOX
<220> FEATURE:
<221> NAME/KEY: misc_feature
<222> LOCATION: (347)..(355)
<223> OTHER INFORMATION: Motif name:TELOBOXATEEF1AA1
```

<220> FEATURE:
<221> NAME/KEY: misc_feature
<222> LOCATION: (392)..(397)
<223> OTHER INFORMATION: Motif name:IBOXCORENT
<220> FEATURE:
<221> NAME/KEY: misc_feature
<222> LOCATION: (576)..(583)
<223> OTHER INFORMATION: Motif name:INRNTPSADB
<220> FEATURE:
<221> NAME/KEY: misc_feature
<222> LOCATION: (613)..(622)
<223> OTHER INFORMATION: Motif name:MARTBOX
<220> FEATURE:
<221> NAME/KEY: misc_feature
<222> LOCATION: (792)..(799)
<223> OTHER INFORMATION: Motif name:E2FCONSENSUS
<220> FEATURE:
<221> NAME/KEY: misc_feature
<222> LOCATION: (804)..(809)
<223> OTHER INFORMATION: Motif name:IBOXCORENT
<220> FEATURE:
<221> NAME/KEY: misc_feature
<222> LOCATION: (823)..(828)
<223> OTHER INFORMATION: Motif name:IBOXCORENT
<220> FEATURE:
<221> NAME/KEY: misc_feature
<222> LOCATION: (698)..(704)
<223> OTHER INFORMATION: Motif name:SORLREP3AT
<220> FEATURE:
<221> NAME/KEY: misc_feature
<222> LOCATION: (941)..(1000)
<223> OTHER INFORMATION: 5' untranslated region
<220> FEATURE:
<221> NAME/KEY: misc_feature
<222> LOCATION: (501)..(1000)
<223> OTHER INFORMATION: Ceres Promoter PD3721

<400> SEQUENCE: 25

```
agtaatggtt tacacattga ttattctata agaaacatct agaaagaaa aaaaggaaa       60 aaaaacatct agaaatatat cagaacttct ttcacaaaag aataatatat atcagaactg    120
cgtgttatta attcaacgag ttcaaacttc aaagtatgat gtggtaacac aaccaaattc    180
tcctctcgga tataattaga ccaaaaaaaa aaagacgaaa tattttttgct ataaacaata    240 tatatatggg taaatgtgaa gaaattttgtt cttctgcca ggaaatagac agttaataca    300
ttgaaaaaat ggtaaaactt taaagaaaag catatcttaa gagatgaaac cctaattaag    360
gtgttgagac ttcagagaca gatcaagaga tcttatcaga agatatctgt gaagcatttc    420
aaacaaacat tacaaaaaat gtagcctcct tccggcggaa tggtagaagg agttgtaatt    480
ctgctaatgt ttattttggt catatataga tttaattctt tgatattgca aactcatgat    540
cccattttct tattatgtgg ttaaccaata aaagactcaa ttttgcagtc ttactaatca    600
ggactatttg ccaaaaaaaa aactaatcag gactaaaaaa ctacatctct ttttttttt    660 gctacatata tatatatata tgattatttt cagtgtatat ataatatgta tagatattaa    720
aaataaataa aagataagtc gtgtgtagtc cacatatctt gaacatcaaa atgacaaaac    780
tattaaaatc cgcggcaaaa tctcttatcc agtgacatgt tacttatcaa ccaatcacaa    840
cacgccacct catcacccca agaccacttc tcttatcttc ctctccctcc actaatcccc    900
tcaagaatct aaagctcctc ccataagtct tctctccaca cttcacccaa aactccagaa    960
ccctagaatt cgaaatctcc aaagaacccg acaaagcgcc                        1000
```

<210> SEQ ID NO 26
<211> LENGTH: 1000
<212> TYPE: DNA
<213> ORGANISM: Arabidopsis thaliana
<220> FEATURE:

```
<221> NAME/KEY: misc_feature
<222> LOCATION: (1)..(1000)
<223> OTHER INFORMATION: Ceres Promoter PT0822
<220> FEATURE:
<221> NAME/KEY: misc_feature
<222> LOCATION: (601)..(1000)
<223> OTHER INFORMATION: Ceres Promoter PD3389
<220> FEATURE:
<221> NAME/KEY: misc_feature
<222> LOCATION: (645)..(649)
<223> OTHER INFORMATION: Motif name:ROOTMOTIFTAPOX1
<220> FEATURE:
<221> NAME/KEY: misc_feature
<222> LOCATION: (654)..(661)
<223> OTHER INFORMATION: Motif name:E2FCONSENSUS
<220> FEATURE:
<221> NAME/KEY: misc_feature
<222> LOCATION: (657)..(663)
<223> OTHER INFORMATION: Motif name:LEAFYATAG
<220> FEATURE:
<221> NAME/KEY: misc_feature
<222> LOCATION: (720)..(729)
<223> OTHER INFORMATION: Motif name:CARGCW8GAT
<220> FEATURE:
<221> NAME/KEY: misc_feature
<222> LOCATION: (817)..(821)
<223> OTHER INFORMATION: Motif name:ROOTMOTIFTAPOX1
<220> FEATURE:
<221> NAME/KEY: misc_feature
<222> LOCATION: (823)..(840)
<223> OTHER INFORMATION: Motif name:AGL2ATCONSENSUS
<220> FEATURE:
<221> NAME/KEY: misc_feature
<222> LOCATION: (827)..(836)
<223> OTHER INFORMATION: Motif name:CARGATCONSENSUS
<220> FEATURE:
<221> NAME/KEY: misc_feature
<222> LOCATION: (785)..(790)
<223> OTHER INFORMATION: Motif name:TATABOX5
<220> FEATURE:
<221> NAME/KEY: misc_feature
<222> LOCATION: (848)..(1000)
<223> OTHER INFORMATION: 5' untranslated region
<220> FEATURE:
<221> NAME/KEY: misc_feature
<222> LOCATION: (601)..(1000)
<223> OTHER INFORMATION: Ceres Promoter PD3389

<400> SEQUENCE: 26
ccaccaacat acattagaat ctaatgtaat tacatcatca atcatagacc taatgaatat      60
ttaataccac acagtttaaa cattgctatt aaagtttgaa aagattatac tttagtaaaa     120
taatgttttc aaacttgtat tcaattatac tacgtaagca gtgatccaat tattacgaac     180
ataatacttt tccaaatcaa aatttttgttt ttgttcacct taccatcagt ttcataatag     240
aaatattata tatatacaac acaaacaaat gaatgagaaa tgttttttcta ttattatgac     300 tttatttaa gattcaaaag aacgaagaag agttatatat atgcttgttt gtttcaggac     360
aaatacaata aataagtgga taagaaaacc acaaaccttg aactagcctg aaatgtgtga     420
accaagctat acaaactgta cgtgattctg catcgtggaa gtcacaaaca gacttctgac     480
ttctgctaaa gataaaactc actgtttgca agcaatttag tataaatatg aagcattgac     540
ctaccaagat cgacacaatc acacagtttc ttcttaatta aacctagcta tttttgtctt     600
tagcagaagt cagaaagcta gttttgtatt tttcttattt cttaaatata tggcggccaa     660
tgttatgaga cggtttatga tttaaagata cacaatggac ccacgacgtt gccataatac     720
aattattagg ctgttaatta acgtgatcgt tacgtttgct acaaactagc tagttgtgtc     780
ttctttattt tagtagataa gtataagagt ctaaaaaatat tacaacccaa taatggttac     840
attcatggtc gacttagaag atgaaagttg atttcttaaa aaaaaaacac gcacaataaa     900
```
taaaccacca attcacaaat acaagaaatt taataacctc gagcagttac cctatttaaa     960 tccctctag ccttgttttc cttctcacac ctatgaagca                            1000

<210> SEQ ID NO 27
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: -300CORE motif

<400> SEQUENCE: 27 tgtaaag                                                               7

<210> SEQ ID NO 28
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: ABREATCONSENSUS motif

<400> SEQUENCE: 28 yacgtggc                                                              8

<210> SEQ ID NO 29
<211> LENGTH: 10
<212> TYPE: DNA
<213> ORGANISM: Artifical Sequence
<220> FEATURE:
<221> NAME/KEY: misc_feature
<222> LOCATION: (1)..(10)
<223> OTHER INFORMATION: ABREATRD22 motif

<400> SEQUENCE: 29 ryacgtggyr                                                            10

<210> SEQ ID NO 30
<211> LENGTH: 5
<212> TYPE: DNA
<213> ORGANISM: Artifical Sequence
<220> FEATURE:
<221> NAME/KEY: misc_feature
<222> LOCATION: (1)..(5)
<223> OTHER INFORMATION: ABRELATERD1 motif

<400> SEQUENCE: 30 acgtg                                                                 5

<210> SEQ ID NO 31
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: ABREMOTIFAOSOSEM motif

<400> SEQUENCE: 31 tacgtgtc                                                              8

<210> SEQ ID NO 32
<211> LENGTH: 7
<212> TYPE: DNA

```
<213> ORGANISM: Artifical Sequence
<220> FEATURE:
<221> NAME/KEY: misc_feature
<222> LOCATION: (1)..(7)
<223> OTHER INFORMATION: ABRERATCAL motif

<400> SEQUENCE: 32 macgygb                                                                   7

<210> SEQ ID NO 33
<211> LENGTH: 6
<212> TYPE: DNA
<213> ORGANISM: Artifical Sequence
<220> FEATURE:
<221> NAME/KEY: misc_feature
<222> LOCATION: (1)..(6)
<223> OTHER INFORMATION: ACGTCBOX motif

<400> SEQUENCE: 33 gacgtc                                                                    6

<210> SEQ ID NO 34
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: ACGTOSGLUB1 motif

<400> SEQUENCE: 34 gtacgtg                                                                   7

<210> SEQ ID NO 35
<211> LENGTH: 6
<212> TYPE: DNA
<213> ORGANISM: Artifical Sequence
<220> FEATURE:
<221> NAME/KEY: misc_feature
<222> LOCATION: (1)..(6)
<223> OTHER INFORMATION: ACGTTBOX motif

<400> SEQUENCE: 35 aacgtt                                                                    6

<210> SEQ ID NO 36
<211> LENGTH: 12
<212> TYPE: DNA
<213> ORGANISM: Artifical Sequence
<220> FEATURE:
<221> NAME/KEY: misc_feature
<222> LOCATION: (1)..(12)
<223> OTHER INFORMATION: ACIIPVPAL2 motif

<400> SEQUENCE: 36
ccaccaaccc cc                                                            12

<210> SEQ ID NO 37
<211> LENGTH: 18
<212> TYPE: DNA
<213> ORGANISM: Artifical Sequence
<220> FEATURE:
<221> NAME/KEY: misc_feature
<222> LOCATION: (1)..(18)
<223> OTHER INFORMATION: AGL2ATCONSENSUS motif
<220> FEATURE:
<221> NAME/KEY: misc_feature
<222> LOCATION: (1)..(1)
<223> OTHER INFORMATION: n is a, c, t, g, unknown, or other
```

```
<220> FEATURE:
<221> NAME/KEY: misc_feature
<222> LOCATION: (2)..(2)
<223> OTHER INFORMATION: n is a, c, t, g, unknown, or other
<220> FEATURE:
<221> NAME/KEY: misc_feature
<222> LOCATION: (4)..(4)
<223> OTHER INFORMATION: n is a, c, t, g, unknown, or other
<220> FEATURE:
<221> NAME/KEY: misc_feature
<222> LOCATION: (18)..(18)
<223> OTHER INFORMATION: n is a, c, t, g, unknown, or other

<400> SEQUENCE: 37
nnwnccawww wtrgwwan                                              18

<210> SEQ ID NO 38
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: AMYBOX2 motif

<400> SEQUENCE: 38 tatccat                                                          7

<210> SEQ ID NO 39
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: ANAERO1CONSENSUS motif

<400> SEQUENCE: 39 aaacaaa                                                          7

<210> SEQ ID NO 40
<211> LENGTH: 11
<212> TYPE: DNA
<213> ORGANISM: Artifical Sequence
<220> FEATURE:
<221> NAME/KEY: misc_feature
<222> LOCATION: (1)..(11)
<223> OTHER INFORMATION: ARE1 motif
<220> FEATURE:
<221> NAME/KEY: misc_feature
<222> LOCATION: (7)..(7)
<223> OTHER INFORMATION: n is a, c, t, g, unknown, or other
<220> FEATURE:
<221> NAME/KEY: misc_feature
<222> LOCATION: (8)..(8)
<223> OTHER INFORMATION: n is a, c, t, g, unknown, or other
<220> FEATURE:
<221> NAME/KEY: misc_feature
<222> LOCATION: (9)..(9)
<223> OTHER INFORMATION: n is a, c, t, g, unknown, or other

<400> SEQUENCE: 40
rgtgacnnng c                                                     11

<210> SEQ ID NO 41
<211> LENGTH: 9
<212> TYPE: DNA
<213> ORGANISM: Artifical Sequence
<220> FEATURE:
<221> NAME/KEY: misc_feature
<222> LOCATION: (1)..(9)
```

```
<223> OTHER INFORMATION: ATHB6COREAT motif

<400> SEQUENCE: 41 caattatta                                                                  9

<210> SEQ ID NO 42
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: AUXRETGA1GMGH3 motif

<400> SEQUENCE: 42 tgacgtaa                                                                   8

<210> SEQ ID NO 43
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: BOXIIPCCHS motif

<400> SEQUENCE: 43 acgtggc                                                                    7

<210> SEQ ID NO 44
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: BOXLCOREDCPAL motif

<400> SEQUENCE: 44 accwwcc                                                                    7

<210> SEQ ID NO 45
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: CACGCAATGMGH3 motif

<400> SEQUENCE: 45 cacgcaat                                                                   8

<210> SEQ ID NO 46
<211> LENGTH: 10
<212> TYPE: DNA
<213> ORGANISM: Artifical Sequence
<220> FEATURE:
<221> NAME/KEY: misc_feature
<222> LOCATION: (1)..(10)
<223> OTHER INFORMATION: CARGATCONSENSUS motif

<400> SEQUENCE: 46 ccwwwwwwgg                                                                10

<210> SEQ ID NO 47
<211> LENGTH: 10
```

```
<212> TYPE: DNA
<213> ORGANISM: Artifical Sequence
<220> FEATURE:
<221> NAME/KEY: misc_feature
<222> LOCATION: (1)..(10)
<223> OTHER INFORMATION: Ceres Seed Line no. CW8
<220> FEATURE:
<221> NAME/KEY: misc_feature
<222> LOCATION: (1)..(10)
<223> OTHER INFORMATION: CARGCW8GAT motif

<400> SEQUENCE: 47 cwwwwwwwwg                                                                    10

<210> SEQ ID NO 48
<211> LENGTH: 10
<212> TYPE: DNA
<213> ORGANISM: Artifical Sequence
<220> FEATURE:
<221> NAME/KEY: misc_feature
<222> LOCATION: (1)..(10)
<223> OTHER INFORMATION: CIACADIANLELHC motif
<220> FEATURE:
<221> NAME/KEY: misc_feature
<222> LOCATION: (4)..(4)
<223> OTHER INFORMATION: n is a, c, t, g, unknown, or other
<220> FEATURE:
<221> NAME/KEY: misc_feature
<222> LOCATION: (5)..(5)
<223> OTHER INFORMATION: n is a, c, t, g, unknown, or other
<220> FEATURE:
<221> NAME/KEY: misc_feature
<222> LOCATION: (6)..(6)
<223> OTHER INFORMATION: n is a, c, t, g, unknown, or other
<220> FEATURE:
<221> NAME/KEY: misc_feature
<222> LOCATION: (7)..(7)
<223> OTHER INFORMATION: n is a, c, t, g, unknown, or other

<400> SEQUENCE: 48 caannnnatc                                                                    10

<210> SEQ ID NO 49
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: DPBFCOREDCDC3 motif
<220> FEATURE:
<221> NAME/KEY: misc_feature
<222> LOCATION: (5)..(5)
<223> OTHER INFORMATION: n is a, c, t, g, unknown, or other
<220> FEATURE:
<221> NAME/KEY: misc_feature
<222> LOCATION: (6)..(6)
<223> OTHER INFORMATION: n is a, c, t, g, unknown, or other

<400> SEQUENCE: 49 acacnng                                                                        7

<210> SEQ ID NO 50
<211> LENGTH: 6
<212> TYPE: DNA
<213> ORGANISM: Artifical Sequence
<220> FEATURE:
<221> NAME/KEY: misc_feature
<222> LOCATION: (1)..(6)
<223> OTHER INFORMATION: DRE2COREZMRAB17 motif

<400> SEQUENCE: 50
``` accgac 6

<210> SEQ ID NO 51
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: E2FCONSENSUS motif

<400> SEQUENCE: 51 wttsscss 8

<210> SEQ ID NO 52
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: EMHVCHORD motif

<400> SEQUENCE: 52 tgtaaagt 8

<210> SEQ ID NO 53
<211> LENGTH: 9
<212> TYPE: DNA
<213> ORGANISM: Artifical Sequence
<220> FEATURE:
<221> NAME/KEY: misc_feature
<222> LOCATION: (1)..(9)
<223> OTHER INFORMATION: EVENINGAT motif

<400> SEQUENCE: 53 aaaatatct 9

<210> SEQ ID NO 54
<211> LENGTH: 9
<212> TYPE: DNA
<213> ORGANISM: Artifical Sequence
<220> FEATURE:
<221> NAME/KEY: misc_feature
<222> LOCATION: (1)..(9)
<223> OTHER INFORMATION: GLMHVCHORD motif

<400> SEQUENCE: 54 rtgastcat 9

<210> SEQ ID NO 55
<211> LENGTH: 6
<212> TYPE: DNA
<213> ORGANISM: Artifical Sequence
<220> FEATURE:
<221> NAME/KEY: misc_feature
<222> LOCATION: (1)..(6)
<223> OTHER INFORMATION: GT1 motif

<400> SEQUENCE: 55 grwaaw 6

<210> SEQ ID NO 56
<211> LENGTH: 6
<212> TYPE: DNA
<213> ORGANISM: Artifical Sequence
<220> FEATURE:
<221> NAME/KEY: misc_feature

```
<222> LOCATION: (1)..(6)
<223> OTHER INFORMATION: GT1GMSCAM4 motif

<400> SEQUENCE: 56 gaaaaa                                                              6

<210> SEQ ID NO 57
<211> LENGTH: 9
<212> TYPE: DNA
<213> ORGANISM: Artifical Sequence
<220> FEATURE:
<221> NAME/KEY: misc_feature
<222> LOCATION: (1)..(9)
<223> OTHER INFORMATION: HDZIP2ATATHB2 motif

<400> SEQUENCE: 57 taatmatta                                                           9

<210> SEQ ID NO 58
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: IBOXCORENT motif

<400> SEQUENCE: 58 gataagr                                                             7

<210> SEQ ID NO 59
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: INRNTPSADB motif
<220> FEATURE:
<221> NAME/KEY: misc_feature
<222> LOCATION: (5)..(5)
<223> OTHER INFORMATION: n is a, c, t, g, unknown, or other

<400> SEQUENCE: 59 ytcantyy                                                            8

<210> SEQ ID NO 60
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: LEAFYATAG motif

<400> SEQUENCE: 60 ccaatgt                                                             7

<210> SEQ ID NO 61
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: LRENPCABE motif

<400> SEQUENCE: 61
``` acgtggca                                                          8

<210> SEQ ID NO 62
<211> LENGTH: 10
<212> TYPE: DNA
<213> ORGANISM: Artifical Sequence
<220> FEATURE:
<221> NAME/KEY: misc_feature
<222> LOCATION: (1)..(10)
<223> OTHER INFORMATION: MARTBOX motif

<400> SEQUENCE: 62 ttwtwttwtt                                                        10

<210> SEQ ID NO 63
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: MYBGAHV motif

<400> SEQUENCE: 63 taacaaa                                                           7

<210> SEQ ID NO 64
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: MYBPLANT motif

<400> SEQUENCE: 64 maccwamc                                                          8

<210> SEQ ID NO 65
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: NRRBNEXTA motif

<400> SEQUENCE: 65 tagtggat                                                          8

<210> SEQ ID NO 66
<211> LENGTH: 10
<212> TYPE: DNA
<213> ORGANISM: Artifical Sequence
<220> FEATURE:
<221> NAME/KEY: misc_feature
<222> LOCATION: (1)..(10)
<223> OTHER INFORMATION: O2F3BE2S1 motif

<400> SEQUENCE: 66
tccacgtact                                                        10

<210> SEQ ID NO 67
<211> LENGTH: 8
<212> TYPE: DNA
<213> ORGANISM: Artifical Sequence
<220> FEATURE:
<221> NAME/KEY: misc_feature

```
<222> LOCATION: (1)..(8)
<223> OTHER INFORMATION: P1BS motif
<220> FEATURE:
<221> NAME/KEY: misc_feature
<222> LOCATION: (2)..(2)
<223> OTHER INFORMATION: n is a, c, t, g, unknown, or other
<220> FEATURE:
<221> NAME/KEY: misc_feature
<222> LOCATION: (7)..(7)
<223> OTHER INFORMATION: n is a, c, t, g, unknown, or other

<400> SEQUENCE: 67 gnatatnc                                                                    8

<210> SEQ ID NO 68
<211> LENGTH: 24
<212> TYPE: DNA
<213> ORGANISM: Artifical Sequence
<220> FEATURE:
<221> NAME/KEY: misc_feature
<222> LOCATION: (1)..(24)
<223> OTHER INFORMATION: PRECONSCRHSP70A motif
<220> FEATURE:
<221> NAME/KEY: misc_feature
<222> LOCATION: (6)..(6)
<223> OTHER INFORMATION: n is a, c, t, g, unknown, or other
<220> FEATURE:
<221> NAME/KEY: misc_feature
<222> LOCATION: (8)..(8)
<223> OTHER INFORMATION: n is a, c, t, g, unknown, or other
<220> FEATURE:
<221> NAME/KEY: misc_feature
<222> LOCATION: (9)..(9)
<223> OTHER INFORMATION: n is a, c, t, g, unknown, or other
<220> FEATURE:
<221> NAME/KEY: misc_feature
<222> LOCATION: (10)..(10)
<223> OTHER INFORMATION: n is a, c, t, g, unknown, or other
<220> FEATURE:
<221> NAME/KEY: misc_feature
<222> LOCATION: (11)..(11)
<223> OTHER INFORMATION: n is a, c, t, g, unknown, or other
<220> FEATURE:
<221> NAME/KEY: misc_feature
<222> LOCATION: (12)..(12)
<223> OTHER INFORMATION: n is a, c, t, g, unknown, or other
<220> FEATURE:
<221> NAME/KEY: misc_feature
<222> LOCATION: (13)..(13)
<223> OTHER INFORMATION: n is a, c, t, g, unknown, or other
<220> FEATURE:
<221> NAME/KEY: misc_feature
<222> LOCATION: (14)..(14)
<223> OTHER INFORMATION: n is a, c, t, g, unknown, or other
<220> FEATURE:
<221> NAME/KEY: misc_feature
<222> LOCATION: (15)..(15)
<223> OTHER INFORMATION: n is a, c, t, g, unknown, or other
<220> FEATURE:
<221> NAME/KEY: misc_feature
<222> LOCATION: (16)..(16)
<223> OTHER INFORMATION: n is a, c, t, g, unknown, or other
<220> FEATURE:
<221> NAME/KEY: misc_feature
<222> LOCATION: (17)..(17)
<223> OTHER INFORMATION: n is a, c, t, g, unknown, or other
<220> FEATURE:
<221> NAME/KEY: misc_feature
<222> LOCATION: (18)..(18)
<223> OTHER INFORMATION: n is a, c, t, g, unknown, or other
<220> FEATURE:
<221> NAME/KEY: misc_feature
<222> LOCATION: (19)..(19)
<223> OTHER INFORMATION: n is a, c, t, g, unknown, or other
<220> FEATURE:
<221> NAME/KEY: misc_feature
<222> LOCATION: (20)..(20)
```

```
<223> OTHER INFORMATION: n is a, c, t, g, unknown, or other
<220> FEATURE:
<221> NAME/KEY: misc_feature
<222> LOCATION: (21)..(21)
<223> OTHER INFORMATION: n is a, c, t, g, unknown, or other
<220> FEATURE:
<221> NAME/KEY: misc_feature
<222> LOCATION: (22)..(22)
<223> OTHER INFORMATION: n is a, c, t, g, unknown, or other

<400> SEQUENCE: 68
scgaynrnnn nnnnnnnnnn nnhd                                         24

<210> SEQ ID NO 69
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: PROXBBNNAPA motif

<400> SEQUENCE: 69 caaacacc                                                            8

<210> SEQ ID NO 70
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: PYRIMIDINEBOXHVEPB1 motif

<400> SEQUENCE: 70 tttttccc                                                            8

<210> SEQ ID NO 71
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: RBCSCONSENSUS motif

<400> SEQUENCE: 71 aatccaa                                                             7

<210> SEQ ID NO 72
<211> LENGTH: 5
<212> TYPE: DNA
<213> ORGANISM: Artifical Sequence
<220> FEATURE:
<221> NAME/KEY: misc_feature
<222> LOCATION: (1)..(5)
<223> OTHER INFORMATION: ROOTMOTIFTAPOX1 motif

<400> SEQUENCE: 72 atatt                                                               5

<210> SEQ ID NO 73
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: RYREPEATVFLEB4 motif
```

```
<400> SEQUENCE: 73 catgcatg                                                                    8

<210> SEQ ID NO 74
<211> LENGTH: 9
<212> TYPE: DNA
<213> ORGANISM: Artifical Sequence
<220> FEATURE:
<221> NAME/KEY: misc_feature
<222> LOCATION: (1)..(9)
<223> OTHER INFORMATION: SEF1MOTIF motif

<400> SEQUENCE: 74 atatttaww                                                                   9

<210> SEQ ID NO 75
<211> LENGTH: 9
<212> TYPE: DNA
<213> ORGANISM: Artifical Sequence
<220> FEATURE:
<221> NAME/KEY: misc_feature
<222> LOCATION: (1)..(9)
<223> OTHER INFORMATION: SORLREP3AT motif

<400> SEQUENCE: 75 tgtatatat                                                                   9

<210> SEQ ID NO 76
<211> LENGTH: 9
<212> TYPE: DNA
<213> ORGANISM: Artifical Sequence
<220> FEATURE:
<221> NAME/KEY: misc_feature
<222> LOCATION: (1)..(9)
<223> OTHER INFORMATION: SURE2STPAT21 motif

<400> SEQUENCE: 76 aatactaat                                                                   9

<210> SEQ ID NO 77
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: SV40COREENHAN motif

<400> SEQUENCE: 77 gtggwwhg                                                                    8

<210> SEQ ID NO 78
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: TATABOX2 motif

<400> SEQUENCE: 78 tataaat                                                                     7

<210> SEQ ID NO 79
<211> LENGTH: 7
<212> TYPE: DNA
```

```
<213> ORGANISM: Artifical Sequence
<220> FEATURE:
<221> NAME/KEY: misc_feature
<222> LOCATION: (1)..(7)
<223> OTHER INFORMATION: TATABOX3 motif

<400> SEQUENCE: 79 tattaat                                                              7

<210> SEQ ID NO 80
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: TATABOX4 motif

<400> SEQUENCE: 80 tatataa                                                              7

<210> SEQ ID NO 81
<211> LENGTH: 6
<212> TYPE: DNA
<213> ORGANISM: Artifical Sequence
<220> FEATURE:
<221> NAME/KEY: misc_feature
<222> LOCATION: (1)..(6)
<223> OTHER INFORMATION: TATABOX5 motif

<400> SEQUENCE: 81 ttattt                                                               6

<210> SEQ ID NO 82
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: TATABOXOSPAL motif

<400> SEQUENCE: 82 tatttaa                                                              7

<210> SEQ ID NO 83
<211> LENGTH: 9
<212> TYPE: DNA
<213> ORGANISM: Artifical Sequence
<220> FEATURE:
<221> NAME/KEY: misc_feature
<222> LOCATION: (1)..(9)
<223> OTHER INFORMATION: TELOBOXATEEF1AA1 motif

<400> SEQUENCE: 83 aaaccctaa                                                            9

<210> SEQ ID NO 84
<211> LENGTH: 11
<212> TYPE: DNA
<213> ORGANISM: Artifical Sequence
<220> FEATURE:
<221> NAME/KEY: misc_feature
<222> LOCATION: (1)..(11)
<223> OTHER INFORMATION: TL1ATSAR motif

<400> SEQUENCE: 84
ctgaagaaga a                                                        11
```

```
<210> SEQ ID NO 85
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: UP2ATMSD motif

<400> SEQUENCE: 85 aaacccta                                                                  8

<210> SEQ ID NO 86
<211> LENGTH: 7
<212> TYPE: DNA
<213> ORGANISM: Artifical Sequence
<220> FEATURE:
<221> NAME/KEY: misc_feature
<222> LOCATION: (1)..(7)
<223> OTHER INFORMATION: WBBOXPCWRKY1 motif

<400> SEQUENCE: 86 tttgacy                                                                   7

<210> SEQ ID NO 87
<211> LENGTH: 8
<212> TYPE: DNA
<213> ORGANISM: Artifical Sequence
<220> FEATURE:
<221> NAME/KEY: misc_feature
<222> LOCATION: (1)..(8)
<223> OTHER INFORMATION: XYLAT motif

<400> SEQUENCE: 87 acaaagaa                                                                  8
```

PROMOTER, PROMOTER CONTROL ELEMENTS, AND COMBINATIONS, AND USES THEREOF

CROSS-REFERENCE TO RELATED APPLICATIONS

This application is a Divisional of co-pending application Ser. No. 12/865,719 filed on Jul. 30, 2010, which is a National Phase of PCT International Application No. PCT/US09/32485 filed on Jan. 29, 2009, which claims priority to U.S. provisional application Ser. No. 61/025,697, filed on Feb. 1, 2008. All of the above applications are hereby expressly incorporated by reference into the present application.

INCORPORATION-BY-REFERENCE OF SEQUENCE LISTING OR TABLE

The material in the accompanying sequence listing is hereby incorporated by reference into this application. The accompanying file, named 2014_09_03 Sequence_Listing_2750-1720PUS3.txt was created on May 20, 2013 and is 70 KB. The file can be accessed using Microsoft Word on a computer that uses Windows OS.

FIELD OF THE INVENTION

The present invention relates to promoters and promoter control elements that are useful for modulating transcription of a desired polynucleotide. Such promoters and promoter control elements can be included in polynucleotide constructs, expression cassettes, vectors, or inserted into the chromosome or as an exogenous element, to modulate in vivo and in vitro transcription of a polynucleotide. Host cells, including plant cells, and organisms, such as regenerated plants therefrom, with desired traits or characteristics using polynucleotides comprising the promoters and promoter control elements of the present invention are also a part of the invention.

BACKGROUND OF THE INVENTION

This invention relates to promoter sequences and promoter control element sequences which are useful for the transcription of polynucleotides in a host cell or transformed host organism.

The introduction of genes into plants has resulted in the development of plants having new and useful phenotypes such as pathogen resistance, higher levels of healthier types of oils, novel production of healthful components such as beta-carotene synthesis in rice. An introduced gene is generally a chimeric gene composed of the coding region that confers the desired trait and regulatory sequences. One regulatory sequence is the promoter, which is located 5' to the coding region. This sequence is involved in regulating the pattern of expression of a coding region 3' thereof. The promoter sequence binds RNA polymerase complex as well as one or more transcription factors that are involved in producing the RNA transcript of the coding region.

The promoter region of a gene used in plant transformation is most often derived from a different source than is the coding region. It may be from a different gene of the same species of plant, from a different species of plant, from a plant virus, an algae species, a fungal species, or it may be a composite of different natural and/or synthetic sequences. Properties of the promoter sequence generally determine the pattern of expression for the coding region that is operably linked to the promoter. Promoters with different characteristics of expression have been described. The promoter may confer broad expression as in the case of the widely-used cauliflower mosaic virus (CaMV) 35S promoter. The promoter may confer tissue-specific expression as in the case of the seed-specific phaseolin promoter. The promoter may confer a pattern for developmental changes in expression. The promoter may be induced by an applied chemical compound, or by an environmental condition applied to the plant.

The promoter that is used to regulate a particular coding region is determined by the desired expression pattern for that coding region, which itself is determined by the desired resulting phenotype in the plant. For example, herbicide resistance is desired throughout the plant so the 35S promoter is appropriate for expression of an herbicide-resistance gene. A seed-specific promoter is appropriate for changing the oil content of soybean seed. An endosperm-specific promoter is appropriate for changing the starch composition of corn seed. A root-specific promoter can be important for improving water or nutrient up-take in a plant. Control of expression of an introduced gene by the promoter is important because it is sometimes detrimental to have expression of an introduced gene in non-target tissues. For example, a gene which induces cell death can be expressed in male and/or female gamete cells in connection with bioconfinement.

One of the primary goals of biotechnology is to obtain organisms, such as plants, mammals, yeast, and prokaryotes having particular desired characteristics or traits. Examples of these characteristics or traits abound and may include, for example, in plants, virus resistance, insect resistance, herbicide resistance, enhanced stability or additional nutritional value. Recent advances in genetic engineering have enabled researchers in the field to incorporate polynucleotide sequences into host cells to obtain the desired qualities in the organism of choice. This technology permits one or more polynucleotides from a source different than the organism of choice to be transcribed by the organism of choice. If desired, the transcription and/or translation of these new polynucleotides can be modulated in the organism to exhibit a desired characteristic or trait. Alternatively, new patterns of transcription and/or translation of polynucleotides endogenous to the organism can be produced.

SUMMARY OF THE INVENTION

The present invention is directed to isolated polynucleotide sequences that comprise promoters and promoter control elements from plants, especially *Arabidopsis thaliana*, and other promoters and promoter control elements functional in plants.

It is an object of the present invention to provide isolated polynucleotides that are promoter or promoter control sequences. These promoter sequences comprise, for example, (1) a polynucleotide having a nucleotide sequence according to any one of SEQ. ID. Nos. 1-26 or residues 601-1000 of SEQ ID NO: 26;

(2) a polynucleotide having a nucleotide sequence having at least 80% sequence identity to a sequence according to SEQ. ID. Nos. 1-26 or residues 601-1000 of SEQ ID NO: 26; and (3) a polynucleotide having a nucleotide sequence which hybridizes to a sequence according to SEQ. ID. Nos.

1-26 or nucleic acid residues 601-1000 of SE ID NO: 26 under a condition establishing a Tm−5° C.

Promoter or promoter control element sequences of the present invention are capable of modulating preferential transcription.

In another embodiment, the present promoter control elements are capable of serving as or fulfilling the function, for example, as a core promoter, a TATA box, a polymerase binding site, an initiator site, a transcription binding site, an enhancer, an inverted repeat, a locus control region, and/or a scaffold/matrix attachment region.

It is yet another object of the present invention to provide a polynucleotide that includes at least a first and a second promoter control element. The first promoter control element is a promoter control element sequence as discussed above, and the second promoter control element is heterologous to the first control element; wherein, the first and second control elements are operably linked. Such promoters may modulate transcript levels preferentially in a particular tissue or under particular conditions.

In another embodiment, the present isolated polynucleotide comprises a promoter or a promoter control element as described above, wherein the promoter or promoter control element is operably linked to a polynucleotide to be transcribed.

In another embodiment of the present invention, the promoter and promoter control elements of the instant invention are operably linked to a heterologous polynucleotide that is a regulatory sequence.

It is another object of the present invention to provide a host cell comprising an isolated polynucleotide or vector as described above or fragment thereof. Host cells include, for instance, bacterial, yeast, insect, mammalian, fungus, algae, and plant. The host cell can comprise a promoter or promoter control element exogenous to the genome. Such a promoter can modulate transcription in cis- and in trans-.

In yet another embodiment, the host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free system of transcription or host cell. This method comprises providing a polynucleotide or vector according to the present invention as described above, and contacting the sample of the polynucleotide or vector with conditions that permit transcription.

In another embodiment of the present method, the polynucleotide or vector preferentially modulates, depending upon the function of the particular promoter, constitutive transcription, stress induced transcription, light induced transcription, dark induced transcription, leaf transcription, root transcription, stem or shoot transcription, silique or fruit transcription, callus transcription, rhizome transcription, stem node transcription, gamete tissue transcription, flower transcription, immature bud and inflorescence specific transcription, senescing induced transcription, germination transcription and/or drought transcription.

One embodiment of the invention is directed to an isolated nucleic acid molecule having promoter activity comprising a nucleotide sequence selected from the group consisting of:
a. a nucleotide sequence according to any one of SEQ ID NOs. 1-26;
b. a nucleotide sequence of nucleic acid residues 601-1000 of SEQ ID NO: 26;
c. a nucleotide sequence comprising a functional fragment of (a) or (b), wherein said fragment has promoter activity,
and wherein said isolated nucleic acid molecule is not SEQ ID NO: 5.

Another embodiment of the invention is directed to an isolated nucleic acid molecule comprising a nucleotide sequence that shows at least 80 percent sequence identity to any one of SEQ ID NOs: 1-26 or nucleic acid residues 601-1000 of SEQ ID NO: 26, wherein said nucleic acid molecule comprises a regulatory region that directs transcription of an operably linked heterologous polynucleotide, and wherein said isolated nucleic acid molecule is not SEQ ID NO: 5.

In another embodiment of the invention the isolated nucleic acid molecule shows at least 85 percent sequence identity to any one of SEQ ID NOs: 1-26 or nucleic acid residues 601-1000 of SEQ ID NO: 26.

In another embodiment of the invention the isolated nucleic acid molecule has at least 90 percent sequence identity to any one of SEQ ID NOs: 1-26 or nucleic acid residues 601-1000 of SEQ ID NO: 26.

In another embodiment the isolated nucleic acid molecule comprises at least one member selected from the group consisting of a promoter, an enhancer and an intron.

In a further embodiment of the invention, the isolated nucleic acid molecule consists of any one of SEQ ID NOs: 1-4, 6-26 and the nucleic acid residues 601-1000 of SEQ ID NO: 26.

Another embodiment of the invention is directed to a vector construct comprising:
a. a first nucleic acid molecule as described above; and
b. a transcribable polynucleotide molecule,
wherein said first nucleic acid molecule and said transcribable polynucleotide molecule are heterologous to each other and are operably linked.

In another embodiment of the invention, the first nucleic acid molecule consists of the nucleic acid molecule set forth in any one of SEQ ID NOs: 1-26 or nucleic acid residues 601-1000 of SEQ ID NO: 26.

In another embodiment of the invention, the transcribable polynucleotide molecule encodes a polypeptide.

In another embodiment of the invention, the transcribable polynucleotide molecule is operably linked to said first nucleic acid molecule in the sense orientation.

In another embodiment of the invention, the transcribable polynucleotide molecule is transcribed into an RNA molecule that expresses the polypeptide encoded by transcribable polynucleotide molecule.

In another embodiment of the invention, the transcribable polynucleotide molecule is operably linked to said first nucleic acid molecule in the antisense orientation.

In another embodiment of the invention, the transcribable polynucleotide molecule is transcribed into an antisense RNA molecule.

In another embodiment of the invention, the transcribable polynucleotide molecule is transcribed into an interfering RNA against an endogenous gene.

In another embodiment of the invention, the transcribable polynucleotide molecule encodes a polypeptide of agronomic interest.

Another embodiment of the invention is directed to a plant or plant cell comprising:
a. the nucleic acid molecule described above that is operably linked to a heterologous polynucleotide, or
b. the vector construct described above.

Another embodiment of the invention is directed to a plant or plant cell stably transformed with the vector construct described above.

Another embodiment of the invention is directed to a seed of a plant as described above.

Another embodiment of the invention is directed to a method of directing transcription by combining, in an environment suitable for transcription:
 a. a first nucleic acid molecule as described above; and
 b. a transcribable polynucleotide molecule;
wherein said first nucleic acid molecule and said transcribable polynucleotide molecule are heterologous to each other and operably linked.

Another embodiment of the invention is directed to a method of expressing an exogenous coding region in a plant comprising:
 a. transforming a plant cell with a vector as described above,
 b. regenerating a stably transformed plant from the transformed plant cell of step (a); and
 c. selecting plants containing a transformed plant cell, wherein expression of the transcribable polynucleotide molecule results in production of a polypeptide encoded by said transcribable polynucleotide molecule.

Another embodiment of the invention is directed to a method of altering the expression of a gene in a plant comprising:
 a. transforming a plant cell with the nucleic acid molecule as described above that is operably linked to a heterologous polynucleotide, and
 b. regenerating stably transformed plants from said transformed plant cell.

Another embodiment of the invention is directed to a plant prepared according to the method described above.

Another embodiment of the invention is directed to a seed from the plant described above.

Another embodiment of the invention is directed to a method of producing a transgenic plant, said method comprising;
 a. introducing into a plant cell:
  (i) an isolated polynucleotide comprising the nucleic acid as described above that is operably linked to a heterologous polynucleotide, or
  (ii) the vector as described above; and
 b. growing a plant from said plant cell.

Other and further objects of the present invention will be made clear or become apparent from the following description.

BRIEF DESCRIPTION OF THE TABLES AND FIGURES

The Tables consist of the Expression Reports for some of the promoters of the invention providing the nucleotide sequence for each promoter and details for expression driven by each of the nucleic acid promoter sequences as observed in transgenic plants. The results are presented as summaries of the spatial expression, which provides information as to gross and/or specific expression in various plant organs and tissues. The observed expression pattern is also presented, which gives details of expression during different generations or different developmental stages within a generation. Additional information is provided regarding the source organism of the promoter, and the vector and marker genes used for the construct. The following symbols are used consistently throughout the Tables:

T1: First generation transformant
 T2: Second generation transformant
 T3: Third generation transformant
 (L): low expression level
 (M): medium expression level
 (H): high expression level Each row of the table begins with heading of the data to be found in the section. The following provides a description of the data to be found in each section:

| Heading in Tables | Description |
|---|---|
| 1. Promoter Expression Report # | Identifies the particular promoter by its construct ID. |
| 2. Promoter tested in: | Identifies the organism in which the promoter-marker vector was tested. |
| 3. Spatial expression summary: | Identifies the specific parts of the plant where various levels of GFP expression are observed. Expression levels are noted as either low (L), medium (M), or high (H). |
| 4. Observed expression pattern: | Provides a general explanation of where GFP expression in different generations of plants was observed. |
| 5. Source promoter organism: | Identifies the plant species from which the promoter was derived. |
| 6. Vector: | Identifies the vector used into which a promoter was cloned. |
| 7. Marker type: | Identifies the type of marker linked to the promoter. The marker is used to determine patterns of gene expression in plant tissue. |
| 8. Generation screened: T1 Mature T2 Seedling T2 Mature T3 Seedling | Identifies the plant generation(s) used in the screening process. T1 plants are those plants subjected to the transformation event while the T2 generation plants are from the seeds collected from the T1 plants and T3 plants are from the seeds of T2 plants. |
| 9. Inductions completed: | Provides summary of experiment schedule. |
| 10. T1 Mature Plant Expression: | Identifies plant tissues that were observed for possible expression, and identifies (H, M or L) level of observed expression. |
| 11. T2 Seedling Expression: | Identifies plant tissues that were observed for possible expression, and identifies (H, M or L) level of observed expression. |

-continued

| Heading in Tables | Description |
| --- | --- |
| 12. T2 Mature Plant Expression: | Identifies plant tissues that were observed for possible expression, and identifies (H, M or L) level of observed expression. |
| 13. Utility | Provides a description of the utility of the sequence, including a trait area and, in some instances, a sub-trait area. |
| 14. Construct Promoter Candidate I.D. cDNA I.D. | Identifies the promoter by its construct ID and internal candidate number, and cDNA number |
| 15. Lines/Events expressing: | Identifies the line/event numbers that expressed under the promoter. |

Some promoter reports describe additional experiments and results with the particular promoter.

BRIEF DESCRIPTION OF THE FIGURES

FIG. 1 is a schematic representation of a vector pNewbin4-HAP1-GFP that is useful to insert promoters of the invention into a plant. The definitions of the abbreviations used in the vector map are as follows:
Ori—the origin of replication used by an *E. coli* host
RB—sequence for the right border of the T-DNA from pMOG800
BstXI—restriction enzyme cleavage site used for cloning
HAP1VP16—coding sequence for a fusion protein of the HAP1 and VP16 activation domains
NOS—terminator region from the nopaline synthase gene
HAP1UAS—the upstream activating sequence for HAP1
5ERGFP—the green fluorescent protein gene that has been optimized for localization to the endoplasmic reticulum
OCS2—the terminator sequence from the octopine synthase 2 gene
OCS—the terminator sequence from the octopine synthase gene
p28716 (a.k.a. 28716 short)—promoter used to drive expression of the PAT (BAR) gene
PAT (BAR)—a marker gene conferring herbicide resistance
LB—sequence for the left border of the T-DNA from pMOG800
Spec—a marker gene conferring spectinomycin resistance
TrfA—transcription repression factor gene
RK2-OriV—origin of replication for *Agrobacterium*

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides promoters capable of driving the expression of an operably linked transgene. The design, construction, and use of these promoters is one object of this invention. The promoter sequences, SEQ ID NOs: 1-26 and residues 601-1000 of SEQ ID NO: 26, are capable of transcribing operably linked nucleic acid molecules in particular plant tissues/organs or during particular plant growth stages, and therefore can selectively regulate expression of transgenes in these tissues/organs or at these times of plant development.

1. Definitions

Chimeric: The term "chimeric" is used to describe polynucleotides or genes, or constructs wherein at least two of the elements of the polynucleotide or gene or construct, such as the promoter and the polynucleotide to be transcribed and/or other regulatory sequences and/or filler sequences and/or complements thereof, are heterologous to each other.

Broadly Expressing Promoter: Promoters referred to herein as "broadly expressing promoters" actively promote transcription under most, but not necessarily all, environmental conditions and states of development or cell differentiation. Examples of broadly expressing promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of domains include, without limitation, AP2, helicase, homeobox, zinc finger, etc.

Endogenous: The term "endogenous," within the context of the current invention refers to any polynucleotide, polypeptide or protein sequence which is a natural part of a cell or organism(s) regenerated from said cell. In the context of promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below, and include Agrobacterium-mediated transformation (of dicots—e.g. Salomon et al. (1984) EMBO J. 3:141; Herrera-Estrella et al. (1983) EMBO J. 2:987; of monocots, representative papers are those by Escudero et al. (1996) Plant J. 10:355), Ishida et al. (1996) Nature Biotech 14:745, May et al. (1995) Bio/Technology 13:486), biolistic methods (Armaleo et al. (1990) Current Genetics 17:97), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Heterologous sequences: "Heterologous sequences" are those that are not operatively linked or are not contiguous to each other in nature. For example, a promoter from corn is considered heterologous to an Arabidopsis coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Homologous: In the current invention, a "homologous" polynucleotide refers to a polynucleotide that shares sequence similarity with the polynucleotide of interest. This similarity may be in only a fragment of the sequence and often represents a functional domain such as, examples including, without limitation, a DNA binding domain or a domain with tyrosine kinase activity. The functional activities of homologous polynucleotides are not necessarily the same.

Inducible Promoter: An "inducible promoter" in the context of the current invention refers to a promoter, the activity of which is influenced by certain conditions, such as light, temperature, chemical concentration, protein concentration, conditions in an organism, cell, or organelle, etc. A typical example of an inducible promoter, which can be utilized with the polynucleotides of the present invention, is PARSK1, the promoter from an Arabidopsis gene encoding a serine-threonine kinase enzyme, and which promoter is induced by dehydration, abscisic acid and sodium chloride (Wang and Goodman (1995) Plant J. 8:37). Examples of environmental conditions that may affect transcription by inducible promoters include anaerobic conditions, elevated temperature, the presence or absence of a nutrient or other chemical compound or the presence of light.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene or coding region from a different plant species or from a non-plant organism.

Modulate Transcription Level: As used herein, the phrase "modulate transcription" describes the biological activity of a promoter sequence or promoter control element. Such modulation includes, without limitation, up- and down-regulation of initiation of transcription, rate of transcription, and/or transcription levels.

Operable Linkage: An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoding the polynucleotide and if the nature of the linkage between the two DNA sequences does not (1) result in the introduction of a frame-shift mutation, (2) interfere with the ability of the promoter sequence to direct the expression of the protein, antisense RNA, RNAi or ribozyme, or (3) interfere with the ability of the DNA template to be transcribed. Thus, a promoter sequence would be operably linked to a polynucleotide sequence if the promoter was capable of effecting transcription of that polynucleotide sequence.

Percentage of sequence identity As used herein, the term "percent sequence identity" refers to the degree of identity between any given query sequence, e.g., SEQ ID NOs: 1-26, and a subject sequence. A subject sequence typically has a length that is from about 80 percent to 250 percent of the length of the query sequence, e.g., 82, 85, 87, 89, 90, 93, 95, 97, 99, 100, 105, 110, 115, or 120, 130, 140, 150, 160, 170, 180, 190, 200, 210, 220, 230, 240, or 250 percent of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna et al. (2003) Nucleic Acids Res. 31(13):3497-500.

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For an alignment of multiple nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher website and at the European Bioinformatics Institute website on the World Wide Web.

To determine a percent identity of a subject polypeptide or nucleic acid sequence to a query sequence, the sequences are aligned using Clustal W, the number of identical matches in the alignment is divided by the length of the query sequence, and the result is multiplied by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill in the art.

Plant Tissue: The term "plant tissue" includes differentiated and undifferentiated tissues or plants, including but not limited to roots, stems, shoots, rhizomes, cotyledons, epicotyl, hypocotyl, leaves, pollen, seeds, gall tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, proximal to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible via the internet). The database at the NCBI FTP site utilizes "gi" numbers assigned by NCBI as a unique identifier for each sequence in the databases, thereby providing a non-redundant database for sequence from various databases, including GenBank, EMBL, DBBJ (DNA Database of Japan) and PDB (Brookhaven Protein Data Bank).

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

The nucleic acid sequence set forth in SEQ ID NOs:1-26 are examples of regulatory regions provided herein. However, a regulatory region can have a nucleotide sequence that deviates from that set forth in SEQ ID NOs:1-26, while retaining the ability to direct expression of an operably linked nucleic acid. For example, a regulatory region having 80% or greater (e.g. 85% or greater, 90% or greater 91% or greater, 92% or greater, 93% or greater, 94% or greater, 95% or greater, 96% or greater, 97% or greater, 98% or greater, or 99% or greater) sequence identity to the nucleotide sequence set forth in SEQ ID NOs:1-25, or 26 can direct expression of an operably linked nucleic acid.

A regulatory region can also be a fragment of SEQ ID NOs:1-25, or 26, while retaining promoter activity, i.e. the ability to direct expression of an operably linked nucleic acid. Additional examples of regulatory regions are identified in the Sequence Listing.

Regulatory regions can be classified in two categories, promoters and other regulatory regions.

Regulatory Sequence: The term "regulatory sequence," as used in the current invention, refers to any nucleotide sequence that influences transcription or translation initiation and rate, or stability and/or mobility of a transcript or polypeptide product. Regulatory sequences include, but are not limited to, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, certain sequences within amino acid coding sequences such as secretory signals, protease cleavage sites, etc.

A 5' untranslated region (5' UTR) of a gene is generally defined as a polynucleotide segment between the transcription start site (TSS) and the coding sequence start site (ATG codon) of a messenger RNA or cDNA. Alternately, 5' UTR can be synthetically produced or manipulated DNA elements. A "plant 5'UTR" can be a native or non-native 5'UTR that is functional in plant cells. A 5' UTR can be used as a 5' regulatory element for modulating expression of an operably linked transcribable polynucleotide molecule. For example, 5' UTRs derived from heat shock protein genes have been demonstrated to enhance gene expression in plants (see for example, U.S. Pat. No. 5,659,122 and U.S. Pat. No. 5,362,865, all of which are incorporated herein by reference). Examples of 5'UTRs include those shown in SEQ ID NOs: 1-4, 6-10, 13-26.

Specific Promoters: In the context of the current invention, "specific promoters" refers to a subset of promoters that have a high preference for modulating transcript levels in a specific tissue, or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present invention, are: PTA29, a promoter which is capable of driving gene transcription specifically in tapetum and only during anther development (Koltonow et al. (1990) *Plant Cell* 2:1201; RCc2 and RCc3, promoters that direct root-specific gene transcription in rice (Xu et al. (1995) *Plant Mol. Biol.* 27:237; TobRB27, a root-specific promoter from tobacco (Yamamoto et al. (1991) *Plant Cell* 3:371). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription."

A regulatory region can contain conserved regulatory motifs. Such a regulatory region can be any one of the sequences set forth in SEQ ID NOs:1-26, or a regulatory region having a nucleotide sequence that deviates from any one of those set forth in SEQ ID NOs:1-26, while retaining the ability to direct expression of an operably linked nucleic acid. For example, a regulatory region can contain a CAAT box or a TATA box. A CAAT box is a conserved nucleotide sequence involved in initiation of transcription. A CAAT box functions as a recognition and binding site for regulatory proteins called transcription factors. A TATA box is another conserved nucleotide sequence involved in transcription initiation. A TATA box seems to be important in determining accurately the position at which transcription is initiated.

Other conserved regulatory motifs can be identified using methods known in the art. For example, a regulatory region can be analyzed using the PLACE (PLAnt Cis-acting regulatory DNA Elements) Web Signal Scan program on the world wide web at dna.affrc.go.jp/PLACE/signalscan.html. See, Higo et al., *Nucleic Acids Research*, 27(1):297-300 (1999); and Prestridge, *CABIOS*, 7:203-206 (1991). Examples of conserved regulatory motifs can be found in the PLACE database on the world wide web at dna.affrc.go.jp/PLACE/. See, Higo et al., supra.

A regulatory region such as any one of SEQ ID NOs:1-26, or a regulatory region having a nucleotide sequence that deviates from those set forth in SEQ ID NOs:1-26, while retaining the ability to direct expression of an operably linked nucleic acid, can contain one or more conserved regulatory motifs, which can be found in the PLACE database. For example, such a regulatory region can contain a –300CORE motif having the consensus sequence TGTAAAG (SEQ ID NO:27). See, Forde et al., *Nucleic Acids Res* 13:7327-7339 (1985); Colot et al., *EMBO J* 6:3559-3564 (1987); Thomas and Flavell, *Plant Cell* 2:1171-1180 (1990); Thompson et al., *Plant Mol Biol* 15:755-764 (1990); Vicente-Carbajosa et al., *Proc Natl Acad Sci USA* 94:7685-7690 (1997); Mena et al., *Plant J* 16:53-62 (1998); Shing, *Plant Physiol* 118: 1111-1120 (1998). Such a regulatory region can contain an ABREATCONSENSUS motif having the consensus sequence YACGTGGC (SEQ ID NO:28). See, Choi et al., *J Biol Chem* 275: 1723-1730 (2000); Kang et al., *Plant Cell* 14: 343-357 (2002); Oh et al., *Plant Physiology* 138: 341-351 (2005); Choi et al., *Plant Physiol* 139: 1750-1761(2005). Such a regulatory region can contain an ABREATRD22 motif having the consensus sequence RYACGTGGYR (SEQ ID NO:29). See, Iwasaki et al., *Mol Gen Genet* 247:391-398 (1995); Bray, *Trends in Plant Science* 2:48-54 (1997); Busk and Pages, *Plant Mol Biol* 37:425-435 (1998). A regulatory region can contain an ABRELATERD1 motif having the consensus sequence ACGTG (SEQ ID NO:30). See, Simpson et al., *Plant J* 33: 259-270 (2003); Nakashima et al., *Plant Mol Biol* 60:51-68 (2006). A regulatory region can contain an ABREMOTIFAOSOSEM motif having the consensus sequence TACGTGTC (SEQ ID NO:31). See, Hattori et al., *Plant J* 7: 913-925 (1995); Hobo et al., *Proc Natl Acad Sci USA* 96: 15348-15353 (1999). A regulatory region can contain an ABRERATCAL motif having the consensus sequence MACGYGB (SEQ ID NO:32). See, Kaplan et al., *Plant Cell* 18:2733-2748 (2006). A regulatory region can contain an ACGTCBOX motif having the consensus sequence GACGTC (SEQ ID NO:33). See, Foster et al., *FASEB J* 8:192-200 (1994); Izawa et al., *Plant Cell* 6:1277-1287 (1994); Izawa et al., *J Mol Biol* 230:1131-1144 (1993). A regulatory region can contain an ACGTOSGLUB1 motif having the consensus sequence GTACGTG (SEQ ID NO:34). See, Washida et al., *Plant Mol Biol* 40:1-12 (1999); Wu et al., *Plant J* 23: 415-421 (2000). A regulatory region can contain an ACGTTBOX motif having the consensus sequence AACGTT (SEQ ID NO:35). See, Foster et al., *FASEB J* 8:192-200 (1994). A regulatory region can contain an ACIIPVPAL2 motif having the consensus sequence CCACCAACCCCC (SEQ ID NO:36). See, Patzlaff et al., *Plant Mol Biol* 53:597-608 (2003); Hatton et al., *Plant J* 7:859-876 (1995); Gomez-Maldonado et al., *Plant J* 39:513-526 (2004). A regulatory region can contain an AGL2ATCONSENSUS motif having the consensus sequence NNWNCCAWWWWTRGWWAN (SEQ ID NO:37). See, Huang et al., *Plant Cell* 8: 81-94 (1996). A regulatory region can contain an AMYBOX2 motif having the consensus sequence TATCCAT (SEQ ID NO:38). See, Huang et al., *Plant Mol Biol* 14:655=668 (1990); Hwang et al., *Plant Mol Biol* 36:331=341 (1998). A regulatory region can contain an ANAERO1CONSENSUS motif having the consensus sequence AAACAAA (SEQ ID NO:39). See, Mohanty et al., *Ann Bot* (Lond). 96: 669-681 (2005). A regulatory region can contain an ARE1 motif having the consensus sequence RGTGACNNNGC (SEQ ID NO:40). See, Rushmore et al., *J Biol Chem* 266:11632-11639 (1991). A regulatory region can contain an ATHB6COREAT motif having the consensus sequence CAATTATTA (SEQ ID NO:41). See, Himmelbach et al., *EMBO J* 21:3029-3038 (2002). A regulatory region can contain an AUXRETGA1GMGH3 motif having the consensus sequence TGACGTAA (SEQ ID NO:42). See, Liu et al., *Plant Cell* 6:645-657 (1994); Liu et al., *Plant Physiol* 115:397-407 (1997); Guilfoyle et al., *Plant Physiol* 118: 341-347 (1998). A regulatory region can contain a BOXI-IPCCHS motif having the consensus sequence ACGTGGC (SEQ ID NO:43). See, Block et al., *Proc Natl Acad Sci USA* 87:5387-5391(1990); Terzaghi and Cashmore, *Annu Rev Plant Physiol Plant Mol Biol* 46:445-474 (1995); Nakashima et al., *Plant Mol Biol* 60: 51-68 (2006). A regulatory region can contain a BOXLCOREDCPAL motif having the consensus sequence ACCWWCC (SEQ ID NO:44). See, Meada et al., *Plant Mol Biol* 59: 739-752. (2005). A regulatory region can contain a CACGCAATG-MGH3 motif having the consensus sequence CACGCAAT (SEQ ID NO:45). See, Ulmasov et al., *Plant Cell* 7: 1611-1623 (1995). A regulatory region can contain a CARGAT-CONSENSUS motif having the consensus sequence CCWWWWWWGG (SEQ ID NO:46). See, Hepworth et al., *EMBO J* 21: 4327-4337 (2002); Michaels et al., *Plant J* 33: 867-874 (2003); Hong et al., *Plant Cell* 15:1296-1309 (2003); Folter and Angenent, *Trends Plant Sci* 11:224-231 (2006). A regulatory region can contain a CARGCW8GAT motif having the consensus sequence CWWWWWWWWG (SEQ ID NO:47). See, Tang and Perry, *J Biol Chem* 278: 28154-28159 (2003); Folter and Angenent, *Trends Plant Sci* 11:224-231 (2006). A regulatory region can contain a CIA-CADIANLELHC motif having the consensus sequence CAANNNNATC (SEQ ID NO:48). See, Piechulla et al., *Plant Mol Biol* 38:655-662 (1998). A regulatory region can contain a DPBFCOREDCDC3 motif having the consensus sequence ACACNNG (SEQ ID NO:49). See, Kim et al., *Plant J* 11: 1237-1251 (1997); Finkelstein and Lynch, *Plant Cell* 12: 599-609 (2000); Lopez-Molina and Chua, *Plant Cell Physiol* 41: 541-547 (2000). A regulatory region can contain a DRE2COREZMRAB17 motif having the consensus sequence ACCGAC (SEQ ID NO:50). See, Busk et al., *Plant J* 11: 1285-1295 (1997); Dubouzet et al., *Plant J* 33: 751-763 (2003); Kizis and Pages, *Plant J* 30:679-689 (2002). A regulatory region can contain an E2FCONSENSUS motif having the consensus sequence WTTSSCSS (SEQ ID NO:51). See, Vandepoele et al., *Plant Physiol* 139: 316-328. (2005). A regulatory region can contain an EMHVCHORD motif having the consensus sequence TGTAAAGT (SEQ ID NO:52). See, Muller and Knudsen, *Plant J* 4: 343-355 (1993). A regulatory region can contain an EVENINGAT motif having the consensus sequence AAAATATCT (SEQ ID NO:53). See, Rawat et al., *Plant Mol Biol* 57: 629-643 (2005) and Harmer et al., *Science* 290: 2110-2113 (2000). A regulatory region can contain an GLMHVCHORD motif having the consensus sequence RTGASTCAT (SEQ ID NO:54). See, Albani et al., *Plant Cell* 9: 171-184 (1997); Muller M *Plant J* 4: 343-355 (1993); Onate et al., *J Biol Chem* 274: 9175-9182 (1999). A regulatory region can contain a GT1 Consensus motif having the consensus sequence GRWAAW (SEQ ID NO:55). See, Terzaghi and Cashmore, supra.; Villain et al., *J Biol Chem* 271:32593-32598 (1996); Le Gourrierec et al., *Plant J* 18:663-668 (1999); Buchel et al., *Plant Mol Biol* 40:387-396 (1999); Zhou, *Trends in Plant Science* 4:210-214 (1999). A regulatory region can contain a GT1GMSCAM4 motif having the consensus sequence GAAAAA (SEQ ID NO:56). See, Park et al., *Plant Physiol* 135: 2150-2161 (2004). A regulatory region can contain a HDZIP2ATATHB2 motif having the consensus sequence TAATMATTA (SEQ ID NO:57). See, Ohgishi et al., *Plant J* 25: 389-398 (2001). A regulatory region can contain an IBOXCORENT motif having the consensus sequence GATAAGR (SEQ ID NO:58). See, Martinez-Hernandez et al., *Plant Physiol* 128:1223-1233 (2002). A regulatory region can contain an INRNTPSADB motif having the consensus sequence YTCANTYY (SEQ ID NO:59). See, Nakamura et al., *Plant J* 29: 1-10 (2002). A regulatory region can contain a LEAFYATAG motif having the consensus sequence CCAATGT (SEQ ID NO:60). See, Kamiya et al., *Plant J* 35: 429-441 (2003). A regulatory region can contain a LRENPCABE motif having the consensus sequence ACGTGGCA (SEQ ID NO:61). See, Castresana et al., *EMBO J* 7:1929-1936 (1988). A regulatory region can contain a MARTBOX motif having the consensus sequence TTWTWTTWTT (SEQ ID NO:62). See, Gasser et al., *Intnatl Rev Cyto* 119:57-96 (1989). A regulatory region can contain a MYBGAHV motif having the consensus sequence TAACAAA (SEQ ID NO:63). See, Gubler et al., *Plant Cell* 7:1879-1891 (1995); Morita et al., *FEBS Lett* 423:81-85 (1998); Gubler et al., *Plant J* 17:1-9(1999). A regulatory region can contain a MYBPLANT motif having the consensus sequence MACCWAMC (SEQ ID NO:64). See, Sablowski et al., *EMBO J* 13:128-137 (1994); Tamagnone et al., *Plant Cell* 10: 135-154 (1998). A regulatory region can contain a NRRBNEXTA motif having the consensus sequence TAGTGGAT (SEQ NO:65). See, Elliott and Shirsat, *Plant Mol Biol* 37:675-687 (1998). A regulatory region can contain an O2F3BE2S1 motif having the consensus sequence TCCACGTACT (SEQ ID NO:66). See, Vincentz et al., *Plant Mol Biol* 34:879-889 (1997). A regulatory region can contain a P1BS motif having the consensus sequence GNATATNC (SEQ ID NO:67). See, Rubio et al., *Genes Dev.* 15: 2122-2133. (2001); Shunmann et al., *J Exp Bot.* 55: 855-865. (2004); Shunmann et al., *Plant Physiol* 136: 4205-4214. (2004). A regulatory region can contain a PRECONSCRHSP70A motif having the consensus sequence SCGAYNRNNNNNNNNNNNNNNHD (SEQ ID NO:68). See, von Gromoff et al., *Nucleic Acids Res* 34:4767-4779 (2006). A regulatory region can contain a PROXBBNNAPA motif having the consensus sequence CAAACACC (SEQ ID NO:69). See, Ezcurra et al., *Plant Mol Biol* 40:699-709 (1999); Busk and Pages, supra.: Ezcurra et al., *Plant J* 24:57-66 (2000). A regulatory region can contain a PYRIMIDINEBOXHVEPB1 motif having the consensus sequence TTTTTTCC (SEQ ID NO:70). See, Cercos et al., *Plant J* 19: 107-118 (1999). A regulatory region can contain a RBCSCONSENSUS motif having the consensus sequence AATCCAA (SEQ ID NO:71). See, Manzara and Gruissem, *Photosynth Res* 16:117-139 (1988); Donald and Cashmore, *EMBO J* 9:1717-1726 (1990). A regulatory region can contain a ROOTMOTIFTAPDX1 motif having the consensus sequence ATATT (SEQ ID NO:72). See, Elmayan and Tepfer, *Transgenic Res* 4:388-396 (1995). A regulatory region can contain a RYREPEAT-VFLEB4 motif having the consensus sequence CATGCATG (SEQ ID NO:73). See, Curaba et al., *Plant Physiol* 136: 3660-3669. (2004); Nag et al., *Plant Mol Biol* 59: 821-838 (2005). A regulatory region can contain a SEF1MOTIF motif having the consensus sequence ATATTTAWW (SEQ ID NO:74). See, Allen et al., Plant Cell 1:623-631 (1989); Lessard et al., *Plant Mol Biol* 16:397-413 (1991). A regulatory region can contain a SORLREP3AT motif having the consensus sequence TGTATATAT (SEQ ID NO:75). See, Hudson and Quail, *Plant Physiol* 133: 1605-1616 (2003). A regulatory region can contain a SURE2STPAT21 motif having the consensus sequence AATACTAAT (SEQ ID NO:76). See, Grierson et al., *Plant J* 5:815-826 (1994). A regulatory region can contain a SV40COREENHAN motif having the consensus sequence GTGGWWHG (SEQ ID NO:77). See, Weiher et al., *Science* 219:626-631 (1983); Green et al., *EMBO J* 6:2543-2549 (1987); Donald and Cashmore, *EMBO J* 9:1717-1726 (1990). A regulatory region can contain a TATABOX2 motif having the consensus sequence TATAAAT (SEQ ID NO:78). See, Shirsat et al., *Mol Gen Genet* 215:326-331 (1989); Grace et al., *Biol Chem* 279:8102-8110 (2004). A regulatory region can contain a TATABOX3 motif having the consensus sequence TATTAAT (SEQ ID NO:79). See, PLACE (PLAnt Cis-acting regulatory DNA Elements) at dna.affrc.go.jp/PLCAE/signalscan.html). A regulatory region can contain a TATABOX4 motif having the consensus sequence TATATAA (SEQ ID NO:80). See, Grace et al., *J Biol Chem* 279:8102-8110 (2004). A regulatory region can contain a TATABOX5 motif having the consensus sequence TTATTT (SEQ ID NO:81). See, Tjaden et al., *Plant Physiol* 108:1109-1117 (1995). A regulatory region can contain a TATABOXOSPAL motif having the consensus sequence TATTTAA (SEQ ID NO:82). See, Zhu et al., *Plant Cell* 14: 795-803 (2002). A regulatory region can contain a TELOBOXATEEF1AA1 motif having the consensus sequence AAACCCTAA (SEQ ID NO:83). See, Tremousayque et al., *Plant J* 20: 553-561 (1999); Axelos et al., *Mol Gen Genet* 219: 106-112 (1989); Welchen and Gonzalez, *Plant Physiol* 139: 88-100 (2005). A regulatory region can contain a TL1ATSAR motif having the consensus sequence CTGAAGAAGAA (SEQ ID NO:84). See, Wang et al., *Science* 308: 1036-1040 (2005). A regulatory region can contain a UP2ATMSD motif having the consensus sequence AAACCCTA (SEQ ID NO:85). See, Tatematsu et al., *Plant Physiology* 138: 757-766 (2005). A regulatory region can contain a WBBOXPCWRKY1 motif having the consensus sequence TTTGACY (SEQ ID NO:86). See, Ishiguro and Nakamura, *Mol Gen Genet* 244:563-571 (1994); Rushton et al., *Plant Mol Biol* 29:691-702 (1995); Rushon et al., *EMBO J* 15:5690-5700 (1996); de Pater et al., *Nucleic Acids Res* 24:4624-4631 (1996); Eulgem et al., *Trends Plant Sci* 5: 199-206 (2000). A regulatory region can contain a XYLAT motif having the consensus sequence ACAAAGAA (SEQ ID NO:87). See, Ko et al., *Mol Genet Genomics* 276:517-531 (2006).

Stringency: "Stringency," as used herein is a function of nucleic acid molecule probe length, nucleic acid molecule probe composition (G+C content), salt concentration, organic solvent concentration and temperature of hybridization and/or wash conditions. Stringency is typically measured by the parameter $T_m$, which is the temperature at which 50% of the complementary nucleic acid molecules in the hybridization assay are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship between hybridization conditions and $T_m$ (in ° C.) is expressed in the mathematical equation:

$$T_m=81.5-16.6(\log_{10}[Na^+])+0.41(\%G+C)-(600/N) \quad (I)$$

where N is the number of nucleotides of the nucleic acid molecule probe. This equation works well for probes 14 to 70 nucleotides in length that are identical to the target sequence. The equation below, for $T_m$ of DNA-DNA hybrids, is useful for probes having lengths in the range of 50 to greater than 500 nucleotides, and for conditions that include an organic solvent (formamide):

$$T_m=81.5+16.6 \log \{[Na^+]/(1+0.7[Na^+])\}+0.41(\%G+C)-500/L\ 0.63(\%\ \text{formamide}) \quad (II)$$

where L represents the number of nucleotides in the probe in the hybrid (21). The $T_m$ of Equation II is affected by the nature of the hybrid: for DNA-RNA hybrids, $T_m$ is 10-15° C. higher than calculated; for RNA-RNA hybrids, $T_m$ is 20-25° C. higher. Because the $T_m$ decreases about 1° C. for each 1% decrease in homology when a long probe is used (Frischauf et al. (1983) *J. Mol Biol*, 170: 827-842), stringency conditions can be adjusted to favor detection of identical genes or related family members.

Equation II is derived assuming the reaction is at equilibrium. Therefore, hybridizations according to the present invention are most preferably performed under conditions of probe excess and allowing sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction, or after hybridization has occurred, by altering the salt and temperature conditions of the wash solutions. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

To: The term "$T_0$" refers to the whole plant, explant or callus tissue, inoculated with the transformation medium.

$T_1$: The term $T_1$ refers to either the progeny of the $T_0$ plant, in the case of whole-plant transformation, or the regenerated seedling in the case of explant or callous tissue transformation.

$T_2$: The term $T_2$ refers to the progeny of the $T_1$ plant. $T_2$ progeny are the result of self-fertilization or cross-pollination of a $T_1$ plant.

$T_3$: The term $T_3$ refers to second generation progeny of the plant that is the direct result of a transformation experiment. $T_3$ progeny are the result of self-fertilization or cross-pollination of a $T_2$ plant.

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present invention, a "translational start site" is usually an ATG or AUG in a transcript, often the first ATG or AUG. A single protein encoding transcript, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation.

Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

2. Use of the Promoters of the Invention

The promoters and promoter control elements of this invention are capable of modulating transcription. Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:
 (i) antisense;
 (ii) ribozymes;
 (iii) coding sequences; or
 (iv) fragments thereof.

The promoter also can modulate transcription in a host genome in cis- or in trans-.

In an organism, such as a plant, the promoters and promoter control elements of the instant invention are useful to produce preferential transcription which results in a desired pattern of transcript levels in a particular cells, tissues, or organs, or under particular conditions.

4. Identifying and Isolating Promoter Sequences of the Invention

The promoters and promoter control elements of the present invention are presented in the Promoter Reports of the Tables and were identified from *Arabidopsis thaliana* and *Oryza sativa*. Isolation from genomic libraries of polynucleotides comprising the sequences of the promoters and promoter control elements of the present invention is possible using known techniques. For example, polymerase chain reaction (PCR) can amplify the desired polynucleotides utilizing primers designed from SEQ ID NOs: 1-26 or residues 601-1000 of SEQ ID NO: 26. Polynucleotide libraries comprising genomic sequences can be constructed according to Sambrook et al., *Molecular Cloning: A Laboratory Manual*, 2$^{nd}$ Ed. (1989) Cold Spring Harbor Press, Cold Spring Harbor, N.Y.), for example.

Other procedures for isolating polynucleotides comprising the promoter sequences of the invention include, without limitation, tail-PCR, and 5' rapid amplification of cDNA ends (RACE). See, for tail-PCR, for example, Liu et al. (1995) *Plant J* 8(3): 457-463; Liu et al. (1995) *Genomics* 25: 674-681; Liu et al. (1993) *Nucl. Acids Res.* 21(14): 3333-3334; and Zoe et al. (1999) *BioTechniques* 27(2): 240-248; for RACE, see, for example, *PCR Protocols: A Guide to Methods and Applications*, (1990) Academic Press, Inc.

In addition, the promoters and promoter control elements described in the Promoter Reports in the Tables (SEQ. ID. Nos. 1-26) can be chemically synthesized according to techniques in common use. See, for example, Beaucage et al. (1981) *Tet. Lett.* 22: 1859 and U.S. Pat. No. 4,668,777. Such chemical oligonucleotide synthesis can be carried out using commercially available devices, such as, Biosearch 4600 or 8600 DNA synthesizer, by Applied Biosystems, a division of Perkin-Elmer Corp., Foster City, Calif., USA; and Expedite by Perceptive Biosystems, Framingham, Mass., USA.

Included in the present invention are promoters exhibiting nucleotide sequence identity to SEQ. ID. Nos. 1-26 or nucleic acid residues 601-1000 of SEQ ID NO: 26 namely that exhibits at least 80% sequence identity, at least 85%, at least 90%, and at least 95%, 96%, 97%, 98% or 99% sequence identity compared to SEQ. ID. Nos. 1-26 or residues 601-1000 of SEQ ID NO: 26. Such sequence identity can be calculated by the algorithms and computers programs described above.

The present invention further encompasses "functional variants" or "function fragments" of the disclosed sequences, particularly fragments of SEQ ID NOs: 1-26 and residues 601-1000 of SEQ ID NO: 5 that retain promoter activity. Functional variants include, for example, regulatory sequences of the invention having one or more nucleotide substitutions, deletions or insertions and wherein the variant retains promoter activity. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described at U.S. Pat. No. 6,844,484, Northern blot analysis, or similar techniques. The '484 patent describes the identification of functional variants of different promoters.

Functional fragment, that is, a regulatory sequence fragment can be formed by one or more deletions from a larger regulatory element. For example, in some instances, the 5' portion of a promoter up to the TATA box near the transcription start site can be deleted without abolishing promoter activity, as described by Opsahl-Sorteberg, H-G. et al., "Identification of a 49-bp fragment of the HvLTP2 promoter directing aleruone cell specific expression" Gene 341:49-58 (2004). Such fragments should retain promoter activity, particularly the ability to drive expression of operably linked nucleotide sequences. Activity can be measured by Northern blot analysis, reporter activity measurements when using transcriptional fusions, and the like. See, for example, Sambrook et al., Molecular Cloning, A laboratory Manual (1989). Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis et al., Methods Enzymol., 155:335-350 (1987) and Erlich, ed., PCR Technology (Stockton Press, New York), (1989).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

5. Testing of Promoters

Promoters of the invention, including functional fragments, are tested for activity by cloning the sequence into an appropriate vector, transforming plants with the construct and assaying for marker gene expression. Recombinant DNA constructs are prepared which comprise the promoter sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) *Proc. Natl. Acad. Sci. USA* 89: 8794-8797; Hamilton et al. (1996) Proc. *Natl. Acad. Sci. USA* 93: 9975-9979;
(b) YAC: Burke et al. (1987) *Science* 236:806-812;
(c) PAC: Sternberg N. et al. (1990) Proc Natl Acad Sci USA. 87(1):103-7;
(d) Bacteria-Yeast Shuttle Vectors: Bradshaw et al. (1995) *Nucl Acids Res* 23: 4850-4856;
(e) Lambda Phage Vectors: Replacement Vector, e.g., Frischauf et al. (1983) *J. Mol Biol* 170: 827-842; or Insertion vector, e.g., Huynh et al. (1985) In: Glover N M (ed) *DNA Cloning: A practical Approach*, Vol. 1 Oxford: IRL Press; T-DNA gene fusion vectors: Walden et al. (1990) *Mol Cell Biol* 1: 175-194; and
(g) Plasmid vectors: Sambrook et al., infra.

Typically, the construct comprises a vector containing a promoter sequence of the present invention operationally linked to any marker gene. The promoter was identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin. Vectors can also include origins of replication, scaffold attachment regions (SARs), markers, homologous sequences, introns, etc.

6. Constructing Promoters with Control Elements

6.1 Combining Promoters and Promoter Control Elements

The promoter and promoter control elements of the present invention, both naturally occurring and synthetic, can be used alone or combined with each other to produce the desired preferential transcription. Also, the promoters of the invention can be combined with other known sequences to obtain other useful promoters to modulate, for example, tissue transcription specific or transcription specific to certain conditions. Such preferential transcription can be determined using the techniques or assays described above.

Promoters can contain any number of control elements. For example, a promoter can contain multiple transcription binding sites or other control elements. One element may confer tissue or organ specificity; another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

The following are promoters that are induced under stress conditions and can be combined with those of the present invention: 1dh1 (oxygen stress; tomato; see Germain and Ricard (1997) *Plant Mol Biol* 35:949-54), GPx and CAT (oxygen stress; mouse; see Franco et al. (1999) *Free Radic Biol Med* 27:1122-32), ci7 (cold stress; potato; see Kirch et al. (1997) *Plant Mol Biol.* 33:897-909), Bz2 (heavy metals; maize; see Marrs and Walbot (1997) *Plant Physiol* 113:93-102), HSP32 (hyperthermia; rat; see Raju and Maines (1994) *Biochim Biophys Acta* 1217:273-80), and MAP-KAPK-2 (heat shock; *Drosophila*; see Larochelle and Suter (1995) *Gene* 163:209-14).

In addition, the following examples of promoters are induced by the presence or absence of light can be used in combination with those of the present invention: Topoisomerase II (pea; see Reddy et al. (1999) *Plant Mol Biol* 41:125-37), chalcone synthase (soybean; see Wingender et al. (1989) *Mol Gen Genet* 218:315-22) mdm2 gene (human tumor; see Saucedo et al. (1998) *Cell Growth Differ* 9:119-30), Clock and BMAL1 (rat; see Namihira et al. (1999) *Neurosci Lett* 271:1-4, PHYA (*Arabidopsis*; see Canton and Quail (1999) *Plant Physiol* 121:1207-16), PRB-1b (tobacco; see Sessa et al. (1995) *Plant Mol Biol* 28:537-47) and Ypr10 (common bean; see Walter et al. (1996) *Eur J Biochem* 239:281-93).

The promoters and control elements of the following genes can be used in combination with the present invention to confer tissue specificity: MipB (iceplant; Yamada et al. (1995) *Plant Cell* 7:1129-42) and SUCS (root nodules; broadbean; Kuster et al. (1993) *Mol Plant Microbe Interact* 6:507-14) for roots, OsSUT1 (rice; Hirose et al. (1997) *Plant Cell Physiol* 38:1389-96) for leaves, Msg (soybean; Stomvik et al. (1999) *Plant Mol Biol* 41:217-31) for siliques, cell (*Arabidopsis*; Shani et al. (1997) *Plant Mol Biol* 34(6):837-42) and ACT11 (*Arabidopsis*; Huang et al. (1997) *Plant Mol Biol* 33:125-39) for inflorescence.

Still other promoters are affected by hormones or participate in specific physiological processes, which can be used in combination with those of present invention. Some examples are the ACC synthase gene that is induced differently by ethylene and brassinosteroids (mung bean; Yi et al. (1999) *Plant Mol Biol* 41:443-54), the TAPG1 gene that is active during abscission (tomato; Kalaitzis et al. (1995) *Plant Mol Biol* 28:647-56), and the 1-aminocyclopropane-1-carboxylate synthase gene (carnation; Jones et al. (1995) *Plant Mol Biol* 28:505-12) and the CP-2/cathepsin L gene (rat; Kim and Wright (1997) *Biol Reprod* 57:1467-77), both active during senescence.

Spacing between control elements or the configuration or control elements can be determined or optimized to permit the desired protein-polynucleotide or polynucleotide interactions to occur.

For example, if two transcription factors bind to a promoter simultaneously or relatively close in time, the binding sites are spaced to allow each factor to bind without steric hindrance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to hairpin or loop to permit the two elements to bind. The spacing between two such hybridizing control elements can be as small as a t-RNA loop, to as large as 10 kb.

Typically, the spacing is no smaller than 5 bases; more typically, no smaller than 8; more typically, no smaller than 15 bases; more typically, no smaller than 20 bases; more typically, no smaller than 25 bases; even more typically, no smaller than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases. In some embodiments, the nucleic acid of the invention comprises at least one fragment of YP0286 (SEQ ID NO:5), e.g., YP2219 (SEQ ID NO:4), with the proviso that said nucleic acid does not consist of YP0286 (SEQ ID NO:5).

Such spacing between promoter control elements can be determined using the techniques and assays described above.

6.2 Vectors Used to Transform Cells/Hosts

A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation (U.S. Pat. No. 5,384,253); microprojectile bombardment (U.S. Pat. No. 5,015,580; U.S. Pat. No. 5,550,318; U.S. Pat. No. 5,538,880; U.S. Pat. No. 6,160,208; U.S. Pat. No. 6,399,861; and U.S. Pat. No. 6,403,865); *Agrobacterium*-mediated transformation (U.S. Pat. No. 5,824,877; U.S. Pat. No. 5,591,616; U.S. Pat. No. 5,981,840; and U.S. Pat. No. 6,384,301); and protoplast transformation (U.S. Pat. No. 5,508,184).

The present promoters and/or promoter control elements may be delivered to a system such as a cell by way of a vector. For the purposes of this invention, such delivery may range from simply introducing the promoter or promoter control element by itself randomly into a cell to integration of a cloning vector containing the present promoter or promoter control element. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are a preferred vector for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al. (1985) *Nature* 317: 741-744; Gordon-Kamm et al. (1990) *Plant Cell* 2: 603-618; and Stalker et al. (1988) *Science* 242: 419-423). Other marker genes exist which provide hormone responsiveness.

The promoter or promoter control element of the present invention may be operably linked to a polynucleotide to be transcribed. In this manner, the promoter or promoter control element may modify transcription by modulating transcript levels of that polynucleotide when inserted into a genome.

However, prior to insertion into a genome, the promoter or promoter control element need not be linked, operably or otherwise, to a polynucleotide to be transcribed. For example, the promoter or promoter control element may be inserted alone into the genome in front of a polynucleotide already present in the genome. In this manner, the promoter or promoter control element may modulate the transcription of a polynucleotide that was already present in the genome. This polynucleotide may be native to the genome or inserted at an earlier time.

Alternatively, the promoter or promoter control element may be inserted into a genome alone to modulate transcription. See, for example, Vaucheret, H et al. (1998) *Plant J* 16: 651-659. Rather, the promoter or promoter control element may be simply inserted into a genome or maintained extra-chromosomally as a way to divert transcription resources of the system to itself. This approach may be used to down-regulate the transcript levels of a group of polynucleotide(s).

The nature of the polynucleotide to be transcribed is not limited. Specifically, the polynucleotide may include sequences that will have activity as RNA as well as sequences that result in a polypeptide product. These sequences may include, but are not limited to antisense sequences, RNAi sequences, ribozyme sequences, spliceosomes, amino acid coding sequences, and fragments thereof. Specific coding sequences may include, but are not limited to endogenous proteins or fragments thereof, or heterologous proteins including marker genes or fragments thereof.

Constructs of the present invention would typically contain a promoter operably linked to a transcribable nucleic acid molecule operably linked to a 3' transcription termination nucleic acid molecule. In addition, constructs may include but are not limited to additional regulatory nucleic acid molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA nucleic acid molecule which can play an important role in translation initiation and can also be a genetic component in a plant expression construct. For example, non-translated 5' leader nucleic acid molecules derived from heat shock protein genes have been demonstrated to enhance gene expression in plants (see for example, U.S. Pat. No. 5,659,122 and U.S. Pat. No. 5,362,865, all of which are hereby incorporated by reference). These additional upstream and downstream regulatory nucleic acid molecules may be derived from a source that is native or heterologous with respect to the other elements present on the promoter construct.

Thus, one embodiment of the invention is a promoter such as provided in SEQ ID NOs: 1-26 or residues 601-1000 of SEQ ID NO: 26, operably linked to a transcribable nucleic acid molecule so as to direct transcription of said transcribable nucleic acid molecule at a desired level or in a desired tissue or developmental pattern upon introduction of said construct into a plant cell. In some cases, the transcribable nucleic acid molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable nucleic acid molecules for incorporation into constructs of the present invention include, for example, nucleic acid molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or nucleic acid molecule that is introduced into a recipient cell. The type of nucleic acid molecule included in the exogenous nucleic acid molecule can include a nucleic acid molecule that is already present in the plant cell, a nucleic acid molecule from another plant, a nucleic acid molecule from a different organism, or a nucleic acid molecule generated externally, such as a nucleic acid molecule containing an antisense message of a gene, or a nucleic acid molecule encoding an artificial or modified version of a gene.

The promoters of the present invention can be incorporated into a construct using marker genes as described, and tested in transient analyses that provide an indication of gene expression in stable plant systems. As used herein the term "marker gene" refers to any transcribable nucleic acid molecule whose expression can be screened for or scored in some way. Methods of testing for marker gene expression in transient assays are known to those of skill in the art. Transient expression of marker genes has been reported using a variety of plants, tissues, plant cell(s), and DNA delivery systems. For example, types of transient analyses can include but are not limited to direct gene delivery via electroporation or particle bombardment of tissues in any transient plant assay using any plant species of interest. Such transient systems would include, but are not limited to, electroporation of protoplasts from a variety of tissue sources or particle bombardment of specific tissues of interest. The present invention encompasses the use of any transient expression system to evaluate promoters or promoter fragments operably linked to any transcribable nucleic acid molecules, including but not limited to selected reporter genes, marker genes, or genes of agronomic interest. Examples of plant tissues envisioned to test in transients via an appropriate delivery system would include, but are not limited to, leaf base tissues, callus, cotyledons, roots, endosperm, embryos, floral tissue, pollen, and epidermal tissue.

Promoters and control elements of the present invention are useful for modulating metabolic or catabolic processes. Such processes include, but are not limited to, secondary product metabolism, amino acid synthesis, seed protein storage, increased biomass, oil development, pest defense and nitrogen usage. Some examples of genes, transcripts and peptides or polypeptides participating in these processes, which can be modulated by the present invention: are tryptophan decarboxylase (tdc) and strictosidine synthase (str1), dihydrodipicolinate synthase (DHDPS) and aspartate kinase (AK), 2S albumin and alpha-, beta-, and gamma-zeins, ricinoleate and 3-ketoacyl-ACP synthase (KAS), Bacillus thuringiensis (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

As explained above, several types of regulatory elements exist concerning transcription regulation. Each of these regulatory elements may be combined with the present vector if desired. Translation of eukaryotic mRNA is often initiated at the codon that encodes the first methionine. Thus, when constructing a recombinant polynucleotide according to the present invention for expressing a protein product, it is preferable to ensure that the linkage between the 3' portion, preferably including the TATA box, of the promoter and the polynucleotide to be transcribed, or a functional derivative thereof, does not contain any intervening codons which are capable of encoding a methionine.

The vector of the present invention may contain additional components. For example, an origin of replication allows for replication of the vector in a host cell. Additionally, homologous sequences flanking a specific sequence allow for specific recombination of the specific sequence at a desired location in the target genome. T-DNA sequences also allow for insertion of a specific sequence randomly into a target genome.

The vector may also be provided with a plurality of restriction sites for insertion of a polynucleotide to be transcribed as well as the promoter and/or promoter control elements of the present invention. The vector may additionally contain selectable marker genes. The vector may also contain a transcriptional and translational initiation region, and a transcriptional and translational termination region functional in the host cell. The termination region may be native with the transcriptional initiation region, may be native with the polynucleotide to be transcribed, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; Joshi et al. (1987) *Nucleic Acid Res.* 15:9627-9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436,391; see also and Murray et al. (1989) *Nucleic Acids Res.* 17:477-498.

Additional sequence modifications include elimination of sequences encoding spurious polyadenylation signals, exon intron splice site signals, transposon-like repeats, and other such sequences well characterized as deleterious to expression. The G-C content of the polynucleotide may be adjusted to levels average for a given cellular host, as calculated by reference to known genes expressed in the host cell. The polynucleotide sequence may be modified to avoid hairpin secondary mRNA structures.

A general description of expression vectors and reporter genes can be found in Gruber, et al. (1993) "Vectors for Plant Transformation" *In Methods in Plant Molecular Biology & Biotechnology*, Glich et al. Eds. pp. 89-119, CRC Press. Moreover GUS expression vectors and GUS gene cassettes are available from Clonetech Laboratories, Inc., Palo Alto, Calif. while luciferase expression vectors and luciferase gene cassettes are available from Promega Corp. (Madison, Wis.). GFP vectors are available from Aurora Biosciences.

6.3 Polynucleotide Insertion into a Host Cell

The promoters according to the present invention can be inserted into a host cell. A host cell includes but is not limited to a plant, mammalian, insect, yeast, and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

The promoters of the present invention can exist autonomously or independent of the host cell genome. Vectors of these types are known in the art and include, for example, certain type of non-integrating viral vectors, autonomously replicating plasmids, artificial chromosomes, and the like.

Additionally, in some cases transient expression of a promoter may be desired.

The promoter sequences, promoter control elements or vectors of the present invention may be transformed into host cells. These transformations may be into protoplasts or intact tissues or isolated cells. Preferably expression vectors are introduced into intact tissue. General methods of culturing plant tissues are provided for example by Maki et al. (1993) "Procedures for Introducing Foreign DNA into Plants" In *Methods in Plant Molecular Biology & Biotechnology*, Glich et al. Eds. pp. 67-88 CRC Press; and by Phillips et al. (1988) "Cell-Tissue Culture and In-Vitro Manipulation" In *Corn & Corn Improvement*, 3rd Edition Sprague et al. eds., pp. 345-387, American Society of Agronomy Inc. et al.

Methods of introducing polynucleotides into plant tissue include the direct infection or co-cultivation of plant cell with *Agrobacterium tumefaciens*, Horsch et al. (1985) *Science*, 227:1229. Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al., "Direct DNA transfer into intact plant cells via microprojectile bombardment" In: Gamborg and Phillips (Eds.) *Plant Cell*, Tissue and Organ Culture: Fundamental Methods, Springer Verlag, Berlin (1995).

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. species: *Agrostis stolonifera*, *Poa pratensis*, *Stenotaphrum secundatum*); wheat (*Triticum aestivum*), switchgrass (*Panicum vigatum*) and alfalfa (*Medicago sativa*). It is apparent to those of skill in the art that a number of transformation methodologies can be used and modified for production of stable transgenic plants from any number of target plants of interest.

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Cathranthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species include *Panicum* spp. or hybrids thereof, *Sorghum* spp. or hybrids thereof, sudangrass, *Miscanthus* spp. or hybrids thereof, *Saccharum* spp. or hybrids thereof, *Erianthus* spp., *Populus* spp., *Andropogon gerardii* (big bluestem), *Pennisetum purpureum* (elephant grass) or hybrids thereof (e.g., *Pennisetum purpureum*×*Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrids thereof, *Secale cereale* (rye), *Salix* spp. (willow), *Eucalyptus* spp. (eucalyptus), Triticosecale (*Triticum*—wheat×rye), *Tripsicum dactyloides* (Eastern gammagrass), *Leymus cinereus* (basin wildrye), *Leymus condensatus* (giant wildrye), and bamboo.

In some embodiments, a suitable species can be a wild, weedy, or cultivated *sorghum* species such as, but not limited to, *Sorghum almum, Sorghum ampium, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sor-*

*ghum vulgare*, or hybrids such as *Sorghum×almum, Sorghum×sudangrass* or *Sorghum×drummondii*.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea spp., Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium*.

Suitable species also include *Parthenium argentatum* (guayule), *Hevea* spp. (rubber), *Mentha spicata* (mint), *Mentha piperita* (mint), *Bixa orellana,* and *Alstroemeria* spp.

Suitable species also include *Rosa* spp. (rose), *Dianthus caryophyllus* (carnation), *Petunia* spp. (*petunia*) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple, *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus,* and *Ricinus;* and the monocot genera *Elaeis, Festuca, Hordeum, Lolium, Oryza, Panicum, Pennisetum, Phleum, Poa, Saccharum, Secale, Sorghum, Triticosecale, Triticum,* and *Zea.* In some embodiments, a plant is a member of the species *Panicum virgatum* (switchgrass), *Sorghum bicolor* (*sorghum,* sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp.× *Miscanthus* sp., *Panicum virgatum×Panicum amarum, Panicum virgatum×Panicum amarulum,* and *Pennisetum purpureum×Pennisetum typhoidum*).

In another embodiment of the current invention, expression constructs can be used for gene expression in callus culture for the purpose of expressing marker genes encoding peptides or polypeptides that allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media. Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP), and β-glucuronidase (GUS), etc. Some of the promoters provided in SEQ ID NOs: 1-26 or nucleic acid residues 601-1000 of SEQ ID NO: 26 will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the cre-lox system (A. C. Vergunst et al. (1998) *Plant Mol. Biol.* 38:393).

7. Uses of the Promoters of the Invention 7.1 Use of the Promoters to Study and Screen for Expression The promoters of the present invention can be used to further understand developmental mechanisms. For example, promoters that are specifically induced during callus formation, somatic embryo formation, shoot formation or root formation can be used to explore the effects of overexpression, repression or ectopic expression of target genes, or for isolation of trans-acting factors.

The vectors of the invention can be used not only for expression of coding regions but may also be used in exon-trap cloning, or promoter trap procedures to detect differential gene expression in various tissues (see Lindsey et al. (1993) *Transgenic Research* 2:3347. Auch and Reth (1990) *Nucleic Acids Research* 18: 6743).

Entrapment vectors, first described for use in bacteria (Casadaban and Cohen (1979) *Proc. Nat. Aca. Sci. U.S.A.* 76: 4530; Casadaban et al. (1980) *J. Bacteriol.* 143: 971) permit selection of insertional events that lie within coding sequences. Entrapment vectors can be introduced into pluripotent ES cells in culture and then passed into the germline via chimeras (Gossler et al. aaa91989) *Science* 244: 463; Skarnes (1990) *Biotechnology* 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, broadly active constructs can be eliminated by screening only bacteria that do not express the reporter gene under laboratory conditions. The bacteria selected by such a method contain constructs that are selectively induced only during infection of the host. The IVET approach can be modified for use in plants to identify genes induced in either the bacteria or the plant cells upon pathogen infection or root colonization. For information on IVET see the articles by Mahan et al. (1993) *Science* 259:686-688, Mahan et al. (1995) *Proc. Natl. Acad. Sci. USA* 92:669-673, Heithoff et al. (1997) *Proc. Natl. Acad. Sci USA* 94:934-939, and Wang et al. (1996) *Proc. Natl. Acad. Sci USA* 93:10434.

7.2 Use of the Promoters to Transcribe Genes of Interest

In one embodiment of the invention, a nucleic acid molecule as shown in SEQ ID NOs: 1-26 or nucleic acid residues 601-1000 of SEQ ID NO: 26 is, incorporated into a construct such that a promoter of the present invention is operably linked to a transcribable nucleic acid molecule that is a gene of agronomic interest. As used herein, the term "gene of agronomic interest" refers to a transcribable nucleic acid molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance, increased yield, increased biomass, insect control, fungal disease resistance, virus resistance, nematode resistance, bacterial disease resistance, starch production, modified oils production, high oil production, modified fatty acid content, high protein production, fruit ripening, enhanced animal and human nutrition, biopolymers, environmental stress resistance, pharmaceutical peptides, improved processing traits, improved digestibility, industrial enzyme production, improved flavor, nitrogen fixation, hybrid seed production, and biofuel production. The genetic elements, methods, and transgenes described in the patents listed above are hereby incorporated by reference.

Alternatively, a transcribable nucleic acid molecule can effect the above mentioned phenotypes by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any nucleic acid molecule that encodes a protein or mRNA that expresses a phenotype or morphology change of interest may be useful for the practice of the present invention.

7.3. Stress Induced Preferential Transcription

Promoters and control elements providing modulation of transcription under oxidative, drought, oxygen, wound, and methyl jasmonate stress are particularly useful for producing host cells or organisms that are more resistant to biotic and abiotic stresses. In a plant, for example, modulation of genes, transcripts, and/or polypeptides in response to oxidative stress can protect cells against damage caused by oxidative agents, such as hydrogen peroxide and other free radicals.

Drought induction of genes, transcripts, and/or polypeptides are useful to increase the viability of a plant, for example, when water is a limiting factor. In contrast, genes, transcripts, and/or polypeptides induced during oxygen stress can help the flood tolerance of a plant.

The promoters and control elements of the present invention can modulate stresses similar to those described in, for example, stress conditions are VuPLD1 (drought stress; Cowpea; see Pham-Thi et al. (1999) *Plant Mol Biol* 39:1257-65), pyruvate decarboxylase (oxygen stress; rice; see Rivosal et al. (1997) *Plant Physiol* 114(3): 1021-29), chromoplast specific carotenoid gene (oxidative stress; *Capsicum*; see Bouvier et al. (1998) *J Biol Chem* 273: 30651-59).

Promoters and control elements providing preferential transcription during wounding or induced by methyl jasmonate can produce a defense response in host cells or organisms. In a plant, for example, preferential modulation of genes, transcripts, and/or polypeptides under such conditions is useful to induce a defense response to mechanical wounding, pest or pathogen attack or treatment with certain chemicals.

Promoters and control elements of the present invention also can trigger a response similar to those described for cf9 (viral pathogen; tomato; see O'Donnell et al. (1998) Plant J 14(1): 137-42), hepatocyte growth factor activator inhibitor type 1 (HAI-1), which enhances tissue regeneration (tissue injury; human; Koono et al. (1999) *J Histochem Cytochem* 47: 673-82), copper amine oxidase (CuAO), induced during ontogenesis and wound healing (wounding; chick-pea; Rea et al. (1998) *FEBS Lett* 437: 177-82), proteinase inhibitor II (wounding; potato; see Pena-Cortes et al. (1988) *Planta* 174: 84-89), protease inhibitor II (methyl jasmonate; tomato; see Farmer and Ryan (1990) *Proc Natl Acad Sci USA* 87: 7713-7716), two vegetative storage protein genes VspA and VspB (wounding, jasmonic acid, and water deficit; soybean; see Mason and Mullet (1990) *Plant Cell* 2: 569-579).

Up-regulation and transcription down-regulation are useful for these applications. For instance, genes, transcripts, and/or polypeptides that increase oxidative, flood, or drought tolerance may require up-regulation of transcription.

Typically, promoter or control elements, which provide preferential transcription in wounding or under methyl jasmonate induction, produce transcript levels that are statistically significant as compared to cell types, organs or tissues under other conditions.

For preferential up-regulation of transcription, promoter and control elements produce transcript levels that are above background of the assay.

7.4. Light Induced Preferential Transcription

Promoters and control elements providing preferential transcription when induced by light exposure can be utilized to modulate growth, metabolism, and development; to increase drought tolerance; and decrease damage from light stress for host cells or organisms. In a plant, for example, modulation of genes, transcripts, and/or polypeptides in response to light is useful
  (1) to increase the photosynthetic rate;
  (2) to increase storage of certain molecules in leaves or green parts only, e.g. silage with high protein or starch content;
  (3) to modulate production of exogenous compositions in green tissue, e.g. certain feed enzymes;
  (4) to induce growth or development, such as fruit development and maturity, during extended exposure to light;
  (5) to modulate guard cells to control the size of stomata in leaves to prevent water loss, or
  (6) to induce accumulation of beta-carotene to help plants cope with light induced stress.

The promoters and control elements of the present invention also can trigger responses similar to those described in: abscisic acid insensitive3 (ABI3) (dark-grown *Arabidopsis* seedlings, see Rohde et al. (2000) *Plant Cell* 12: 35-52), asparagine synthetase (pea root nodules, see Tsai and Coruzzi (1990) *EMBO J* 9: 323-32), mdm2 gene (human tumor, see Saucedo et al. (1998) *Cell Growth Differ* 9: 119-30).

Up-regulation and transcription down-regulation are useful for these applications. For instance, genes, transcripts, and/or polypeptides that increase drought or light tolerance may require up-regulation of transcription.

Typically, promoter or control elements, which provide preferential transcription in cells, tissues or organs exposed to light, produce transcript levels that are statistically significant as compared to cells, tissues, or organs under decreased light exposure (intensity or length of time).

For preferential up-regulation of transcription, promoter and control elements produce transcript levels that are above background of the assay.

7.5. Dark Induced Preferential Transcription

Promoters and control elements providing preferential transcription when induced by dark or decreased light intensity or decreased light exposure time can be utilized to time growth, metabolism, and development, to modulate photosynthesis capabilities for host cells or organisms. In a plant, for example, modulation of genes, transcripts, and/or polypeptides in response to dark is useful, for example,
  (1) to induce growth or development, such as fruit development and maturity, despite lack of light;
  (2) to modulate genes, transcripts, and/or polypeptide active at night or on cloudy days; or
  (3) to preserve the plastid ultra structure present at the onset of darkness.

The present promoters and control elements can also trigger response similar to those described in the section above.

Up-regulation and transcription down-regulation is useful for these applications. For instance, genes, transcripts, and/ or polypeptides that increase or decrease growth and development may require up-regulation of transcription.

Typically, promoter or control elements, which provide preferential transcription under exposure to dark or decrease light intensity or decrease exposure time, produce transcript levels that are statistically significant.

For preferential up-regulation of transcription, promoter and control elements produce transcript levels that are above background of the assay.

7.6. Leaf Preferential Transcription

Promoters and control elements providing preferential transcription in a leaf can modulate growth, metabolism, and development or modulate energy and nutrient utilization in host cells or organisms. In a plant, for example, preferential modulation of genes, transcripts, and/or polypeptide in a leaf, is useful, for example,
  (1) to modulate leaf size, shape, and development;
  (2) to modulate the number of leaves; or
  (3) to modulate energy or nutrient usage in relation to other organs and tissues Up-regulation and transcription down-regulation is useful for these applications. For instance, genes, transcripts, and/ or polypeptides that increase growth, for example, may require up-regulation of transcription.

Typically, promoter or control elements, which provide preferential transcription in the cells, tissues, or organs of a leaf, produce transcript levels that are statistically significant as compared to other cells, organs or tissues.

For preferential up-regulation of transcription, promoter and control elements produce transcript levels that are above background of the assay.

7.7. Root Preferential Transcription

Promoters and control elements providing preferential transcription in a root can modulate growth, metabolism, development, nutrient uptake, nitrogen fixation, or modulate energy and nutrient utilization in host cells or organisms. In a plant, for example, preferential modulation of genes, transcripts, and/or polypeptide in a root, is useful,
  (1) to modulate root size, shape, and development;
  (2) to modulate the number of roots, or root hairs;
  (3) to modulate mineral, fertilizer, or water uptake;
  (4) to modulate transport of nutrients; or
  (4) to modulate energy or nutrient usage in relation to other cells, organs and tissues.

Up-regulation and transcription down-regulation is useful for these applications. For instance, genes, transcripts, and/ or polypeptides that increase or decrease growth, for example, may require up-regulation of transcription.

Typically, promoter or control elements, which provide preferential transcription in cells, tissues, or organs of a root, produce transcript levels that are statistically significant as compared to other cells, organs or tissues.

For preferential up-regulation of transcription, promoter and control elements produce transcript levels that are above background of the assay.

7.8. Stem/Shoot Preferential Transcription

Promoters and control elements providing preferential transcription in a stem or shoot can modulate growth, metabolism, and development or modulate energy and nutrient utilization in host cells or organisms. In a plant, for example, preferential modulation of genes, transcripts, and/or polypeptide in a stem or shoot, is useful, for example,
  (1) to modulate stem/shoot size, shape, and development; or
  (2) to modulate energy or nutrient usage in relation to other organs and tissues Up-regulation and transcription down-regulation is useful for these applications. For instance, genes, transcripts, and/or polypeptides that increase growth, for example, may require up-regulation of transcription.

Typically, promoter or control elements, which provide preferential transcription in the cells, tissues, or organs of a stem or shoot, produce transcript levels that are statistically significant as compared to other cells, organs or tissues.

For preferential up-regulation of transcription, promoter and control elements produce transcript levels that are above background of the assay.

7.9. Fruit and Seed Preferential Transcription

Promoters and control elements providing preferential transcription in a silique or fruit can time growth, development, or maturity; or modulate fertility; or modulate energy and nutrient utilization in host cells or organisms. In a plant, for example, preferential modulation of genes, transcripts, and/or polypeptides in a fruit, is useful
  (1) to modulate fruit size, shape, development, and maturity;
  (2) to modulate the number of fruit or seeds;
  (3) to modulate seed shattering;
  (4) to modulate components of seeds, such as, storage molecules, starch, protein, oil, vitamins, anti-nutritional components, such as phytic acid;
  (5) to modulate seed and/or seedling vigor or viability;
  (6) to incorporate exogenous compositions into a seed, such as lysine rich proteins;
  (7) to permit similar fruit maturity timing for early and late blooming flowers; or
  (8) to modulate energy or nutrient usage in relation to other organs and tissues.

Up-regulation and transcription down-regulation is useful for these applications. For instance, genes, transcripts, and/or polypeptides that increase or decrease growth, for example, may require up-regulation of transcription.

Typically, promoter or control elements, which provide preferential transcription in the cells, tissues, or organs of siliques or fruits, produce transcript levels that are statistically significant as compared to other cells, organs or tissues.

For preferential up-regulation of transcription, promoter and control elements produce transcript levels that are above background of the assay.

7.10. Callus Preferential Transcription

Promoters and control elements providing preferential transcription in a callus can be useful to modulating transcription in dedifferentiated host cells. In a plant transformation, for example, preferential modulation of genes, transcripts, in callus is useful to modulate transcription of a marker gene, which can facilitate selection of cells that are transformed with exogenous polynucleotides.

Up-regulation and transcription down-regulation is useful for these applications. For instance, genes, transcripts, and/or polypeptides that increase marker gene detectability, for example, may require up-regulation of transcription.

For preferential up-regulation of transcription, promoter and control elements produce transcript levels that are above background of the assay.

7.11. Flower Specific Transcription

Promoters and control elements providing preferential transcription in flowers can modulate pigmentation; or modulate fertility in host cells or organisms. In a plant, for example, preferential modulation of genes, transcripts, and/or polypeptides in a flower, is useful,
  (1) to modulate petal color; or
  (2) to modulate the fertility of pistil and/or stamen.

Up-regulation and transcription down-regulation is useful for these applications. For instance, genes, transcripts, and/or polypeptides that increase or decrease pigmentation, for example, may require up-regulation of transcription Typically, promoter or control elements, which provide preferential transcription in flowers, produce transcript levels that are statistically significant as compared to other cells, organs or tissues.

For preferential up-regulation of transcription, promoter and control elements produce transcript levels that are above background of the assay.

7.12. Immature Bud and Inflorescence Preferential Transcription

Promoters and control elements providing preferential transcription in a immature bud or inflorescence can time growth, development, or maturity; or modulate fertility or viability in host cells or organisms. In a plant, for example, preferential modulation of genes, transcripts, and/or polypeptide in a immature bud and/or inflorescence, is useful,
  (1) to modulate embryo development, size, and maturity;
  (2) to modulate endosperm development, size, and composition;
  (3) to modulate the number of seeds and fruits; or
  (4) to modulate seed development and viability.

Up-regulation and transcription down-regulation is useful for these applications. For instance, genes, transcripts, and/or polypeptides that increase or decrease growth, for example, may require up-regulation of transcription.

Typically, promoter or control elements, which provide preferential transcription in immature buds and inflorescences, produce transcript levels that are statistically significant as compared to other cell types, organs or tissues.

For preferential up-regulation of transcription, promoter and control elements produce transcript levels that are above background of the assay.

7.13. Senescence Preferential Transcription

Promoters and control elements providing preferential transcription during senescence can be used to modulate cell degeneration, nutrient mobilization, and scavenging of free radicals in host cells or organisms. Other types of responses that can be modulated include, for example, senescence associated genes (SAG) that encode enzymes thought to be involved in cell degeneration and nutrient mobilization (*Arabidopsis*; see Hensel et al. (1993) *Plant Cell* 5: 553-64), and the CP-2/cathepsin L gene (rat; Kim and Wright (1997) *Biol Reprod* 57: 1467-77), both induced during senescence.

In a plant, for example, preferential modulation of genes, transcripts, and/or polypeptides during senescence is useful to modulate fruit ripening.

Up-regulation and transcription down-regulation is useful for these applications. For instance, genes, transcripts, and/or polypeptides that increase or decrease scavenging of free radicals, for example, may require up-regulation of transcription.

Typically, promoter or control elements, which provide preferential transcription in cells, tissues, or organs during senescence, produce transcript levels that are statistically significant as compared to other conditions.

For preferential up-regulation of transcription, promoter and control elements produce transcript levels that are above background of the assay.

7.14. Germination Preferential Transcription

Promoters and control elements providing preferential transcription in a germinating seed can time growth, development, or maturity; or modulate viability in host cells or organisms. In a plant, for example, preferential modulation of genes, transcripts, and/or polypeptide in a germinating seed, is useful,
(1) to modulate the emergence of the hypocotyls, cotyledons and radical; or
(2) to modulate shoot and primary root growth and development;

Up-regulation and transcription down-regulation is useful for these applications. For instance, genes, transcripts, and/or polypeptides that increase or decrease growth, for example, may require up-regulation of transcription.

Typically, promoter or control elements, which provide preferential transcription in a germinating seed, produce transcript levels that are statistically significant as compared to other cell types, organs or tissues.

For preferential up-regulation of transcription, promoter and control elements produce transcript levels that are above background of the assay.

8. GFP Experimental Procedures and Results

Procedures

The polynucleotide sequences of the present invention were tested for promoter activity using Green Fluorescent Protein (GFP) assays in the following manner.

Approximately 1-3 kb of genomic sequence occurring immediately upstream of the ATG translational start site of the gene of interest was isolated using appropriate primers tailed with BstXI restriction sites. Standard PCR reactions using these primers and genomic DNA were conducted. The resulting product was isolated, cleaved with BstXI and cloned into the BstXI site of an appropriate vector, such as pNewBin4-HAP1-GFP (see FIG. 1).

Agrobacterium-Mediated Transformation of Arabidopsis

Host Plants and Transgenes: Wild-type Arabidopsis thaliana Wassilewskija (WS) plants are transformed with Ti plasmids containing nucleic acid sequences to be expressed, as noted in the respective examples, in the sense orientation relative to the 35S promoter in a Ti plasmid. A Ti plasmid vector useful for these constructs, CRS 338, contains the Ceres-constructed, plant selectable marker gene phosphinothricin acetyltransferase (PAT), which confers herbicide resistance to transformed plants.

Ten independently transformed events are typically selected and evaluated for their qualitative phenotype in the $T_1$ generation.

Preparation of Soil Mixture: 24 L Sunshine Mix #5 soil (Sun Gro Horticulture, Ltd., Bellevue, Wash.) is mixed with 16 L Therm-O-Rock vermiculite (Therm-O-Rock West, Inc., Chandler, Ariz.) in a cement mixer to make a 60:40 soil mixture. To the soil mixture is added 2 Tbsp Marathon 1% granules (Hummert, Earth City, Mo.), 3 Tbsp OSMO-COTE® 14-14-14 (Hummert, Earth City, Mo.) and 1 Tbsp Peters fertilizer 20-20-20 (J.R. Peters, Inc., Allentown, Pa.), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of Agrobacterium: To 150 mL fresh YEB is added 0.1 mL each of carbenicillin, spectinomycin and rifampicin (each at 100 mg/ml stock concentration). Agrobacterium starter blocks are obtained (96-well block with Agrobacterium cultures grown to an $OD_{600}$ of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend Agrobacterium pellets. Infiltration media is prepared by adding 2.2 g MS salts, 50 g sucrose, and 5 pit 2 mg/ml benzylaminopurine to 900 ml water.

Dipping Infiltration: The pots are inverted and submerged for 5 minutes so that the aerial portion of the plant is in the Agrobacterium suspension. Plants are allowed to grow normally and seed is collected.

High-throughput Screening of $T_1$ Transgenic Plants: Seed is evenly dispersed into water-saturated soil in pots and placed into a dark 4° C. cooler for two nights to promote uniform germination. Pots are then removed from the cooler and covered with 55% shade cloth for 4-5 days. Cotyledons are fully expanded at this stage. FINALE® (Sanofi Aventis, Paris, France) is sprayed on plants (3 ml FINALE® diluted into 48 oz. water) and repeated every 3-4 days until only transformants remain.

GFP Assay

Tissues are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

| | |
|---|---|
| Flower | Pedicel, receptacle, nectary, sepal, petal, filament, anther, pollen, carpel, style, papillae, vascular, epidermis, stomata, trichome |

| | -continued |
|---|---|
| Silique | Stigma, style, carpel, septum, placentae, transmitting tissue, vascular, epidermis, stomata, abscission zone, ovule |
| Ovule | Pre-fertilization: inner integument, outer integument, embryo sac, funiculus, chalaza, micropyle, gametophyte<br>Post-fertilization: zygote, inner integument, outer integument, seed coat, primordia, chalaza, micropyle, early endosperm, mature endosperm, embryo |
| Embryo | Suspensor, preglobular, globular, heart, torpedo, late mature, provascular, hypophysis, radicle, cotyledons, hypocotyl |
| Stem | Epidermis, cortex, vascular, xylem, phloem, pith, stomata, trichome |
| Leaf | Petiole, mesophyll, vascular, epidermis, trichome, primordia, stomata, stipule, margin |

T1 Mature: These are the T1 plants resulting from independent transformation events. These are screened between stage 6.50-6.90 (i.e. the plant is flowering and 50-90% of the flowers that the plant will make have developed), which is 4-6 weeks of age. At this stage the mature plant possesses flowers, siliques at all stages of development, and fully expanded leaves. The plants are initially imaged under UV with a Leica Confocal microscope to allow examination of the plants on a global level. If expression is present, they are re-imaged using scanning laser confocal microscopy.

T2 Seedling: Progeny are collected from the T1 plants giving the same expression pattern and the progeny (T2) are sterilized and plated on agar-solidified medium containing M&S salts. In the event that there is no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings were screened until two seedlings were observed to have the same pattern. In general, the same expression pattern was found in the first two seedlings. However, up to 6 seedlings were screened before "no expression pattern"
was recorded. All constructs are screened as T2 seedlings even if they did not have an expression pattern in the T1 generation.

T2 Mature: The T2 mature plants were screened in a similar manner to the T1 plants. The T2 seeds were planted in the greenhouse, exposed to selection and at least one plant screened to confirm the T1 expression pattern. In instances where there were any subtle changes in expression, multiple plants were examined and the changes noted in the tables.

T3 Seedling: This was done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Results

The Promoter Expression Reports of the Tables present the results of the GFP assays as reported by their corresponding construct number and line number.

| Promoter Expression Report For PT0960 (SEQ ID NO:1) | | | | | |
|---|---|---|---|---|---|
| Promoter Tested In: *Arabidopsis thaliana*, Wassilewskija (WS) ecotype | | | | | |
| Spatial expression summary: | | | | | |
| Hypocotyl          H vascular | | | | | |
| Cotyledon          H vascular | | | | | |
| Rosette Leaf      H vascular | | | | | |
| Primary Root  L epidermis L cortex H endodermis H vascular | | | | | |
| Observed expression pattern: | | | | | |
| T1 Mature expression: None observed. | | | | | |
| T2 Seedling expression: High GFP expression throughout vasculature of seedlings. | | | | | |
| Source Promoter Organism: *Arabidopsis thaliana*, Columbia (Col) ecotype | | | | | |
| Vector:                           pNewbin4-HAP1-GFP | | | | | |
| Marker Type:          GFP-ER | | | | | |
| Generation Screened: XT1 Mature  XT2 Seedling | | | | | |
| Inductions completed. | | | | | |
| Treatment: | Age: | Gen: | Time points: | Events Screened / Response | Response: |
| 1. 14.3mM $KNO_3$ to 28.6 Mannitol | 4 wks | T2 | 72 hrs post transfer | 2/0 | No |

| Table 1-1. T1 Mature Plant Expression     Organs/Tissues screened | |
|---|---|
| Events Screened:    n= 3       Events Expressing:   n= 0 | |
| No GFP Expression Detected | |

| Table 2-1. T2 Seedling Expression      Tissues Screened | |
|---|---|
| Events Screened: n=3         Events Expressing: n=3 | |
| Expression Detected | |
| Hypocotyl | H vascular |
| Cotyledon | H vascular |
| Rosette Leaf | H vascular |
| Primary Root | L epidermis  L cortex  H endodermis  H vascular |

| Construct: | PT0960 |
|---|---|
| Promoter candidate I.D: | 22254785 |
| cDNA I.D: | 23518786 |
| Events expressing: | 01-03 |

| Promoter Expression Report YP2585 (SEQ ID NO:2) deletion of PT0743 | |
|---|---|
| Promoter Tested In: *Arabidopsis thaliana*, Wassilewskija (WS) ecotype | |
| Spatial expression summary: | |
| Primary Root | H epidermis H cortex H root hairs |

| Mature Root | H epidermis  H vascular  H pericycle  H stele |
|---|---|
| Observed expression pattern: | |
| T1 Mature expression: No expression detected | |
| T2 Seedling expression: Expression in root epidermis and cortex | |
| T2 Mature expression: No expression detected | |
| Source Promoter Organism: | *Arabidopsis thaliana*, Columbia (Col) ecotype |
| Vector: | pNewbin4-HAP1-GFP |
| Marker Type: | GFP-ER |
| Generation Screened: X T1 Mature  X T2 Seedling  X T2 Mature | |

| Table 1-2. T1 Mature Plant Expression | Organs/Tissues screened |
|---|---|
| No GFP Expression Detected | |

| Table 2-2. T2 Seedling Expression | Tissues Screened |
|---|---|
| Events Screened: n=6 | Events Expressing: n=5 (02-06) |
| Expression Detected | |
| Primary Root | H epidermis  H cortex  H root hairs |

| Table 3-2. T2 Mature Plant Expression | Organs/Tissues screened |
|---|---|
| Events Screened: n=6 | Events Expressing: n=3 (03, 04, 06 |
| Expression Detected | |
| Mature Root | H epidermis  H vascular  H pericycle  H stele |

| Table 4-2. | Promoter utility |
|---|---|
| Trait Area: | Water Use Efficiency, Nutrient Use Efficiency |
| Sub-trait Area: | Drought Tolerance |
| Utility: Among other uses this promoter sequence is useful to improve the uptake of water and nutrients from the soil. | |

| Construct: | YP2585 |
|---|---|
| Promoter candidate I.D: | 40983033 |
| cDNA I.D: | 23509083 |
| Events expressing: | 02-06 |

One or more fragments of the above described promoter are identified in the miscellaneous feature section of the relevant SEQ ID in the Sequence Listing. Those fragments were tested for promoter activity by the same procedures as described above, and the results are summarized below.
No expression is observed for Ceres Promoter YP2581.

| Promoter Expression Report For PT0998 (SEQ ID NO:3) | |
|---|---|
| Promoter Tested In: | *Arabidopsis thaliana*, Wassilewskija (WS) ecotype |
| Spatial expression summary: | |
| Flower | H anther  H tapetum  H silique |
| Silique | L vascular  L epidermis |
| Mature root | H mature root |
| Primary Root | H cortex  H endodermis  H vascular  L xylem  H phloem  H pericycle |
| Observed expression pattern: | |
| T1 Mature expression: High GFP expression in roots, tapetum cells of developing anthers and siliques. | |
| T2 Seedling expression: High GFP expression in cortex, endodermis, and surrounding vascular bundle. | |

| | |
|---|---|
| T2 Mature expression: | High GFP expression in roots (vasculature) of mature plants. |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature  X T2 Seedling  X T2 Mature |

| Table 1-3. T1 Mature Plant Expression | Organs/Tissues screened |
|---|---|
| Events Screened: n=4 | Events Expressing: n=4 |
| Expression Detected | |
| Flower | H anther H tapetum H silique |
| H Silique | L vascular L epidermis |
| Root | H Yes |

| Table 2-3. T2 Seedling Expression | Tissues Screened |
|---|---|
| Events Screened: n=4 | Events Expressing: n=4 |
| GFP Expression Detected | |
| X Primary Root | H cortex H endodermis  H vascular L xylem H phloem H pericycle |

| Table 3-3. T2 Mature Plant Expression | Organs/Tissues screened |
|---|---|
| Events Screened: n=4 | Events Expressing: n=4 |
| Expression Detected | |
| Mature Root | H mature root |

| Table 4-3. RT-PCR |
|---|
| Results: Plants were grown hydroponically for 4 weeks until tissue collection. Roots and aerial tissues (Aerials) were harvested separately in liquid nitrogen. For each event, two sets of samples are collected for qRT-PCR analysis. The data presented is the average ratio of roots and aerials between two replicates. |

| | PT0998-2 Ratio (Roots/Aerials) | PT0998-3 Ratio (Roots/Aerials) | PT0998-4 Ratio (Roots/Aerials) |
|---|---|---|---|
| HAP | 6.33 | 23.16 | 33.01 |
| GFP | 253.98 | 575.31 | 555.41 |

| Table 5-3. | Promoter utility |
|---|---|
| Trait Area: | Stress, Nutrients |
| Sub-trait Area: | nitrogen utilization, drought tolerance, UV-B tolerance |
| Utility: Among other uses this promoter sequence is useful to improve: Modulate nutrients, water uptake from soil and transportation within plants. Provide drought or UV protection. | |

| | |
|---|---|
| Construct: | PT0998 |
| Promoter candidate I.D: | 24469840 |
| cDNA I.D: | 23506262 + 23545255 |
| Events expressing: | 01, 02, 03, 04 |

One or more fragments of the above described promoter are identified in the miscellaneous feature section of the relevant SEQ ID in the Sequence Listing. Those fragments were tested for promoter activity by the same procedures as described above, and the results are summarized below.
No expression is observed for Ceres Promoter PD3457.

| Promoter Expression Report YP2219 (SEQ ID NO:4) |
|---|
| Promoter Tested In: *Arabidopsis thaliana*, Wassilewskija (WS) ecotype |
| Spatial expression summary: <br> Hypocotyl      L epidermis L cortex L vascular <br> Cotyledon      L hydathode L petiole L epidermis <br> Rosette Leaf      L epidermis H petiole <br> Primary Root      L epidermis H cortex H vascular <br> Lateral root      H lateral root cap |
| Observed expression pattern: <br> T1 Mature expression: No GFP expression observed <br> T2 Seedling expression: Hypocotyl, cotyledon, rosette leaf, primary, and lateral root <br> T2 Mature expression: |
| Source Promoter Organism: *Arabidopsis thaliana*, Columbia (Col) ecotype |
| Vector:      pNewbin4-HAP1-GFP |
| Marker Type:      GFP-ER |
| Generation Screened: X T1 Mature   X T2 Seedling |
| Inductions completed. |

| Treatment: | Age: | Gen: | Time points: | Events Screened / Response | Response: |
|---|---|---|---|---|---|
| 1. Drought | 4 wks | T2 | 1.0% moisture | 6/4 | Yes |

| Inducible expression summary: | | | |
|---|---|---|---|
| Treatment: | Time point induced: | Organs induced: | Tissues induced: |
| 1. Drought | 1.0% moisture | Stem, leaf, leaf | |

| Table 1-4. T1 Mature Plant Expression | Organs/Tissues screened |
|---|---|
| Events Screened:    n= 6 | Events Expressing:    n= 0 |
| No GFP Expression Detected | |

| Table 2-4. T2 Seedling Expression | Tissues Screened |
|---|---|
| Events Screened: n= 6 | Events Expressing: n= 4 |
| Expression Detected | |
| Hypocotyl | L epidermis L cortex L vascular |
| Cotyledon | L epidermisd L petiole L hydathode |
| Rosette Leaf | L epidermis H petiole |
| Primary Root | L epidermis H cortex H vascular |
| Lateral root | H lateral root cap |

| Table 4-4. | Promoter utility |
|---|---|
| Trait Area: | Water Use Efficiency |
| Sub-trait Area: | Drought Tolerance |
| Utility: Among other uses this promoter sequence is useful to engineer drought tolerance in plants. | |

| Construct: | YP2219 |
|---|---|
| Promoter candidate I.D: | 37172464 |
| cDNA I.D: | 23494283 |
| Events expressing: 01,02,04,06 | |

One or more fragments of the above described promoter are identified in the miscellaneous feature section of the relevant SEQ ID in the Sequence Listing. Those fragments were tested for promoter activity by the same procedures as described above, and the results are summarized below.

No induction is observed for Ceres Promoter YP2229.

| Promoter Expression Report For YP0286 (SEQ ID NO:5) |||||||
|---|---|---|---|---|---|---|
| Promoter Tested In: *Arabidopsis thaliana*, Wassilewskija (WS) ecotype ||||||||
| Spatial expression summary: |||||||
| Flower | L pedicel L epidermis ||||||
| Stem | L epidermis ||||||
| Hypocotyl | H epidermis ||||||
| Cotyledon | H mesophyll H vascular H epidermis H petiole ||||||
| Rosette Leaf | H epidermis H petiole ||||||
| Primary Root | H epidermis ||||||
| Lateral root | H lateral root cap ||||||
| Observed expression pattern: |||||||
| T1 mature: Low epidermal expression in stem and pedicles near inflorescence apical meristem. |||||||
| T2 seedling: High epidermal expression in cotyledons, petioles of emerging rosette leaves, hypocotyl, and root. Expression observed in vascular and mesophyll cells of cotyledons. |||||||
| Source Promoter Organism: *Arabidopsis thaliana*, WS ecotype |||||||
| Vector: | pNewbin4-HAP1-GFP ||||||
| Marker Type: | GFP-ER ||||||
| Generation Screened: XT1 Mature XT2 Seedling |||||||
| Inductions completed: |||||||
| Treatment: | Age: | Gen: | Time points: | Events Screened / Response: | Response: ||
| 1. Drought | 7 days | T2 | 3 Hrs Air dry | 2/0 | No ||
| 2. Drought | 4 weeks | T2 | 10-12 day No H20 | 2/2 | Yes ||
| Inducible expression summary: |||||||
| Treatment: | Time point induced: | | Organs induced: | | Tissues induced: ||
| 2. Drought | 10-12 day No H20 | | Flowers | | Pedicel, Epidermis ||
|  |  | | Siliques | | Epidermis ||
|  |  | | Leaf | | Epidermis, Vascular ||
|  |  | | Stem | | Epidermis ||

| Table 1-5. T1 Mature Plant Expression | Organs/Tissues screened |
|---|---|
| Events Screened: n=6 | Events Expressing: n=2 |
| GFP Expression Detected ||
| Flower | L pedicel L epidermis |
| Stem | L epidermis |

| Table 2-5. T2 Seedling Expression | Tissues Screened |
|---|---|
| Events Screened: n=2 | Events Expressing: n=2 |
| Seedlings expressing / Seedlings screened ||
| Event-04: 6/6 ||
| Event-06: 4/6 ||
| Expression Detected ||
| Hypocotyl | H epidermis |
| Cotyledon | H mesophyll H vascular H epidermis H petiole |
| Rosette Leaf | H epidermis H petiole |
| Primary Root | H epidermis |
| Lateral root | H lateral root cap |

| Table 3-5. | Promoter utility |
|---|---|
| Trait Area: | Water use efficiency |
| Sub-trait Area: | Drought |
| Utility: Among other uses this promoter sequence is useful to improve: Modulation growth and development. Modulation of nutrient uptake and loading. Expression of nitrate transports and water pumps. Modulation of drought responses, including modulation of water uptake and transport under drought conditions. ||
| Notes: Candidate to drive genes involved in osmotic stresses such as NCED. Endogenous promoter induced under drought. ||

| Construct: | YP0286 |
|---|---|
| Promoter candidate I.D: | 11768589 |
| cDNA I.D: | 12669548 (OCKHAM3-C) |
| Lines expressing: | YP0286 -04, -06; 7/3/03 |

| Promoter Expression Report YP1692 (SEQ ID NO:6) ||
|---|---|
| Promoter Tested In: *Arabidopsis thaliana*, Wassilewskija (WS) ecotype ||
| Spatial expression summary: ||
| Flower | L petal L vascular |
| Hypocotyl | L epidermis L vascular |
| Cotyledon | L vascular |
| Primary Root | H vascular |
| Lateral root | H vascular |
| Root | H mature root |
| Observed expression pattern: T1 mature expression: GFP expressed in vasculature of petals in flowers. T2 seedling expression: High GFP expression in vasculature of root. Low GFP expression in hypocotyl and cotyledons. GFP expressed in epidermis of hypocotyl near root transition zone. T1 mature expression: GFP expressed in vasculature of root. ||
| Source Promoter Organism: | *Arabidopsis thaliana*, Columbia (Col) ecotype |
| Vector: | pNewbin4-HAP1-GFP |
| Marker Type: | GFP-ER |
| Generation Screened: X T1 Mature  X T2 Seedling  X T2 Mature ||
| Inductions completed. ||

| Treatment: | Age: | Gen: | Time points: | Events Screened / Response | Response: |
|---|---|---|---|---|---|
| 1. Drought | 4 wks | T2 | 1.0% moisture | 6/2 | Yes |

| Inducible expression summary: ||||
|---|---|---|---|
| Treatment: | Time point induced: | Organs induced: | Tissues induced: |

| Table 1-6. T1 Mature Plant Expression | Organs/Tissues screened ||
|---|---|---|
| Events Screened: n=6 | Events Expressing: n=3 ||
| Expression Detected |||
| Flower | L petal L vascular ||

| Table 2-6. T2 Seedling Expression | Tissues Screened |
|---|---|
| Events Screened: n=6 | Events Expressing: n=1 |
| Expression Detected ||

| Hypocotyl | L epidermis  L vascular |
|---|---|
| Cotyledon | L vascular |
| Primary Root | H vascular |
| Lateral root | H vascular |

| Table 3-6. T2 Mature Plant Expression | Organs/Tissues screened | |
|---|---|---|
| Events Screened: n=5 | Events Expressing: n=2 | |
| Expression Detected | | |
| X Root | H mature root | |

| Construct: | YP1692 |
|---|---|
| Promoter candidate I.D: | 15371608 |
| cDNA I.D: | 36534367 |
| Events expressing: | 01-06 |

| Promoter Expression Report YP1894   (SEQ ID NO:7) | | | | | |
|---|---|---|---|---|---|
| Promoter Tested In: *Arabidopsis thaliana*, Wassilewskija (WS) ecotype | | | | | |
| Spatial expression summary: | | | | | |
| Cotyledon | L epidermis | | | | |
| Primary Root | H epidermis  H cortex | | | | |
| Root | H mature root | | | | |
| Observed expression pattern: Root Specific. | | | | | |
| T1 Mature expression: No expression detected. | | | | | |
| T2 Seedling expression: High GFP expression in epidermis and cortex cells of root. Low GFP expression in cotyledons. | | | | | |
| T2 Mature expression: High GFP expression in roots. | | | | | |
| Inductions: Expression enhanced by high-nitrogen conditions (see Induction table below). | | | | | |
| Source Promoter Organism: *Arabidopsis thaliana*, Columbia (Col) ecotype | | | | | |
| Vector: | pNewbin4-HAP1-GFP | | | | |
| Marker Type: | GFP-ER | | | | |
| Generation Screened: X T1 Mature  X T2 Seedling  X T2 Mature | | | | | |
| Inductions Table. Upregulation of gene expression was expected in low-nitrogen conditions. This was not observed. However, enhanced GFP was detected in response to the high-nitrogen condition (control test) (see Table 4 below). | | | | | |
| Treatment: | Age: | Gen: | Time points: | Events Screened / Response | Response: |
| 1. Nitrogen (High to Low) - 14.3mM KNO$_3$ to 28.6mM Mannitol | 4wks | T2 | 90 hrs | 6/0 | No |
| Inducible expression summary: | | | | | |
| Treatment:        Time point induced: | | Organs induced: | Tissues induced: | | |
| High nitrogen         90 hrs | | Leaves and stems | | | |

| Table 1-7. T1 Mature Plant Expression | Organs/Tissues screened |
|---|---|
| Events Screened: n=6 | Events Expressing: n=0 |
| No GFP Expression Detected | |

| Table 2-7. T2 Seedling Expression | Tissues Screened |
|---|---|

| | |
|---|---|
| Events Screened: n=6 | Events Expressing: n=6(01-06) |
| Expression Detected | |
| Cotyledon | L epidermis |
| Primary Root | H epidermis  H cortex |

| Table 3-7. T2 Mature Plant Expression | Organs/Tissues screened |
|---|---|
| Events Screened:     n=6 | Events Expressing:     n=6 (01-06) |
| Expression Detected | |
| Root | H mature root |

| Table 5-7. | Promoter utility |
|---|---|
| Trait Area: | Water Use Efficiency, Nutrient |
| Sub-trait Area: | Drought, Nitrogen use efficiency, |
| Utility: Among other uses this promoter sequence is useful to improve:   Expression in the roots is useful for improving water and nutrient uptake into the root mass without undesirable affects on the above ground tissues. The high-nitrogen induction is useful in reducing the toxicity associated with very high levels of nitrogen and/or bypassing the feedback loop that limits nitrogen uptake when nitrogen levels are not limiting, thus accelerating nitrogen uptake for either storage for later use or for enhancing growth. | |

| | |
|---|---|
| Construct: | YP1894 |
| Promoter candidate I.D: | 25518825 |
| cDNA I.D: | 23499704 |

| Promoter Expression Report For YP1976 (SEQ ID NO:8) | |
|---|---|
| Promoter Tested In: *Arabidopsis thaliana*, Wassilewskija (WS) ecotype | |
| Spatial expression summary: | |
| Hypocotyl | L epidermis |
| Primary Root | H cortex |
| Lateral root | H cortex |
| Root | H mature root |
| Observed expression pattern: <br> T1 mature expression: No GFP expression observed in aerial organs. <br> T2 seedling expression: High GFP expressed in epidermal cells at root transition zone. GFP is expressed in cortex cells of lower main root and lateral root. <br> T2 mature expression: High GFP expression in roots of mature plant. No GFP expression observed in aerial tissues. | |
| Source Promoter Organism: *Arabidopsis thaliana*, Columbia (Col) ecotype | |
| Vector: | pNewbin4-HAP1-GFP |
| Marker Type: | GFP-ER |
| Generation Screened: X T1 Mature  X T2 Seedling  X T2 Mature | |

| Table 1-8. T1 Mature Plant Expression | Organs/Tissues screened |
|---|---|
| Events Screened:     n= 6 | Events Expressing:     n= 0 |
| No GFP Expression Detected | |

| Table 2-8. T2 Seedling Expression | Tissues Screened |
|---|---|
| Events Screened: n=  6 | Events Expressing: n= 6 |
| Expression Detected | |
| X Hypocotyl | L epidermis |

| X Primary Root | H cortex |
|---|---|
| X Lateral root | H cortex |

| Table 3-8. T2 Mature Plant Expression | Organs/Tissues screened | |
|---|---|---|
| Events Screened: n=6 | | Events Expressing: n=6 |
| Expression Detected | | |
| X Root | H mature root | |

| Table 4-8 | Promoter utility |
|---|---|
| Trait Area: | Nutrient and water economy. |
| Sub-trait Area: | Nitrogen use efficiency Water use efficiency. |
| Utility: Among other uses this promoter sequence is useful to improve: Nitrogen use efficiency in lower/non-limiting nitrogen environments, enhanced water uptake in drought and non-limiting water environments, and protection against soil-borne nematodes, root worms, fungal and bacterial pathogens. ||

| Construct: | YP1976 |
|---|---|
| Promoter candidate I.D: | 15371806 |
| cDNA I.D: | 23523729 |
| Events expressing: | 01-06 |

| Promoter Expression Report YP2016 (SEQ ID NO:9) ||
|---|---|
| Promoter Tested In: *Arabidopsis thaliana*, Wassilewskija (WS) ecotype ||
| Spatial expression summary: ||
| Flower | H pedicel H receptacle H nectary H sepal H petal H filament H tapetum H carpel H style H papillae H vascular H epidermis H stomata H silique |
| Silique | H stigma H style H carpel H septum H vascular H epidermis H abscission zone H ovule |
| Ovule | Post-fertilization: H inner integument H outer integument H seed coat H embryo |
| Embryo | H torpedo H late H mature |
| Stem | H vascular H xylem H phloem H pith H epidermis H cortex |
| Leaf | H petiole H mesophyll H epidermis H stomata |
| Hypocotyl | H epidermis H cortex H vascular H xylem H phloem |
| Cotyledon | H mesophyll H vascular H epidermis H petiole |
| Rosette Leaf | H mesophyll H vascular H epidermis |
| Primary Root | H cortex H vascular |
| Lateral root | H root cap |
| Observed expression pattern: ||
| T1 Mature expression: GFP broadly expressed throughout mature plant with highest expression at inflorescence meristems. High GFP expression throughout organs of flowers. Not expressed in anther walls of mature stamen. High GFP expression in silique, developing ovules, seed and embryos. GFP expression in epidermis, vasculature and mesophyll in leaves. GFP expressed in epidermis, cortex, pith, and vascular bundles throughout stem, highest near apex decreasing toward rosette leaves. GFP expression in mature root. ||
| T2 Seedling expression: GFP expression throughout epidermis, cortex, vascular and mesophyll cells in aerial tissues of seedling. In root, GFP expressed in cortex and vasculature. ||
| T2 Mature expression: GFP broadly expressed throughout mature plant with highest expression at inflorescence meristems and root. ||
| Source Promoter Organism: *Arabidopsis thaliana*, Columbia (Col) ecotype ||

| | |
|---|---|
| Vector: | pNewbin4-HAP1-GFP |
| Marker Type: | GFP-ER |
| Generation Screened: | X T1 Mature  X T2 Seedling  X T2 Mature |

| Table 1-9. T1 Mature Plant Expression | Organs/Tissues screened |
|---|---|
| Events Screened: n= 6 | Events Expressing: n= 6 |
| Expression Detected | |
| Flower | H pedicel H receptacle H nectary H sepal H petal H filament H tapetum H carpel H style H papillae H vascular H epidermis H stomata H silique |
| Silique | H stigma H style H carpel H septum H vascular H epidermis H abscission zone H ovule |
| Ovule | Post-fertilization: H inner integument H outer integument H seed coat H embryo |
| Embryo | H torpedo H late H mature |
| Stem | H epidermis H cortex H vascular H xylem H phloem H pith |
| Leaf | H petiole H mesophyll H epidermis H stomata |

| Table 2-9. T2 Seedling Expression | Tissues Screened |
|---|---|
| Events Screened: n= 4 | Events Expressing: n= 4 |
| Expression Detected | |
| Hypocotyl | H epidermis H cortex H vascular H xylem H phloem |
| Cotyledon | H mesophyll H vascular H epidermis H petiole |
| Rosette Leaf | H mesophyll H vascular H epidermis |
| Primary Root | H cortex H vascular |
| Lateral root | H root cap |

| Table 3-9. T2 Mature Plant Expression | Organs/Tissues screened |
|---|---|
| Events Screened: n= 4 | Events Expressing: n= 4 |

| Table 4-9. | Promoter utility |
|---|---|
| Trait Area: | Plant growth and development |
| Sub-trait Area: | Size and source capacity |
| Utility: Among other uses this promoter sequence is useful to improve: Plant size and architecture, growth rate, seedling establishment, responses to shade and low light, responses to drought and cold, source capacity and sucrose loading, seed filling, seed size and plant yield. | |
| Construct: | YP2016 |
| Promoter candidate I.D: | 25087074 |
| cDNA I.D: | 23495629 |
| Events expressing: | 01-04 |

| Promoter Expression Report YP2097 (SEQ ID NO:10) | |
|---|---|
| Promoter Tested In: *Arabidopsis thaliana*, Wassilewskija (WS) ecotype | |
| Spatial expression summary: | |
| Flower | H pollen |
| Primary Root | L epidermis |
| Root | L mature root |
| Observed expression pattern: | |
| T1 mature expression: High GFP expression specific to pollen. | |

| | |
|---|---|
| T2 seedling expression: GFP expression in epidermal cells at root transition zone decreasing toward root tip. T2 mature expression: High GFP expression in pollen. GFP expression in epidermis and vascular cells of root. | |
| Source Promoter Organism: | *Arabidopsis thaliana*, Columbia (Col) ecotype |
| Vector: | pNewbin4-HAP1-GFP |
| Marker Type: | GFP-ER |
| Generation Screened: X T1 Mature  X T2 Seedling  X T2 Mature | |
| Inductions completed. | |

| Treatment: | Age: | Gen: | Time points: | Events Screened / Response | Response: |
|---|---|---|---|---|---|
| 1. Drought | 4 wks | T2 | 1.0% moisture | 6/2 | Yes |

| Inducible expression summary: Treatment:    Time point induced:    Organs induced:    Tissues induced: |
|---|
| 1. Drought    1.0% moisture    Flower    Pollen, Epidermis<br>    Leaf    Guard cells, Epidermis<br>    Stem    Guard cells<br>    Root    Vascular |

| Table 1-10. T1 Mature Plant Expression | Organs/Tissues screened |
|---|---|
| Events Screened:   n=6 | Events Expressing:   n=4 |
| Expression Detected | |
| Flower | H pollen |

| Table 2-10. T2 Seedling Expression | Tissues Screened |
|---|---|
| Events Screened: n=6 | Events Expressing: n=2 |
| Expression Detected | |
| Primary Root | L epidermis |

| Table 3-10. T2 Mature Plant Expression | Organs/Tissues screened |
|---|---|
| Events Screened:   n=6 | Events Expressing:   n=3 |
| Expression Detected | |
| Root | L mature root |

| Table 5-10. | Promoter utility |
|---|---|
| Trait Area: | PG&D, water use efficiency |
| Sub-trait Area: | Drought tolerance, |
| Utility: Among other uses this promoter sequence is useful to improve: Desiccation tolerance, recovery from drought, drought tolerance, improve water use efficiency, seed size and nutrient use efficiency and nitrogen use efficiency. | |

| Construct: | YP2097 |
|---|---|
| Promoter candidate I.D: | 29223804 |
| cDNA I.D: | 36541759 |
| Events expressing: | 02, 04 |

| Promoter Expression Report YP2538 (SEQ ID NO:11) |
|---|
| Promoter Tested In: *Arabidopsis thaliana*, Wassilewskija (WS) ecotype |

| | |
|---|---|
| Spatial expression summary: | |
| Flower | H pedicel H anther H silique |
| Silique | H carpel H epidermis |
| Ovule | Post-fertilization: H embryo |
| Embryo | H mature |
| Hypocotyl | H epidermis H vascular |
| Cotyledon | H mesophyll H vascular H epidermis |
| Rosette Leaf | H mesophyll H epidermis |
| Primary Root | H vascular H root cap |
| Aerial organs | H inflorescence H flowers H silique H stem |
| Root | H mature root |

Observed expression pattern:
T1 Mature expression: High GFP expression at inflorescence. GFP expressed in stem and pedicels near apex. High GFP expression in anthers of developing flowers and in carpels and mature embryos in mature siliques.
T2 Seedling expression: High GFP expression in vasculature of root, hypocotyl and cotyledons. High GFP expression in epidermis, mesophyll and vasculature of cotyledons. High GFP expression in emerging rosette leaves.
T2 Mature expression: High GFP expression at inflorescence, flowers, stem and root.

Source Promoter Organism: *Arabidopsis thaliana*, Columbia (Col) ecotype
Vector: pNewbin4-HAP1-GFP
Marker Type: GFP-ER
Generation Screened: X T1 Mature  X T2 Seedling  X T2 Mature
Inductions completed.

| Treatment: | Age: | Gen: | Time points: | Events Screened / Response | Response: |
|---|---|---|---|---|---|
| 1. Drought | 4 wks | T2 | 1.0% moisture | 4/3 | Yes |

Inducible expression summary:

| Treatment: | Time point induced: | Organs induced: | Tissues induced: |
|---|---|---|---|
| 1. Drought | 1.0% moisture | Inflorescence | Pedicels, Silique, Stem |
| | | Flower | Silique, Stamens |
| | | Silique | Epidermis, Vascular |
| | | Stem | Vascular |
| | | Root | Epidermis |

| Table 1-11. T1 Mature Plant Expression | Organs/Tissues screened |
|---|---|
| Events Screened: n=5 | Events Expressing: n=2 (02, 05) |
| Expression Detected | |
| Flower | H pedicel H anther H silique |
| Silique | H carpel  H epidermis |
| Ovule | Post-fertilization: H embryo |
| Embryo | H mature |

| Table 2-11. T2 Seedling Expression | Tissues Screened |
|---|---|
| Events Screened: n=3 | Events Expressing: n=2 (03, 05) |
| Expression Detected | |
| Hypocotyl | H epidermis  H vascular |
| Cotyledon | H mesophyll H vascular H epidermis |
| Rosette Leaf | H mesophyll  H epidermis |
| Primary Root | H vascular  H root cap |

| Table 3-11. T2 Mature Plant Expression | Organs/Tissues screened |
|---|---|
| Events Screened: n=4 | Events Expressing: n=2 (03, 05) |
| Expression Detected | |
| Aerial organs | H inflorescence  H flowers  H silique  H stem |
| Root | H mature root |

| Table 5-11. | Promoter utility |
|---|---|
| Trait Area: Water Use Efficiency, Nutrient Use Efficiency, Yield ||
| Sub-trait Area: Drought Tolerance, Low Nitrogen Tolerance, Low Phosphorous Tolerance, Seed Size and Yield ||
| Utility: Among other uses this promoter sequence is useful to improve: response to drought conditions and low soil nutrient levels. Expression in the embryo could be valuable for engineering of seed size and yield. ||

| Construct: | YP2538 |
|---|---|
| Promoter candidate I.D: | 25087125 |
| cDNA I.D: | 23519856 |
| Events expressing: | 03-05 |

| Promoter Expression Report YP2552 (SEQ ID NO:12) ||||||
|---|---|---|---|---|---|
| Promoter Tested In: *Arabidopsis thaliana*, Wassilewskija (WS) ecotype ||||||
| Spatial expression summary: ||||||
| Primary Root  H epidermis  H vascular  H root hairs ||||||
| Mature Root  H epidermis  H vasculature  H xylem  H phloem  H root hairs  lateral root  L stele ||||||
| Observed expression pattern: ||||||
| T1 Mature expression: No GFP expression detected. ||||||
| T2 Seedling expression: Root specific GFP expression. High GFP expression in epidermal and vascular cells. ||||||
| T2 Mature expression: Root specific GFP expression. High GFP expression in epidermal and vascular cells. ||||||
| Source Promoter Organism: *Arabidopsis thaliana*, Columbia (Col) ecotype ||||||
| Vector: pNewbin4-HAP1-GFP ||||||
| Marker Type: GFP-ER ||||||
| Generation Screened: X T1 Mature  X T2 Seedling  X T2 Mature ||||||
| Inductions completed: ||||||
| Treatment: | Age: | Gen: | Time points: | Events Screened / Response | Response: |
| 1. Cold | 10 day | T2 | 4 hr | 6/0 | None |
| 2. Nitrogen - high N to low N [14.3 mM KNO$_3$ to 28.6 mM Mannitol] | 4 weeks | T2 | 4 hr | 6/0 | None |
| 3. Far Red Far Red$_{730}$= 525 µW/ cm | 10 day | T2 | 4 hr | 6/0 | None |
| Inducible expression summary: ||||||
| Treatment:     Time point induced:     Organs induced:     Tissues induced: ||||||

| Table 1-12. T1 Mature Plant Expression | Organs/Tissues screened |
|---|---|
| Events Screened: n=6 | Events Expressing: n=0 |

| No GFP Expression Detected |
| --- |

| Table 2-12. T2 Seedling Expression | Tissues Screened |
| --- | --- |
| Events Screened: n=6 | Events Expressing: n=4 (01-03, 06) |
| Expression Detected | |
| X Primary Root | H epidermis  H vasculature  H root hairs |

| Table 3-12. T2 Mature Plant Expression | Organs/Tissues screened |
| --- | --- |
| Events Screened:  n=6 | Events Expressing:  n=5 (01, 02, 03, 05, 06) |
| Expression Detected | |
| Mature Root | H epidermis  H vasculature  H xylem  H phloem  H root hairs  lateral root  L stele |

| Table 4-12. | Promoter utility |
| --- | --- |
| Trait Area: | Water Use Efficiency, Nutrient Use Efficiency |
| Sub-trait Area: | Drought Tolerance, Nitrogen and Phosphorous Use Efficiency |
| Utility: Among other uses this promoter sequence is useful to improve the uptake of water and nutrients. | |

| Construct: | YP2552 |
| --- | --- |
| Promoter candidate I.D: | 25659462 |
| cDNA I.D: | 23504306 |
| Events expressing: | 01, 02, 03, 05, 06 |

| Promoter Expression Report YP2563 (SEQ ID NO:13) |||||||
|---|---|---|---|---|---|---|
| Promoter Tested In: *Arabidopsis thaliana*, Wassilewskija (WS) ecotype ||||||||
| Spatial expression summary: |||||||
| Flower | H carpel H silique ||||||
| Silique | H carpel ||||||
| Ovule | Post-fertilization: H funiculus H seed coat ||||||
| Hypocotyl | H epidermis L vascular ||||||
| Cotyledon | L epidermis H mesophyll H epidermis ||||||
| Primary Root | L epidermis L cortex H vascular H root cap H root hairs ||||||
| Lateral root | L epidermis ||||||
| Observed expression pattern: <br>T1 Mature expression: High GFP expression in carpels and in seed coats and funiculus of mature siliques. <br>T2 Seedling expression: High GFP expression in vasculature throughout root and in epidermis and cortex cells near root tip at elongation zone. GFP expressed in root hair and root cap. <br>T2 Mature expression: High GFP expression in roots and lateral inflorescences. |||||||
| Source Promoter Organism: *Arabidopsis thaliana*, Columbia (Col) ecotype |||||||
| Vector: | pNewbin4-HAP1-GFP ||||||
| Marker Type: | GFP-ER ||||||
| Generation Screened: X T1 Mature  X T2 Seedling  X T2 Mature |||||||
| Inductions completed. |||||||
| Treatment: | Age: | Gen: | Time points: | Events Screened / Response | Response: ||
| 1. Nitrogen - high N to low N [14.3 mM KNO₃ to 28.6 mM Mannitol] | 4wks | T2 | 72 Hr | 12/0 | None ||
| Inducible expression summary: <br>Treatment:       Time point induced:       Organs induced:       Tissues induced: |||||||

| Table 1-13. T1 Mature Plant Expression | Organs/Tissues screened |
|---|---|
| Events Screened:      n=12 | Events Expressing:   n=12 (01-12) |
| Expression Detected ||
| Flower | H carpel H silique |
| Silique | H carpel |
| Ovule | Post-fertilization: H funiculus H seed coat |

| Table 2-13. T2 Seedling Expression | Tissues Screened |
|---|---|
| Events Screened: n=11 | Events Expressing: n=9 (02-04, 06, 09-11, 13, 14) |
| Expression Detected ||
| Hypocotyl | H epidermis  L vascular |
| Cotyledon | L epidermis |
| Rosette Leaf | H mesophyll  H epidermis |
| Primary Root | L epidermis  L cortex  H vascular  H root cap  H root hairs |
| Lateral root | L epidermis |

| Table 3-13. T2 Mature Plant Expression | Organs/Tissues screened |
|---|---|
| Events Screened:     n=5 | Events Expressing:    n=4 (11-15) |
| Expression Detected ||
| Aerial organs | H inflorescence  L stem |

| Root | H mature root |

| Table 4-13. | Promoter utility |
|---|---|
| Trait Area: Nutrient Use Efficiency, Water Use Efficiency, Yield, PG&D, Confinement ||
| Sub-trait Area: Nitrogen and Phosphorous Utilization, Drought Tolerance, Seed Size, Plant Establishment, Seed Confinement ||
| Utility: Among other uses this promoter sequence could be useful to improve enhance the uptake of nutrients and water from the soil (root), and seed size (seed coat). Expression in the seed could also be used to engineer seed ablation and seed confinement. ||

| Construct: | YP2563 |
|---|---|
| Promoter candidate I.D: | 25518834 |
| cDNA I.D: | 36516796 |
| Events expressing: | 01-12 |

| Promoter Expression Report YP2571 (SEQ ID NO:14) ||
|---|---|
| Promoter Tested In: *Arabidopsis thaliana*, Wassilewskija (WS) ecotype ||
| Spatial expression summary: ||
| Flower | H sepal H petal H anther H vascular H stomata H silique |
| Silique | H style H carpel H funiculus H vascular |
| Leaf | L vascular |
| Aerial organs | H inflorescence |
| Root | H mature root |
| Hypocotyl | H vascular |
| Cotyledon | H mesophyll H vascular H epidermis |
| Primary Root | H vascular |
| Observed expression pattern: ||
| T1 Mature expression: High GFP expression detected in inflorescences. T2 Seedling expression: High GFP expression in vasculature of hypocotyls, cotyledons and root. GFP expression in epidermis and mesophyll cells of cotyledons. T2 Mature expression: High GFP expression in vasculature and guard cells of sepals and in anthers, petals and silique of flowers. GFP expressed in style, carpels and vasculature of silique. Not expressed in ovules or seed. Low GFP expression in leaf vasculature. High GFP expression in root. ||
| Source Promoter Organism: *Arabidopsis thaliana*, Columbia (Col) ecotype ||
| Vector: | pNewbin4-HAP1-GFP |
| Marker Type: | GFP-ER |
| Generation Screened: X T1 Mature  X T2 Seedling  X T2 Mature ||
| Inductions completed. ||

| Treatment: | Age: | Gen: | Time points: | Events Screened / Response | Response: |
|---|---|---|---|---|---|
| 1. ABA – [uM] | 14 days | T2 | 4 hrs | 6/0 | No |
| 2. Heat – 28C | 15 days | T2 | 24 hrs | 3/3 | Low |
| 3. Heat – 36C | 9 days | T2 | >24hrs | 6/3 | High |
| 4. Heat – 41C | 14 days | T2 | 4 hrs | 3/3 | Medium |
| 5. Heat – 41C | 15 days | T2 | 24 hrs | 3/0 | No |

| 6. Heat – 46C | 14 days | T2 | 4 hrs | 3/0 | No |
|---|---|---|---|---|---|
| 7. Heat – 40C | 4 wks | T2 | 24 hrs | 6/6 | Low |
| 8. Drought | 4 wks | T2 | 1.0% moisture | 6/6 | High |

Inducible expression summary:

| Treatment: | Time point induced: | Organs induced: | Tissues induced: |
|---|---|---|---|
| 2. Heat – 28C | 24 hrs | Cotyledons<br>Rosette leaf | |
| 3. Heat – 36C | >24hrs | Cotyledons<br>Rosette leaf<br>Root | Ep, Me, Vs<br>Ep, Me, Vs<br>Vs |
| 4. Heat – 41C | 4 hrs | Cotyledons<br>Rosette leaf | |
| 7. Heat – 40C | 24 hrs | Flower<br>Stem<br>Leaf | Se, Pe, Vs<br>Ph, Vs<br>Vs |
| 8. Drought | 1.0% moisture | Flower<br>Stem<br>Leaf<br>Root | Se, Pe, Ca<br>Xy, Ph, Vs<br>Ep, Me<br>Ep |

| Table 1-14. T1 Mature Plant Expression | Organs/Tissues screened |
|---|---|
| Events Screened: n=6 | Events Expressing: n=1 (04) |
| Expression Detected | |
| Inflorescence | H flowers |

| Table 2-14. T2 Seedling Expression | Tissues Screened |
|---|---|
| Events Screened: n=6 | Events Expressing: n=2 (04, 05) |
| Expression Detected | |
| Hypocotyl | H vascular |
| Cotyledon | H mesophyll  H vascular  H epidermis |
| Primary Root | H vascular |

| Table 3-14. T2 Mature Plant Expression | Organs/Tissues screened |
|---|---|
| Events Screened: n=6 | Events Expressing: n=6 (01-06) |
| Expression Detected | |
| Flower | H sepal  H petal  H anther  H vascular  H stomata  H silique |
| Silique | H style  H carpel  H funiculus  H vascular |
| Leaf | L vascular |
| Aerial organs | H inflorescence |
| Root | H mature root |

| Table 5-14. | Promoter utility |
|---|---|
| Trait Area: Water Use Efficiency | |
| Sub-trait Area: Drought Tolerance, Heat Stress Tolerance | |
| Utility: Among other uses this promoter sequence is useful to improve plant tolerance to heat and drought stress. | |

| Construct: | YP2571 |
|---|---|
| Promoter candidate I.D: | 29223786 |
| cDNA I.D: | 23618816 |
| Events expressing: | 01-06 |

| Promoter Expression Report YP2590 (SEQ ID NO:15) | |
|---|---|
| Promoter Tested In: *Arabidopsis thaliana*, Wassilewskija (WS) ecotype | |
| Spatial expression summary: <br> Arabidopsis | |
| Flower | H pedicel |
| Silique | H ovule |
| Ovule | Pre-fertilization: H funiculus <br> Post-fertilization: H funiculus |
| Aerial organs | H flowers |
| Root | H mature root |
| Rice | |
| Root | H not-specific |
| Meristem | H not-specific |
| Observed expression pattern: <br> Arabidopsis: <br> T1 Mature expression: High GFP expression at the distal end of the funiculus in developing ovules and seed. GFP highly localized to adaxial side at the base of the pedicel, in structures resembling stipules of leaves. <br> T2 Seedling expression: No GFP expression detected. <br> T2 Mature expression: GFP detected at the base of pedicles and roots. <br> Rice: <br> T0 Seedling expression: GFP expression was detected strongly throughout the root and in meristematic tissues corresponding to the stem nodes. | |
| Source Promoter Organism: *Arabidopsis thaliana*, Columbia (Col) ecotype | |
| Vector: | pNewbin4-HAP1-GFP |
| Marker Type: | GFP-ER |
| Generation Screened: X T1 Mature  X T2 Seedling  X T2 Mature | |

| Table 1-14. T1 Mature Plant Expression | Organs/Tissues screened |
|---|---|
| Events Screened: n=6 | Events Expressing: n=3 |
| Expression Detected | |
| Flower | H pedicel |
| Silique | H ovule |
| Ovule | Pre-fertilization: H funiculus <br> Post-fertilization: H funiculus |

| Table 2-14. T2 Seedling Expression | Tissues Screened |
|---|---|
| Events Screened: n=6 | Events Expressing: n=0 |
| No GFP Expression Detected | |

| Table 3-14. T2 Mature Plant Expression | Organs/Tissues screened |
|---|---|
| Events Screened: n=6 | Events Expressing: n=2 (01, 03, 04, 06) |
| Expression Detected | |
| Aerial organs | H flowers |

| | |
|---|---|
| Root | H mature root |

| Table 4-14. T0 Rice Seedlings Organs/Tissues screened | | | |
|---|---|---|---|
| Events Screened: | n=13 | Events Expressing: | n=4 (01, 02, 06, 09) |
| Expression Detected | | | |
| Root | H not-specific | | |
| Meristem | L not-specific | | |

| Table 5-14. | Promoter utility |
|---|---|
| Trait Area: | Yield, PG&D, Confinement, Water Use Efficiency |
| Sub-trait Area: | Seed Number, Seed Growth, Plant Size, Growth Rate |
| Utility: Among other uses this promoter sequence is useful to improve plant architecture and increase the number of secondary floral branches. Expression in the root could be valuable for improved uptake and transport of water and nutrients. | |

| | |
|---|---|
| Arabidopsis Construct: | YP2590 –Arabidopsis |
| Promoter candidate I.D: | 25659363 |
| cDNA I.D: | 23523207 |
| Events expressing: | 02, 03, 04 |
| Rice Construct: | PD3146 |
| Promoter candidate I.D: | 55210297 |
| cDNA I.D: | 23523207 |
| Events expressing: | 01, 02, 06, 09 |

| Promoter Expression Report YP2606 (SEQ ID NO:16) | |
|---|---|
| Promoter Tested In: *Arabidopsis thaliana*, Wassilewskija (WS) ecotype | |
| Spatial expression summary: Primary Root H epidermis H cortex Mature Root H epidermis L cortex H stele H vasculature | |
| Observed expression pattern: T1 Mature expression: No GFP expression detected. T2 Seedling expression: Root specific GFP expression. GFP expressed in root epidermis and cortex cells. T2 Mature expression: Root specific GFP expression. GFP expressed in root epidermis and the stele, non-ground cell vascular region of root. | |
| Source Promoter Organism: *Arabidopsis thaliana*, Columbia (Col) ecotype | |
| Vector: | pNewbin4-HAP1-GFP |
| Marker Type: | GFP-ER |
| Generation Screened: X T1 Mature  X T2 Seedling  X T2 Mature | |

| Table 1-15. T1 Mature Plant Expression | Organs/Tissues screened | |
|---|---|---|
| Events Screened: n=6 | Events Expressing: | n=0 |
| No Expression Detected | | |

| Table 2-15. T2 Seedling Expression | Tissues Screened |
|---|---|
| Events Screened: n=6 | Events Expressing: n=3 (04-06) |
| Expression Detected | |
| Primary Root | H epidermis H cortex |

| Table 3-15. T2 Mature Plant Expression | Organs/Tissues screened |
|---|---|
| Events Screened: n=6 | Events Expressing: n=2 (04, 06) |
| Expression Detected | |
| Mature Root | H epidermis H cortex H stele H vasculature |

| Table 4-15. | Promoter utility |
|---|---|
| Trait Area: | Water Use Efficiency, Nutrient Use Efficiency |
| Sub-trait Area: | Drought Tolerance, Nitrogen and Phosphorous Utilization |
| Utility: Among other uses this promoter sequence is useful to improve the uptake of water and nutrients. | |

| Construct: | YP2606 |
|---|---|
| Promoter candidate I.D: | 25086987 |
| cDNA I.D: | 36511228 |
| Events expressing: | 04-06 |

One or more fragments of the above described promoter are identified in the miscellaneous feature section of the relevant SEQ ID in the Sequence Listing. Those fragments were tested for promoter activity by the same procedures as described above, and the results are summarized below.
Ceres Promoter PD3464 expresses weakly in roots in rice.

| Promoter Expression Report YP2608 (SEQ ID NO:17) | |
|---|---|
| Promoter Tested In: *Arabidopsis thaliana*, Wassilewskija (WS) ecotype | |
| Spatial expression summary: | |
| Primary Root | H epidermis H cortex |
| Aerial organs | H flowers |
| Flower | H stamen H filament H anther |
| Mature Root | H epidermis L cortex H stele |
| Observed expression pattern: T1 Mature expression: No GFP expression detected. T2 Seedling expression: GFP expressed in root epidermis. T2 Mature expression: High stamen specific GFP expression corresponding to third organ whorl in Arabidopsis flower. GFP expressed in sub-epidermal cells in root. | |
| Source Promoter Organism: *Arabidopsis thaliana*, Columbia (Col) ecotype | |
| Vector: | pNewbin4-HAP1-GFP |
| Marker Type: | GFP-ER |
| Generation Screened: X T1 Mature  X T2 Seedling  X T2 Mature  T3 Seedling | |

| Table 1-16. T1 Mature Plant Expression | Organs/Tissues screened |
|---|---|
| Events Screened: n=4 | Events Expressing: n=0 |
| No GFP Expression Detected | |

| Table 2-16. T2 Seedling Expression | Tissues Screened |
|---|---|
| Events Screened: n=5 | Events Expressing: n=5 (01-05) |
| Expression Detected | |
| Primary Root | H epidermis H cortex |

| Table 3-16. T2 Mature Plant Expression | Organs/Tissues screened |
|---|---|
| Events Screened: n=4 | Events Expressing: n=3 (02, 03, 04) |
| Expression Detected | |
| Flower | H stamen H filament H anther |

| Aerial organs | H flowers |
| Mature Root | H epidermis L cortex H stele |

| Table 4-16. | Promoter utility |
|---|---|
| Trait Area: | Water Use Efficiency, Nutrient Use Efficiency, Sterility |
| Sub-trait Area: Drought Tolerance, Nitrogen and Phosphorous Utilization, Male Sterility ||
| Utility: Among other uses this promoter sequence is useful to improve the uptake of water and nutrients from the soil. It could also be used to engineer male sterility. ||

| Construct: | YP2608 |
|---|---|
| Promoter candidate I.D: | 25656951 |
| cDNA I.D: | 5680676 |
| Events expressing: | 02, 03 ,04 |

One or more fragments of the above described promoter are identified in the miscellaneous feature section of the relevant SEQ ID in the Sequence Listing. Those fragments were tested for promoter activity by the same procedures as described above, and the results are summarized below.
For Ceres Promoter PD3739, no expression is observed.

| Promoter Expression Report YP2683 (SEQ ID NO: 18) ||
|---|---|
| Promoter Tested In: *Arabidopsis thaliana*, Wassilewskija (WS) ecotype ||
| Spatial expression summary: ||
| Flower | L petal L anther H pollen |
| Stem | L cortex L vascular H xylem H procambium |
| Leaf | H vascular L epidermis L stomata |
| Cotyledon | L epidermis L hydathode |
| Primary Root | L cortex L epidermis H vascular |
| Aerial Organs | L flower |
| Mature Root | L epidermis H cortex H vascular H quiescent center |
| Observed expression pattern: ||
| T1 Mature expression: Expression is primarily in pollen and in vascular tissues in leaves and stems. Expression appears to be strongest in the meristematic vascular cells (procambium), which gives rise to the xylem and phloem. ||
| T2 Seedling expression: Expression is observed primarily in the root vasculature. Weak expression was also observed in the epidermis of the seedling. ||
| T2 Mature: Weak expression was observed in the floral tissue. Strong expression was detected in the root, primarily in the cortex and vascular tissues as well as the quiescent center. ||
| Source Promoter Organism: *Arabidopsis thaliana*, Columbia (Col) ecotype ||
| Vector: | pNewbin4-HAP1-GFP |
| Marker Type: | GFP-ER |
| Generation Screened: X T1 Mature  X T2 Seedling  X T2 Mature ||
| Table 1-17. T1 Mature Plant Expression    Organs/Tissues screened ||
| Events Screened:    n= 8 | Events Expressing:    n= 3 (02, 03, 06) |
| Expression Detected ||
| Flower | L petal L anther H pollen |
| Stem | L cortex L vascular H xylem H procambium |
| Leaf | H vascular L epidermis L stomata |

| Table 2-17. T2 Seedling Expression    Tissues Screened ||
|---|---|
| Events Screened: n= 6 | Events Expressing: n= 3 (02, 05, 06) |

| Expression Detected | |
|---|---|
| Cotyledon | L epidermis  L hydathode |
| Primary Root | L epidermis  L cortex  H vascular |

| Table 3-17. T2 Mature Plant Expression | Organs/Tissues screened | |
|---|---|---|
| Events Screened: n= 6 | Events Expressing: | n= 4 (02, 03, 05, 06) |
| Expression Detected | | |
| Aerial organs | L flower | |
| Mature Root | L epidermis  H cortex  H vascular  H quiescent center | |

| Table 4-17. | Promoter utility |
|---|---|
| Trait Area: | Sterility, Water Use Efficiency, Nutrient Use Efficiency |
| Sub-trait Area: | Male-Sterility, Drought Tolerance, Nitrogen and Phosphorous Utilization |
| Utility: Among other uses this promoter sequence is useful to improve the uptake of water and nutrients from the soil. The pollen expression could be used to engineer male sterility for gene-confinement. ||

| Construct: | YP2683 |
|---|---|
| Promoter candidate I.D: | 41958148 |
| cDNA I.D: | 36558613 |
| Events expressing: | 02, 03, 05, 06 |

| Promoter Expression Report  YP2816 (SEQ ID NO:19) | |
|---|---|
| Promoter Tested In: *Arabidopsis thaliana*, Wassilewskija (WS) ecotype | |
| Spatial expression summary: | |
| Flower | H vascular  H ovule |
| Silique | H septum |
| Ovule | Pre-fertilization: H outer integument |
| | Post-fertilization: H seed coat  H embryo |
| Embryo | H radicle  H late mature |
| Stem | H epidermis  H vascular  H xylem  H phloem |
| Leaf | L vascular  H trichome |
| Hypocotyl | L epidermis |
| Cotyledon | L epidermis |
| Rosette Leaf | H epidermis  H trichome  H primordia |
| Primary Root | H epidermis  H cortex  H vascular  L quiescent center  L columella |
| Mature Root | H epidermis  H cortex  H vascular  H endodermis  H parenchyma  H stele |
| Observed expression pattern: All cells in root. | |
| T1 Mature expression: Promoter expression is observed in the pre-fertilized ovule integuments as well as the seed coat and the developing radicle of the embryo. Expression is also observed weakly in the vasculature of the stem and leaf trichomes. | |
| T2 Seedling expression: Seedling expression is primarily in all cells of the root. | |
| T2 Mature: Expression is strong in all cells of the root analyzed. | |
| Source Promoter Organism: *Arabidopsis thaliana*, Columbia (Col) ecotype | |
| Vector: | pNewbin4-HAP1-GFP |
| Marker Type: | GFP-ER |
| Generation Screened: X T1 Mature  X T2 Seedling  X T2 Mature | |

| Table 1-18. T1 Mature Plant Expression | Organs/Tissues screened | |
|---|---|---|
| Events Screened: n= 8 | Events Expressing: | n= 5 (02, 03, 05, 07, 08) |

| Expression Detected | |
|---|---|
| Flower | H vascular  H ovule |
| Silique | H septum |
| Ovule | Pre-fertilization: H outer integument |
|  | Post-fertilization: H seed coat  H embryo |
| Embryo | H late  H radicle |
| Stem | H epidermis  H vascular  H xylem  H phloem |
| Leaf | L vascular  H trichome |

| Table 2-18. T2 Seedling Expression | Tissues Screened |
|---|---|
| Events Screened: n= 6 | Events Expressing: n= 3 (02, 03, 05) |
| Expression Detected | |
| Hypocotyl | L epidermis |
| Cotyledon | L epidermis |
| Rosette Leaf | H epidermis  H trichome  H primordia |
| Primary Root | H epidermis  H cortex  H vascular  L quiescent center  L columella |

| Table 3-18. T2 Mature Plant Expression | Organs/Tissues screened |
|---|---|
| Events Screened:  n= 6 | Events Expressing:  n= 5 (01-05) |
| Expression Detected | |
| Leaf | H trichome |
| Aerial organs | L stem |
| Mature Root | H epidermis  H cortex  H vascular  H endodermis  H parenchyma  H stele |

| Table 4-18. | Promoter utility |
|---|---|
| Trait Area: Water Use Efficiency, Nutrient Use Efficiency | |
| Sub-trait Area: Drought Tolerance, Nitrogen and Phosphorous Use Efficiency | |
| Utility: Among other uses this promoter sequence is useful to improve the uptake and utilization of water and nutrients from the soil and the transport of water throughout the vasculature. | |

| Construct: | YP2816 |
|---|---|
| Promoter candidate I.D: | 15372106 |
| cDNA I.D: | 36540030 |
| Events expressing: | 01-05, 07, 08 |

One or more fragments of the above described promoter are identified in the miscellaneous feature section of the relevant SEQ ID in the Sequence Listing. Those fragments were tested for promoter activity by the same procedures as described above, and the results are summarized below.
Ceres Promoter PD3238 expresses weakly in roots in rice. No expression is observed for Ceres Promoter PD3229 and Ceres Promoter PD3243.

| Promoter Expression Report  YP2832 (SEQ ID NO:20) | |
|---|---|
| Promoter Tested In: *Arabidopsis thaliana*, Wassilewskija (WS) ecotype | |
| Spatial expression summary: | |
| Flower | H pedicel  H receptacle  H style |
| Silique | H style  H septum  H abscission zone |
| Stem | H epidermis  H cortex |
| Leaf | L stomata |
| Primary Root | L epidermis  H cortex  H endodermis  H phloem |
| Lateral Root | H primordia |
| Aerial Organs | H stem |
| Mature Root | L epidermis  H cortex  H endodermis  H phloem  H lateral roots |
| Observed expression pattern: | |

| |
|---|
| T1 Mature expression: Expression is primarily observed in the epidermis and cortical layers of the stem tissue. |
| T2 Seedling expression: The promoter is expressed in the most mature parts of the primary root, and is not detected in the root tips. The root expression is also observed in the buds giving rise to the secondary root branches. No expression is observed in the hypocotyl or cotyledons. |
| T2 Mature expression: Expression observed in non-leaf tissues. |
| Source Promoter Organism: *Arabidopsis thaliana*, Columbia (Col) ecotype |
| Vector: pNewbin4-HAP1-GFP |
| Marker Type: GFP-ER |
| Generation Screened: X T1 Mature  X T2 Seedling  XT2 Mature |

| Table 1-19. T1 Mature Plant Expression | Organs/Tissues screened |
|---|---|
| Events Screened:  n= 6 | Events Expressing:  n= 5 (01-05) |
| Expression Detected | |
| Flower | H pedicel H receptacle H style |
| Silique | H style H septum H abscission zone |
| Stem | H epidermis H cortex |
| Leaf | L stomata |

| Table 2-19. T2 Seedling Expression | Tissues Screened |
|---|---|
| Events Screened: n= 6 | Events Expressing: n= 4 (01, 02, 04, 05) |
| Expression Detected | |
| Primary Root | L epidermis  H cortex H endodermis  H phloem |
| Lateral root | H primordia |

| Table 3-19. T2 Mature Plant Expression | Organs/Tissues screened |
|---|---|
| Events Screened:  n= 6 | Events Expressing:  n= 6 (01-06) |
| Expression Detected | |
| Aerial organs | H stem |
| Mature Root | H lateral root L epidermis  H cortex H endodermis H phloem |

| Table 4-19. | Promoter utility |
|---|---|
| Trait Area: | Source, Water Use Efficiency, Nutrient Use Efficiency |
| Sub-trait Area: Carbon/Nitrogen Partitioning, Drought Tolerance, Nitrogen and Phosphorous Use Efficiency | |
| Utility: Among other uses this promoter sequence is useful to engineer the storage of carbon into stem and root material, to improve the uptake of water and nutrients into the roots from the soil, and to protect the plants from pests. | |

| Construct: | YP2832 |
|---|---|
| Promoter candidate I.D: | 32258957 |
| cDNA I.D: | 36551046 |
| Events expressing: | 01-06 |

| Promoter Expression Report PD2995 (aka PD2263) (SEQ ID NO:21) | |
|---|---|
| Promoter Tested In: *Arabidopsis thaliana*, Wassilewskija (WS) ecotype | |
| Spatial expression summary: | |
| Flower | H epidermis L petal H carpel H style H silique H pedicel |
| Silique | H epidermis H style H carpel H septum H ovule |
| Ovule | Pre-fertilization: H outer integument |

|  | Post-fertilization: H seed coat H outer integument |
| --- | --- |
| Embryo | H mature endosperm H mature |
| Stem | H epidermis H pith |
| Leaf | L epidermis H mesophyll |
| Inflorescence | H floral meristem H floral primordia |
| Hypocotyl | H epidermis H cortex H vascular |
| Cotyledon | H epidermis H mesophyll |
| Rosette Leaf | H epidermis H mesophyll H stipule |
| Primary Root | H epidermis H cortex H vascular H quiescent center H root meristem H root cap |
| Lateral root | H primordia H flanking cells H lateral root cap |
| Aerial organs | H inflorescence H floral meristem H floral primordia H flowers H silique H stem H leaf |
| Root | H mature root |

Observed expression pattern:
T1 Mature expression: High broad GFP expression throughout aerial organs. High GFP expression in flowers, stems, and leaves. GFP expressed in floral meristems and primordia. High GFP expression in carpels, ovules and developing seed in silique. GFP expressed in outer integuments, endosperm, seed coat and embryos in ovules. GFP expressed in pith and epidermis in stem and epidermis and mesophyll of leaf.
T2 Seedling expression: High GFP expression in aerial organs and root. High GFP expression in epidermis and mesophyll cells of cotyledon and rosette leaf. High GFP expression in epidermis, cortex and vasculature of hypocotyl and root. GFP expressed in root meristem cells and root cap.
T2 Mature expression: High broad GFP expression throughout aerial organs and roots.

| Source Promoter Organism: | *Arabidopsis thaliana*, Columbia (Col) ecotype |
| --- | --- |
| Vector: | CRS338-GFP |
| Marker Type: | GFP-ER |
| Generation Screened: | X T1 Mature  X T2 Seedling  X T2 Mature |

| Table 1-20. T1 Mature Plant Expression | Organs/Tissues screened |
| --- | --- |
| Events Screened: n=6 | Events Expressing: n=6 (01-06) |
| Expression Detected | |
| X Flower | H pedicel  L petal H carpel H style  H epidermis H silique |
| X Silique | H style H carpel H septum H epidermis H ovule |
| X Ovule | Pre-fertilization: H outer integument |
|  | Post-fertilization: H outer integument  H seed coat  H mature endosperm |
| X Embryo | H mature |
| X Stem | H epidermis H pith |
| X Leaf | H mesophyll  L epidermis |
| X Inflorescence | H floral meristem H floral primordia |

| Table 2-20. T2 Seedling Expression | Tissues Screened |
| --- | --- |
| Events Screened: n=6 | Events Expressing: n=6 (01-06) |
| GFP Expression Detected | |
| X Hypocotyl | H epidermis H cortex H vascular |
| X Cotyledon | H mesophyll H epidermis |
| X Rosette Leaf | H mesophyll H epidermis  H stipule |
| X Primary Root | H epidermis  H cortex  H vascular  H quiescent center H root meristem  H root cap |
| X Lateral root | H primordia H flanking cells ☐ H lateral root cap |

| Table 3-20. T2 Mature Plant Expression | Organs/Tissues screened |
| --- | --- |

| Events Screened: | n=6 | Events Expressing: | n=6 (01-06) |
|---|---|---|---|
| GFP Expression Detected | | | |
| X Aerial organs | H inflorescence H floral meristem H floral primordia H flowers H silique H stem H leaf | | |
| X Root | H mature root | | |

| Table 4-20. | Promoter utility |
|---|---|
| Trait Area: | Water Use Efficiency, PG&D, Seed, Nutrient, and Yield |
| Sub-trait Area: | Water use efficiency, growth rate, seed yield, and nutrient utilization |
| Utility: Among other uses this promoter sequence is useful to modulate plant growth and architecture and the utilization and water and nutrients. | |

| Construct: | PD2263 |
|---|---|
| Promoter candidate I.D: | 38960222 |
| cDNA I.D: | 36549595 |
| Events expressing: | 01-06 |

One or more fragments of the above described promoter are identified in the miscellaneous feature section of the relevant SEQ ID in the Sequence Listing. Those fragments were tested for promoter activity by the same procedures as described above, and the results are summarized below.

For Ceres Promoter PD2926, expression is weak compared to the full-length promoter PD2995; the promoter remains active in all tissues except the embryo.

For Ceres Promoter PD3048, expression is weak compared to the full-length promoter PD2995; the promoter remains active in all tissues.

For Ceres Promoter PD3182, no expression is observed.

For Ceres Promoter PD3345, expression is very weak.

For Ceres Promoter PD3503, no expression is observed.

For Ceres Promoter PD3676, expression is weak compared to the full-length promoter PD2995; the promoter expresses at higher levels in vegetative tissues than in reproductive tissues.

| Promoter Expression Report PD2999 (aka PD2258) (SEQ ID NO:22) | |
|---|---|
| Promoter Tested In: *Arabidopsis thaliana*, Wassilewskija (WS) ecotype | |
| Flower | H pedicel H sepal H carpel H style H stigma H silique |
| Silique | H stigma H style H carpel H placentae H funiculus H epidermis H ovule |
| Ovule | Pre-fertilization: H primordia H inner integument H outer integument H funiculus |
| | Post-fertilization: H outer integument H seed coat H early endosperm H mature endosperm H embryo |
| Embryo | H suspensor H heart H mature H radicle H cotyledons |
| Stem | H epidermis H cortex H interfascicular region H vascular H xylem H phloem H pith |
| Leaf | H mesophyll H epidermis |
| Inflorescence | H floral meristem H floral primordia |
| Hypocotyl | H epidermis H cortex H vascular |
| Cotyledon | H epidermis H vascular |
| Rosette Leaf | H epidermis |
| Primary Root | H vascular H root cap |
| Observed expression pattern: | |
| T1 Mature expression: Broad high GFP expression throughout aerial organs. High GFP expression in inflorescence, floral meristem, flowers, siliques. High GFP expression throughout tissues of silique. GFP expressed in carpels, placenta, ovule primordia, developing ovules, embryo, and endosperm. High GFP expression in outer integuments and seed coats of developing ovules and seed. High GFP expression in vascular and ground tissues of stem. High GFP expression in epidermis and | |

| | |
|---|---|
| mesophyll cells of leaf. | |
| T2 Seedling expression: Broad expression throughout aerial organs and vasculature of root. | |
| Source Promoter Organism: *Arabidopsis thaliana*, Columbia (Col) ecotype | |
| Vector: | CRS338-GFP |
| Marker Type: | GFP-ER |
| Generation Screened: X T1 Mature  X T2 Seedling | |

| Table 1-21. T1 Mature Plant Expression | Organs/Tissues screened |
|---|---|
| Events Screened: n=6 | Events Expressing: n=4 (01, 02, 04, 06) |
| GFP Expression Detected | |
| X Flower | H pedicel H sepal H carpel H style H stigma H silique |
| X Silique | H stigma H style H carpel H placentae H funiculus H epidermis H ovule |
| X Ovule | Pre-fertilization: H primordia H inner integument H outer integument H funiculus<br>Post-fertilization: H outer integument H seed coat H early endosperm H mature endosperm H embryo |
| X Embryo | H suspensor H heart H mature H radicle H cotyledons |
| X Stem | H epidermis H cortex H interfascicular region H vascular H xylem H phloem H pith |
| X Leaf | H mesophyll H epidermis |
| X Inflorescence | H floral meristem H floral primordia |

| Table 2-21. T2 Seedling Expression | Tissues Screened |
|---|---|
| Events Screened: n=6 | Events Expressing: n=5 (01-04, 06) |
| ☐ No GFP Expression Detected | |
| X Hypocotyl | H epidermis H cortex H vascular |
| X Cotyledon | H epidermis H vascular |
| X Rosette Leaf | H epidermis |
| X Primary Root | H vascular H root cap |

| Table 3-21. | Promoter utility |
|---|---|
| Trait Area: | Water use efficiency, PG&D, Seed, Nutrient, Yield |
| Sub-trait Area: | Water use efficiency, growth rate, seed size and yield, and nutrient use |
| Utility: Among other uses this promoter sequence is useful to improve: Water use efficiency, PG&D, Seed, Nutrient, Yield | |

| | |
|---|---|
| Construct: | PD2258 |
| Promoter candidate I.D: | 38960200 |
| cDNA I.D: | 23478038 |
| Events expressing: | 01, 02, 04, 06 |

One or more fragments of the above described promoter are identified in the miscellaneous feature section of the relevant SEQ ID in the Sequence Listing. Those fragments were tested for promoter activity by the same procedures as described above, and the results are summarized below.

For Ceres Promoter PD2929, expression is very weak compared to the full-length promoter PD2999; the promoter remains active in all tissues.

For Ceres Promoter PD3183, expression is only detected in anthers and stigma.

For Ceres Promoter PD3240, expression is very weak compared to the full-length promoter PD2999; the promoter remains active in all tissues.

For Ceres Promoter PD3266, no expression is detected in rice.

| Promoter Expression Report PD3141 (SEQ ID NO:23) |
|---|
| Promoter Tested In: *Oryza sativa* |
| Spatial expression summary:<br>Tiller: not-specific<br>Main culm: bundle sheath, endodermis, epidermis, internode, ligule, node, pericycle, phloem, sclerenchyma layer, vasculature, xylem<br>Root: cortex, epidermis, vascular<br>Leaf: epidermis, leaf blade, leaf sheath, mesophyll, petiole, stipule, stomata, vasculature<br>Meristem: floral meristem, shoot apical meristem, vegetative meristem<br>Panicle: flag leaf, ovary, peduncle, primary branch, rachilla, rachis, spiklet<br>Spikelet: floral meristem, shoot apical meristem, vegetative meristem |
| Observed expression pattern: Broad |
| Source Promoter Organism: *Oryza sativa* |
| Vector: Binary DF EGFP |
| Marker Type: EGFP |
| Generation Screened: T0 Seedling and T0 Mature |
| Induction Data |

| Table 1-22. T0 Seedling Expression    Organs/Tissues screened |
|---|
| Events Screened: n = 12   Events Expressing: n = 9 (01, 03-04, 06-11) |
| Organs<br>Tiller: not-specific<br>Main culm: not-specific<br>Root: not-specific<br>Leaf: not-specific<br>Meristem: not-specific |

| Table 2-22. T0 Mature Plant Expression    Tissues Screened |
|---|
| Events Screened: n = 6    Events Expressing: n = 6 (01,04,07-08,11,14) |
| Organs<br>Main culm: bundle sheath, endodermis, epidermis, internode, ligule, node, pericycle, phloem, sclerenchyma layer, vasculature, xylem<br>Root: cortex, vascular<br>Panicle: flag leaf, ovary, peduncle, primary branch, rachilla, rachis, spiklet<br>Spiklet: flag leaf, floret(palea), lemma, ovule, pedicle, pollen, seed, stigma<br>Leaf: epidermis, leaf blade, leaf sheath, mesophyll<br>Meristem: floral meristem, shoot apical meristem, vegetative meristem |
| Promoter utility |
| Trait Area: Yield, Composition, Disease, Stress Tolerance, Nutrient Use Efficiency, Nutrient Utilization |
| Sub-trait Area: Biomass, Lignin composition, Disease resistance, Salt tolerance, Drought tolerance, Phosphate and Nitrate Use Efficiency, Phosphate and Nitrate Utilization |
| Utility: Among other uses, this promoter sequence is useful to improve: the biomass of the plants under normal and stressful conditions through the overexpression of trait-specific transgenes. |

| |
|---|
| Construct: PD3141 |
| SR/OS Line: OS00486 |
| Promoter candidate I.D: 54507599 |
| cDNA I.D: NA |
| Events expressing: 01, 03-04, 06-11, 14 |

| |
|---|
| Promoter Expression Report YP2680 (SEQ ID NO:24) |
| Promoter Tested In: *Arabidopsis thaliana* |
| Spatial expression summary:<br>Leaf: epidermis, vasculature<br>Flower: vascular<br>Silique: abscission zone, vascular<br>Primary root: cortex, epidermis, root hairs, vascular<br>Lateral root: cortex, epidermis, vascular<br>Mature root: not-specific |
| Observed expression pattern: Primarily root expression |
| Source Promoter Organism: *Arabidopsis thaliana* |
| Vector: Binary TC(815) |
| Marker Type: erGFP |
| Generation Screened: T1 Mature, T2 Seedling, T2 Mature |

| |
|---|
| Table 1-23. T1 Mature Plant Expression      Organs/Tissues screened |
| Events Screened: n = 8    Events Expressing: n = 7 (01, 03-08) |
| Organs<br>Leaf: epidermis, vasculature<br>Flower: vascular<br>Silique: abscission zone, vascular |

| |
|---|
| Table 2-23. T1 Seedling Expression      Tissues Screened |
| Events Screened: n = 5    Events Expressing: n = 5 (01-05) |
| Primary root: cortex, epidermis, root hairs, vascular<br>Lateral root: cortex, epidermis, vascular |

| |
|---|
| Table 3-23. T2 Mature Plant Expression      Organs/Tissues screened |
| Events Screened: n = 6    Events Expressing: n = 5 (01-03, 06, 08) |
| Organs<br>Mature root: not-specific<br>Primary root: cortex, epidermis, vascular<br>Lateral root: cortex, epidermis, vascular |
| Promoter utility: |
| Trait Area: Drought Tolerance, Nutrient Utilization |
| Sub-trait Area: Water Utilization, Phosphate and Nitrate Utilization |
| Utility: Among other uses, this promoter sequence is useful to improve: the uptake and transport of water and nutrients from the soil to support vegetative growth. |
| Notes: 1000 nt upstream of atg |

| |
|---|
| Construct: YP2664 |
| SR/OS Line: SR04406 |
| Promoter candidate I.D: 41958160 |
| cDNA I.D: 36511557 |
| Events expressing: 01-08 |

One or more fragments of the above described promoter are identified in the miscellaneous feature section of the relevant SEQ ID in the Sequence Listing. Those fragments were tested for promoter activity by the same procedures as described above, and the results are summarized below.

Ceres Promoter PD3584 is a strong, broadly expressing promoter; comparable to the full-length promoter PD3141.

| | |
|---|---|
| Promoter Expression Report PD3147 (aka YP2663) (SEQ ID NO:25) | |
| Promoter Tested In: *Arabidopsis thaliana*, Wassilewskija (WS) ecotype | |
| Spatial expression summary: | |
| Flower | H pedicel H sepal H petal H filament H anther L carpel L silique |
| Silique | L carpel L funiculus |
| Stem | H epidermis H cortex H vascular H xylem H phloem L pith |
| Leaf | H epidermis H mesophyll H vascular |
| Hypocotyl | H epidermis H cortex |
| Cotyledon | H epidermis H mesophyll |
| Rosette Leaf | H epidermis H mesophyll |
| Aerial organs | H inflorescence H flowers L silique H stem H leaf |
| Observed expression pattern: | |
| T1 Mature expression: High GFP expressed in aerial tissues. High GFP expression in leaf, stem and inflorescence. High GFP expressed in pedicels, sepals, petals and stamens. Low GFP expression in epidermis of silique. No GFP expression observed in embryo. High GFP expression in epidermis, cortex, phloem and xylem cells of vasculature. Low GFP expression in pith sells of stem. High GFP expression in epidermis, mesophyll and vasculature of leaves. | |
| T2 Seedling expression: High GFP expressed in aerial tissues. High GFP expression in epidermis and mesophyll cells of cotyledons and rosette leaves and in epidermis and cortex of hypocotyls. No GFP expression observed in roots. | |
| T2 Mature expression: GFP expressed in aerial tissues. High GFP expression in leaf, stem and inflorescence. No GFP expression observed in roots. | |
| Source Promoter Organism: *Arabidopsis thaliana*, Columbia (Col) ecotype | |
| Vector: | pNewbin4-HAP1-GFP |
| Marker Type: | GFP-ER |
| Generation Screened: X T1 Mature X T2 Seedling X T2 Mature | |
| Inductions completed. | |

| Treatment: | Age: | Gen: | Time points: | Events Screened / Response | Response: |
|---|---|---|---|---|---|
| 1. Nitrogen - high N to low N [14.3 mM KNO₃ to 28.6 mM Mannitol] | 4 wks | T2 | 72 hrs | 6/0 | No |

| | |
|---|---|
| Inducible expression summary: | |
| Treatment: Time point induced: Organs induced: Tissues induced: | |

| Table 1-24. T1 Mature Plant Expression | Organs/Tissues screened |
|---|---|
| Events Screened: n=6 | Events Expressing: n=4 (02, 04-06) |

| GFP Expression Detected | |
|---|---|
| X Flower | H pedicel  H sepal  H petal  H filament  H anther  L carpel  L silique |
| X Silique | L carpel  L funiculus |
| X Stem | H epidermis  H cortex  H vascular  H xylem  H phloem  L pith |
| X Leaf | H mesophyll  H vascular  H epidermis |

| Table 2-24. T2 Seedling Expression | Tissues Screened | |
|---|---|---|
| Events Screened: n=6 | | Events Expressing: n=4 (02, 04-06) |
| GFP Expression Detected | | |
| X Hypocotyl | H epidermis  H cortex | |
| X Cotyledon | H mesophyll  H epidermis | |
| X Rosette Leaf | H mesophyll  H epidermis | |

| Table 3-24. T2 Mature Plant Expression | Organs/Tissues screened | |
|---|---|---|
| Events Screened: n=5 | | Events Expressing: n=4 (02, 04-05) |
| GFP Expression Detected | | |
| X Aerial organs | H inflorescence  H flowers  L silique  H stem  H leaf | |

| Table 5-24. | Promoter utility |
|---|---|
| Trait Area: | PG&D, Confinement, Hybrid Production |
| Sub-trait Area: Plant Size, Growth Rate, Carbon Fixation | |
| Utility: Among other uses this promoter sequence is useful to improve carbon fixation in above ground tissues to increase biomass and seed yield. Expression is useful for engineering of carbon and nitrogen ratios. Expression in flowers is deployed for sterility and confinement. | |

| Construct: | YP2663 |
|---|---|
| Promoter candidate I.D: | 25087104 |
| cDNA I.D: | 36567145 |
| Events expressing: | 02, 04-06 |

One or more fragments of the above described promoter are identified in the miscellaneous feature section of the relevant SEQ ID in the Sequence Listing. Those fragments were tested for promoter activity by the same procedures as described above, and the results are summarized below. Ceres Promoter PD3721 is a strong, vegetatively expressing promoter; comparable to the full-length promoter PD3147.

| Promoter Expression Report For PT0822 (SEQ ID NO:26) |
|---|
| Promoter Tested In: *Arabidopsis thaliana*, Wassilewskija (WS) ecotype |
| Observed expression pattern: |
| T1 Mature expression: Expression observed in mature root only. |
| T2 Seedling expression: Expression specific to epidermis and cortex cells of root. |
| Source Promoter Organism: *Arabidopsis thaliana*, Columbia (Col) ecotype |
| Vector: pNewbin4-HAP1-GFP |
| Marker Type: |
| Generation Screened: T1 Mature  T2 Seedling  T2 Mature |

| Table 1-25. T1 Mature Plant Expression | Organs/Tissues screened |
|---|---|
| Root | H epidermis |

| Table 2-25. T2 Seedling Expression | Tissues Screened |
|---|---|
| Expression Detected | |
| Primary Root | H epidermis  H cortex |

| Promoter Expression Report for PD3389 (nucleotides 601-1000 of SEQ ID NO:26) |
|---|
| Promoter Tested In: *Oryza sativa* |
| Spatial expression summary:<br><br>T0 Seedling<br><br>X Root expression in:<br>CORTEX<br> EPIDERMIS<br> ROOT CAP<br><br>T0 Mature<br><br>X Root expression: non-specific. |
| Observed expression pattern:<br>T0 Seedling: Expression observed in the root only.<br>T2 Seedling expression: Expression specific to epidermis and cortex cells of root. |
| Deletion of root-specific promoter PT0822. 600 nucleotides were deleted from the 5'end of the 1000 nucleotide PT0822 promoter (SEQ ID NO: 26). |
| Source Promoter Organism:     *Arabidopsis thaliana*, Columbia (Col) ecotype |
| Generation Screened:     T0 Seedling and T0 Mature |

| Table 1-26. T0 Seedling Expression    Organs/Tissues screened |
|---|
| Events Screened:    n = 16      Events Expressing : n = 3 (01, 05,13) |
| Organs<br>X Root expression in:<br>CORTEX<br> EPIDERMIS<br> ROOT CAP |

| Table 2-26. T0 Mature Plant Expression | Organs/Tissues screened |
|---|---|
| Events Screened: n = 4 | Events Expressing: n = 2 (05,13) |
| Organs<br>X Root expression:<br>nonspecific | |

| Promoter utility |
|---|
| Trait Area: Salt tolerance, Drought Tolerance, Nutrient Use Efficiency, Nutrient Utilization |
| Sub-trait Area: Salt tolerance, Drought tolerance, Phosphate and Nitrate Use Efficiency, Phosphate and Nitrate Utilization |
| Utility: Among other uses, this promoter sequence is useful to improve: the biomass of the plants under normal and stressful conditions through the overexpression of trait-specific transgenes. |

One or more fragments of the above described promoter are identified in the miscellaneous feature section of the relevant SEQ ID in the Sequence Listing. Those fragments were tested for promoter activity by the same procedures as described above, and the results are summarized below.

For Ceres Promoter PD3389, expression is observed in the roots of rice seedlings.

The invention being thus described, it will be apparent to one of ordinary skill in the art that various modifications of the materials and methods for practicing the invention can be made. Such modifications are to be considered within the scope of the invention as defined by the following claims. Each of the references from the patent and periodical literature cited herein is hereby expressly incorporated in its entirety by such citation.

What is claimed is:

1. A vector construct comprising:
   a) a first nucleic acid molecule comprising a promoter consisting of the nucleotide sequence of SEQ ID NO: 9 or a nucleotide sequence with at least 95 percent sequence identity to SEQ ID NO:9, wherein said promoter has the promoter activity of SEQ ID NO:9; and
   b) a second nucleic acid molecule to be expressed, wherein said first nucleic acid molecule and said second nucleic acid molecule are heterologous to each other and are operably linked.

2. The vector construct according to claim 1, wherein said first nucleic acid molecule comprises the nucleic acid sequence of SEQ ID NO: 9.

3. The vector construct according to claim 1, wherein said second nucleic acid molecule encodes a polypeptide.

4. The vector construct according to claim 3, wherein said second nucleic acid molecule is operably linked to said first nucleic acid molecule in the sense orientation.

5. The vector construct according to claim 4, wherein said second, nucleic acid molecule is transcribed into an RNA molecule that expresses the polypeptide encoded by said second nucleic acid molecule.

6. The vector construct according to claim 1, wherein said second nucleic acid molecule is operably linked to said first nucleic acid molecule in the antisense orientation.

7. The vector construct according to claim 6, wherein transcription of said second nucleic acid molecule produces an antisense molecule.

8. The vector construct according to claim 1, wherein transcription of said second nucleic acid molecule produces an RNAi molecule against an endogenous gene.

9. The vector construct according to claim 3, wherein said second nucleic acid molecule encodes a polypeptide of agronomic interest, wherein the polypeptide of agronomic interest provides a desirable characteristic associated with plant morphology, physiology, growth and development, yield, nutritional enhancement, disease or pest resistance, environmental tolerance, or chemical tolerance.

10. A plant or plant cell comprising the vector construct according to claim 1.

11. A plant or plant cell stably transformed with the vector construct according to claim 1.

12. A transgenic seed of the plant according to claim 10.

13. A method of directing transcription comprising combining, in an environment suitable for transcription:
   a) a first nucleic acid molecule comprising a promoter consisting of the nucleotide sequence of SEQ ID NO: 9 or a nucleotide sequence with at least 95 percent sequence identity to SEQ ID NO:9, wherein said promoter has the promoter activity of SEQ ID NO:9; and
   b) a second nucleic acid molecule; wherein said first nucleic acid molecule and said second nucleic acid molecule are heterologous to each other and operably linked, and transcribing said second nucleic acid molecule.

14. A method of expressing an exogenous coding region in a plant comprising:

a) transforming at least one plant cell with the vector of claim 1;
b) regenerating at least one stably transformed plant from the at least one transformed plant cell of step (a); and
c) selecting at least one plant containing the transformed plant cell, wherein expression of the second nucleic acid molecule results in production of a polypeptide encoded by said second transcribable nucleic acid molecule.

15. A method of altering the expression of a gene in a plant comprising:
a) transforming a plant cell with the vector construct according to claim 1, and
b) regenerating a stably transformed plant from said transformed plant cell.

16. A plant prepared according to the method of claim 14.

17. A transgenic seed from the plant according to claim 16.

18. A method of producing a transgenic plant, said method comprising:
a) transforming a plant cell with the vector according to claim 1; and
b) growing a plant from said plant cell.

19. The method of claim 18, wherein said second nucleic acid molecule comprises a nucleic acid sequence encoding a polypeptide.

20. The method of claim 18, wherein said second nucleic acid molecule is operably linked to said first nucleic acid molecule in the antisense orientation.

21. The method of claim 18, wherein transcription of said second nucleic acid molecule produces an RNAi molecule.

22. A plant or plant cell comprising the vector construct according to claim 2.

23. A plant or plant cell stably transformed with the vector construct according to claim 2.

24. A transgenic seed of the plant according to claim 22.

25. A method of producing a transgenic plant, said method comprising:
a) introducing into a plant cell the vector according to claim 2; and
b) growing a plant from said plant cell.

\* \* \* \* \*